US012764452B2

(12) United States Patent
Connor

(10) Patent No.: US 12,764,452 B2
(45) Date of Patent: Oct. 13, 2026

(54) EEG MONITORING HEADPHONES AND HEADSETS

(71) Applicant: Robert A. Connor, Wyoming, MN (US)

(72) Inventor: Robert A. Connor, Wyoming, MN (US)

(73) Assignee: Medibotics NC, Ham Lake, MN (US)

( * ) Notice: Subject to any disclaimer, the term of this patent is extended or adjusted under 35 U.S.C. 154(b) by 84 days.

(21) Appl. No.: 18/944,224

(22) Filed: Nov. 12, 2024

(65) Prior Publication Data

US 2025/0071460 A1 Feb. 27, 2025

Related U.S. Application Data

(63) Continuation-in-part of application No. 18/902,821, filed on Sep. 30, 2024, and a continuation-in-part of application No. 18/748,059, filed on Jun. 19, 2024, now Pat. No. 12,201,427, and a continuation-in-part of application No. 18/411,540, filed on Jan. 12, 2024, now Pat. No. 12,310,749, and a continuation-in-part of application No. 18/219,684, filed on Jul. 9, 2023, now abandoned, said application No. 18/748,059 is a continuation-in-part of application No. 18/411,540, filed on Jan. 12, 2024, now Pat. No. 12,310,749, and a continuation-in-part of application No. 18/219,684, filed on Jul. 9, 2023, now abandoned, said application No. 18/411,540 is a continuation-in-part of application No. 18/219,684, filed on Jul. 9, 2023, now abandoned, which is a continuation-in-part of application No. 17/714,988, filed on Apr. 6, 2022, now Pat. No. 11,850,052, and a continuation-in-part (Continued)

(51) Int. Cl.

| | |
|---|---|
| ***A61B 5/291*** | (2021.01) |
| ***A61B 5/00*** | (2006.01) |
| ***G06F 3/01*** | (2006.01) |
| ***H04R 1/10*** | (2026.01) |

(52) U.S. Cl.

CPC ........... *H04R 1/1041* (2013.01); *A61B 5/291* (2021.01); *A61B 5/6803* (2013.01); *H04R 1/1008* (2013.01); *G06F 3/015* (2013.01); *H04R 2420/07* (2013.01)

(58) Field of Classification Search

CPC ..... A61B 5/6803; A61B 5/291; A61B 5/0075; A61B 5/6814; A61B 5/369; A61B 5/375; A61B 2560/0468; A61B 5/24; G06F 3/015; G06F 1/163; G06F 3/011; A61N 1/0476; A61N 1/0526; A61N 1/36025; A61N 1/048; G16H 50/20; G16H 10/60

See application file for complete search history.

(56) References Cited

U.S. PATENT DOCUMENTS 8,798,710 B2 8/2014 Chi
9,204,796 B2 12/2015 Tran (Continued)

*Primary Examiner* — Kharye Pope

(57) ABSTRACT

A wearable device for recording biometric information from a person's brain can be embodied in a pair of smart headphones with electrodes or in a biauricular headset with electrodes. This wearable device can position a plurality of electrodes on a person's head at a subset of the following MCN electrode placement sites: CP1, CP2, CP3, CP4, CP5, CP6, CPz, FC1, FC2, FC3, FC4, FC5, FC6, FCz, O1, O2, Oz, P7, P8, PO7, PO8, TP7 and TP8.

8 Claims, 16 Drawing Sheets

Related U.S. Application Data of application No. 16/838,541, filed on Apr. 2, 2020, now abandoned, said application No. 17/714,988 is a continuation-in-part of application No. 17/665,086, filed on Feb. 4, 2022, now Pat. No. 11,662,819, and a continuation-in-part of application No. 17/136,117, filed on Dec. 29, 2020, now abandoned, and a continuation-in-part of application No. 16/554,029, filed on Aug. 28, 2019, now abandoned, said application No. 17/665,086 is a continuation-in-part of application No. 17/136,117, filed on Dec. 29, 2020, now abandoned, and a continuation-in-part of application No. 16/554,029, filed on Aug. 28, 2019, now abandoned, said application No. 17/136,117 is a continuation-in-part of application No. 16/838,541, filed on Apr. 2, 2020, now abandoned, and a continuation-in-part of application No. 16/737,052, filed on Jan. 8, 2020, now Pat. No. 11,754,542, and a continuation-in-part of application No. 16/568,580, filed on Sep. 12, 2019, now Pat. No. 11,478,158, and a continuation-in-part of application No. 16/554,029, filed on Aug. 28, 2019, now abandoned, said application No. 16/838,541 is a continuation-in-part of application No. 16/554,029, filed on Aug. 28, 2019, now abandoned, and a continuation-in-part of application No. 15/236,401, filed on Aug. 13, 2016, now abandoned, said application No. 16/737,052 is a continuation-in-part of application No. 16/568,580, filed on Sep. 12, 2019, now Pat. No. 11,478,158, and a continuation-in-part of application No. 15/963,061, filed on Apr. 25, 2018, now Pat. No. 10,772,559, said application No. 16/568,580 is a continuation-in-part of application No. 15/963,061, filed on Apr. 25, 2018, now Pat. No. 10,772,559, said application No. 16/554,029 is a continuation-in-part of application No. 16/022,987, filed on Jun. 29, 2018, now Pat. No. 11,172,859, which is a continuation-in-part of application No. 15/136,948, filed on Apr. 24, 2016, now Pat. No. 10,234,942, said application No. 15/963,061 is a continuation-in-part of application No. 15/464,349, filed on Mar. 21, 2017, now Pat. No. 9,968,297, which is a continuation-in-part of application No. 15/136,948, filed on Apr. 24, 2016, now Pat. No. 10,234,942, and a continuation-in-part of application No. 14/562,719, filed on Dec. 7, 2014, now Pat. No. 10,130,277, and a continuation-in-part of application No. 14/330,649, filed on Jul. 14, 2014, now abandoned, said application No. 15/236,401 is a continuation-in-part of application No. 15/136,948, filed on Apr. 24, 2016, now Pat. No. 10,234,942, and a continuation-in-part of application No. 14/599,522, filed on Jan. 18, 2015, now Pat. No. 9,814,426, said application No. 15/136,948 is a continuation-in-part of application No. 14/599,522, filed on Jan. 18, 2015, now Pat. No. 9,814,426, which is a continuation-in-part of application No. 14/562,719, filed on Dec. 7, 2014, now Pat. No. 10,130,277, said application No. 14/330,649 is a continuation-in-part of application No. 13/797,955, filed on Mar. 12, 2013, now Pat. No. 9,456,916, and a continuation-in-part of application No. 13/523,739, filed on Jun. 14, 2012, now Pat. No. 9,042,596.

(60) Provisional application No. 62/972,692, filed on Feb. 11, 2020, provisional application No. 62/851,904, filed on May 23, 2019, provisional application No. 62/796,901, filed on Jan. 25, 2019, provisional application No. 62/791,838, filed on Jan. 13, 2019, provisional application No. 62/430,667, filed on Dec. 6, 2016, provisional application No. 62/322,594, filed on Apr. 14, 2016, provisional application No. 62/303,126, filed on Mar. 3, 2016, provisional application No. 62/169,661, filed on Jun. 2, 2015, provisional application No. 62/160,172, filed on May 12, 2015, provisional application No. 62/089,696, filed on Dec. 9, 2014, provisional application No. 62/017,615, filed on Jun. 26, 2014, provisional application No. 61/939,244, filed on Feb. 12, 2014, provisional application No. 61/932,517, filed on Jan. 28, 2014, provisional application No. 61/729,494, filed on Nov. 23, 2012.

(56) References Cited

U.S. PATENT DOCUMENTS

| | | | | |
|---|---|---|---|---|
| 9,314,183 | B2 | 4/2016 | Chi et al. | |
| 9,320,885 | B2 | 4/2016 | Vasapollo | |
| 9,474,461 | B2 | 10/2016 | Fisher et al. | |
| 9,711,056 | B1 * | 7/2017 | Nguyen | A61B 5/0077 |
| 9,820,670 | B2 | 11/2017 | Parvizi et al. | |
| 10,285,646 | B1 | 5/2019 | Grant et al. | |
| 10,433,756 | B1 | 10/2019 | Bachelder et al. | |
| 10,452,144 | B2 | 10/2019 | Aimone et al. | |
| 10,512,770 | B2 | 12/2019 | Wingeier et al. | |
| 10,535,278 | B2 | 1/2020 | Chahine | |
| 10,564,717 | B1 | 2/2020 | Shahmohammadi et al. | |
| 10,656,710 | B1 | 5/2020 | Shahmohammadi et al. | |
| 10,809,796 | B2 | 10/2020 | Armstrong-Muntner et al. | |
| 10,842,404 | B2 | 11/2020 | Mercier et al. | |
| 10,856,032 | B2 | 12/2020 | Aimone et al. | |
| 10,860,097 | B2 | 12/2020 | Chae | |
| 10,867,720 | B2 | 12/2020 | Mallires et al. | |
| 10,888,240 | B2 | 1/2021 | Parvizi et al. | |
| 10,962,789 | B1 | 3/2021 | Lewis | |
| 10,980,480 | B2 | 4/2021 | Grant et al. | |
| 10,990,175 | B2 | 4/2021 | Forsland et al. | |
| 11,209,654 | B1 | 12/2021 | Lewis | |
| 11,241,183 | B2 | 2/2022 | Leuthardt et al. | |
| 11,272,870 | B2 | 3/2022 | Katnani et al. | |
| 11,301,044 | B1 | 4/2022 | Chevillet et al. | |
| 11,357,434 | B2 | 6/2022 | Bachelder et al. | |
| 11,360,559 | B2 | 6/2022 | Keller et al. | |
| 11,363,980 | B2 | 6/2022 | Dauguet et al. | |
| 11,471,088 | B1 | 10/2022 | Parvizi et al. | |
| 11,540,759 | B2 | 1/2023 | Flood et al. | |
| 11,583,231 | B2 | 2/2023 | Yee et al. | |
| 11,612,331 | B2 | 3/2023 | Wyeth et al. | |
| 11,617,897 | B2 | 4/2023 | Wingren | |
| 11,622,709 | B2 | 4/2023 | Gunasekar et al. | |
| 11,642,081 | B2 | 5/2023 | Kentin et al. | |
| 11,740,696 | B2 | 8/2023 | Keller et al. | |
| 11,744,504 | B2 | 9/2023 | Kele et al. | |
| 11,747,903 | B2 | 9/2023 | Keller et al. | |
| 11,749,426 | B2 | 9/2023 | Futashima et al. | |
| 11,751,796 | B2 | 9/2023 | Han et al. | |
| 11,850,055 | B2 | 12/2023 | Hiratsuka | |
| 11,852,901 | B2 | 12/2023 | Howell et al. | |
| 2006/0252978 | A1 | 11/2006 | Vesely et al. | |
| 2006/0252979 | A1 | 11/2006 | Vesely et al. | |
| 2007/0019279 | A1 | 1/2007 | Goodall et al. | |
| 2007/0106172 | A1 | 5/2007 | Abreu | |
| 2007/0225585 | A1 * | 9/2007 | Washbon | A61B 5/291 600/383 |
| 2009/0134887 | A1 | 5/2009 | Hu et al. | |
| 2011/0298706 | A1 | 12/2011 | Mann | |
| 2013/0056010 | A1 | 3/2013 | Walker et al. | |
| 2013/0102874 | A1 | 4/2013 | Chi | |
| 2013/0242262 | A1 | 9/2013 | Lewis | |
| 2013/0274583 | A1 | 10/2013 | Heck | |

(56) References Cited

U.S. PATENT DOCUMENTS

2014/0023999 A1 1/2014 Greder
2014/0024912 A1 1/2014 Dalke
2014/0107458 A1 4/2014 Op De Beeck et al.
2014/0148872 A1 5/2014 Goldwasser et al.
2014/0223462 A1 8/2014 Aimone et al.
2014/0288406 A1 9/2014 Chai
2014/0316230 A1 10/2014 Denison et al.
2014/0347265 A1 11/2014 Aimone et al.
2015/0065838 A1 3/2015 Wingeier et al.
2015/0066104 A1 3/2015 Wingeier et al.
2015/0088224 A1 3/2015 Goldwasser et al.
2015/0141788 A1 5/2015 Chi et al.
2015/0199010 A1 7/2015 Coleman et al.
2015/0265176 A1 9/2015 Dalke
2015/0379896 A1 12/2015 Yang
2016/0022981 A1 1/2016 Wingeier et al.
2016/0070122 A1 3/2016 Sales
2016/0089045 A1 3/2016 Sadeghian-Motahar et al.
2016/0143554 A1 5/2016 Lim et al.
2016/0174859 A1 6/2016 Oudenhoven et al.
2016/0175589 A1 6/2016 Wingeier
2016/0256086 A1 9/2016 Byrd et al.
2016/0287173 A1 10/2016 Abreu
2016/0361532 A1 12/2016 Wingeier et al.
2016/0361541 A1 12/2016 Wingeier et al.
2016/0367189 A1 12/2016 Aimone et al.
2017/0021158 A1 1/2017 Wingeier et al.
2017/0028197 A1 2/2017 Wingeier et al.
2017/0065816 A1 3/2017 Wingeier et al.
2017/0112444 A1 4/2017 Lin et al.
2017/0113033 A1 4/2017 Wingeier et al.
2017/0135597 A1 5/2017 Mann
2017/0150925 A1 6/2017 Jung
2017/0164857 A1 6/2017 Soulet De Brugiere et al.
2017/0164903 A1 6/2017 Soulet De Brugiere et al.
2017/0172447 A1 6/2017 Mitra et al.
2017/0215759 A1 8/2017 Dudek et al.
2017/0224990 A1 8/2017 Goldwasser et al.
2017/0224991 A1 8/2017 Wingeier et al.
2017/0245778 A1* 8/2017 Liu ........................ A61B 5/165
2017/0258353 A1 9/2017 Jovanovic et al.
2017/0258400 A1 9/2017 Jovanovic et al.
2017/0258410 A1 9/2017 Gras
2017/0281036 A1 10/2017 Parvizi et al.
2017/0319852 A1 11/2017 Wingeier et al.
2017/0340855 A1 11/2017 Soulet De Brugiere et al.
2017/0360321 A1 12/2017 Wolber et al.
2017/0361096 A1 12/2017 Wingeier
2018/0049639 A1 2/2018 Tian
2018/0049661 A1 2/2018 Parvizi et al.
2018/0078206 A1 3/2018 Aimone et al.
2018/0103894 A1 4/2018 Tzvieli
2018/0153470 A1 6/2018 Gunasekar et al.
2018/0192906 A1 7/2018 Soulet De Brugiere et al.
2018/0204276 A1 7/2018 Tumey
2018/0221620 A1 8/2018 Metzger
2018/0235499 A1 8/2018 Zorman et al.
2018/0235500 A1 8/2018 Lee et al.
2018/0236231 A1 8/2018 Wingeier
2018/0236232 A1 8/2018 Soulet De Brugiere et al.
2018/0256887 A1 9/2018 Wingeier et al.
2018/0256888 A1* 9/2018 Wingeier ............. A61N 1/0492
2018/0278984 A1 9/2018 Aimone et al.
2018/0321173 A1 11/2018 Hanein et al.
2018/0344171 A1 12/2018 Straka et al.
2018/0348863 A1 12/2018 Aimone et al.
2018/0353096 A1 12/2018 Mercier et al.
2018/0353725 A1 12/2018 Mercier et al.
2018/0368717 A1 12/2018 Soulet De Brugiere et al.
2019/0000338 A1 1/2019 Van Den Ende et al.
2019/0054298 A1 2/2019 Wingeier et al.
2019/0073605 A1 3/2019 Keller
2019/0101977 A1 4/2019 Armstrong-Muntner et al.
2019/0113973 A1 4/2019 Coleman et al.
2019/0150828 A1* 5/2019 Haraikawa ........... A61B 5/4812
2019/0151654 A1 5/2019 Wingeier et al.
2019/0175910 A1 6/2019 Wingeier
2019/0200925 A1 7/2019 Aimone et al.
2019/0212816 A1* 7/2019 Myrden ................. A61B 5/378
2019/0215592 A1* 7/2019 Lu ........................ H04R 1/1066
2019/0223747 A1* 7/2019 Chou ..................... A61B 5/291
2019/0224481 A1 7/2019 Wingeier
2019/0239807 A1 8/2019 Watson et al.
2019/0246977 A1 8/2019 Miller et al.
2019/0247655 A1 8/2019 Wingeier et al.
2019/0255313 A1 8/2019 Wingeier et al.
2019/0328261 A1 10/2019 Shakour et al.
2019/0336765 A1 11/2019 Charlesworth et al.
2019/0343462 A1 11/2019 Grant et al.
2019/0365270 A1 12/2019 Bachelder et al.
2019/0374766 A1 12/2019 Wingeier et al.
2019/0384392 A1 12/2019 Aimone et al.
2020/0019243 A1 1/2020 Aimone et al.
2020/0046247 A1 2/2020 Wolber et al.
2020/0060571 A1 2/2020 Dauguet et al.
2020/0061375 A1 2/2020 Wingeier et al.
2020/0069206 A1 3/2020 Zaliasl et al.
2020/0081247 A1 3/2020 Khaderi et al.
2020/0094045 A1 3/2020 Wingeier et al.
2020/0094054 A1 3/2020 Sharma et al.
2020/0097076 A1 3/2020 Alcaide et al.
2020/0133393 A1 4/2020 Forsland et al.
2020/0159324 A1 5/2020 Keller et al.
2020/0192478 A1 6/2020 Alcaide et al.
2020/0197701 A1 6/2020 Wingeier et al.
2020/0215321 A1 7/2020 Wingeier
2020/0215326 A1* 7/2020 Wingeier ........... A61N 1/36025
2020/0237249 A1 7/2020 Gunasekar et al.
2020/0264454 A1 8/2020 Mackenzie et al.
2020/0268296 A1 8/2020 Alcaide et al.
2020/0281527 A1 9/2020 Gunasekar et al.
2020/0305786 A1 10/2020 Grant et al.
2020/0316370 A1 10/2020 Hanein et al.
2020/0337653 A1 10/2020 Alcaide et al.
2020/0367789 A1 11/2020 Moffat et al.
2020/0375524 A1 12/2020 Aminifar et al.
2021/0000347 A1 1/2021 Stump
2021/0038106 A1 2/2021 Ramakrishnan et al.
2021/0064128 A1 3/2021 Alcaide et al.
2021/0085235 A1 3/2021 Kamousi et al.
2021/0106825 A1 4/2021 Wingeier et al.
2021/0109594 A1 4/2021 Keller et al.
2021/0113835 A1 4/2021 Wingeier
2021/0121115 A1 4/2021 Chiang
2021/0124422 A1 4/2021 Forsland
2021/0128044 A1 5/2021 Parvizi et al.
2021/0200313 A1 7/2021 Aimone et al.
2021/0223864 A1 7/2021 Forsland et al.
2021/0267539 A1 9/2021 Grant et al.
2021/0282695 A1 9/2021 Goldstein et al.
2021/0338128 A1 11/2021 Le Lous et al.
2021/0353200 A1 11/2021 Xu et al.
2021/0361235 A1 11/2021 Li et al.
2022/0000407 A1 1/2022 Ludwig et al.
2022/0004257 A1 1/2022 Keller et al.
2022/0015701 A1 1/2022 Gunasekar et al.
2022/0022813 A1 1/2022 Gunasekar et al.
2022/0031217 A1 2/2022 Kidmose et al.
2022/0031248 A1 2/2022 Grant et al.
2022/0117535 A1 4/2022 Parvizi et al.
2022/0117536 A1 4/2022 Parvizi et al.
2022/0187912 A1 6/2022 Alcaide et al.
2022/0211313 A1 7/2022 Lee
2022/0233123 A1 7/2022 Telfer et al.
2022/0276707 A1 9/2022 Barascud et al.
2022/0308668 A1 9/2022 Keller et al.
2022/0404910 A1 12/2022 Alcaide et al.
2023/0000416 A1 1/2023 Bachelder et al.
2023/0014065 A1 1/2023 Hanein et al.
2023/0018247 A1 1/2023 Elias
2023/0031613 A1 2/2023 Fleury
2023/0043938 A1 2/2023 Kele
2023/0107040 A1 4/2023 Alcaide et al.
2023/0165503 A1 6/2023 Coyle

(56) References Cited

U.S. PATENT DOCUMENTS

| | | | |
|---|---|---|---|
| 2023/0172468 | A1 | 6/2023 | Kaplan et al. |
| 2023/0214018 | A1 | 7/2023 | Alcaide et al. |
| 2023/0320669 | A1 | 10/2023 | Desai et al. |
| 2024/0138745 | A1 | 5/2024 | Yonce et al. |
| 2024/0189589 | A1 | 6/2024 | Wingeier et al. |

* cited by examiner

EEG MONITORING HEADPHONES AND HEADSETS

CROSS-REFERENCE TO RELATED APPLICATIONS

This patent application is a continuation-in-part of U.S. patent application Ser. No. 18/902,821 filed on 2024 Sep. 30. This patent application is a continuation-in-part of U.S. patent application Ser. No. 18/748,059 filed on 2024 Jun. 19. This patent application is a continuation-in-part of U.S. patent application Ser. No. 18/411,540 filed on 2024 Jan. 12. This patent application is a continuation-in-part of U.S. patent application Ser. No. 18/219,684 filed on 2023 Jul. 9.

U.S. patent application Ser. No. 18/902,821 was a continuation-in-part of U.S. patent application Ser. No. 18/748,059 filed on 2024 Jun. 19. U.S. patent application Ser. No. 18/902,821 was a continuation-in-part of U.S. patent application Ser. No. 18/411,540 filed on 2024 Jan. 12. U.S. patent application Ser. No. 18/902,821 was a continuation-in-part of U.S. patent application Ser. No. 18/219,684 filed on 2023 Jul. 9.

U.S. patent application Ser. No. 18/748,059 was a continuation-in-part of U.S. patent application Ser. No. 18/411,540 filed on 2024 Jan. 12. U.S. patent application Ser. No. 18/748,059 was a continuation-in-part of U.S. patent application Ser. No. 18/219,684 filed on 2023 Jul. 9. U.S. patent application Ser. No. 18/411,540 was a continuation-in-part of U.S. patent application Ser. No. 18/219,684 filed on 2023 Jul. 9. U.S. patent application Ser. No. 18/219,684 was a continuation-in-part of U.S. patent application Ser. No. 17/714,988 filed on 2022 Apr. 6. U.S. patent application Ser. No. 18/219,684 was a continuation-in-part of U.S. patent application Ser. No. 16/838,541 filed on 2020 Apr. 2.

U.S. patent application Ser. No. 17/714,988 was a continuation-in-part of U.S. patent application Ser. No. 17/665,086 filed on 2022 Feb. 4. U.S. patent application Ser. No. 17/714,988 was a continuation-in-part of U.S. patent application Ser. No. 17/136,117 filed on 2020 Dec. 29. U.S. patent application Ser. No. 17/714,988 was a continuation-in-part of U.S. patent application Ser. No. 16/554,029 filed on 2019 Aug. 28. U.S. patent application Ser. No. 17/665,086 was a continuation-in-part of U.S. patent application Ser. No. 17/136,117 filed on 2020 Dec. 29. U.S. patent application Ser. No. 17/665,086 was a continuation-in-part of U.S. patent application Ser. No. 16/554,029 filed on 2019 Aug. 28.

U.S. patent application Ser. No. 17/136,117 was a continuation-in-part of U.S. patent application Ser. No. 16/838,541 filed on 2020 Apr. 2. U.S. patent application Ser. No. 17/136,117 claimed the priority benefit of U.S. provisional patent application 62/972,692 filed on 2020 Feb. 11. U.S. patent application Ser. No. 17/136,117 was a continuation-in-part of U.S. patent application Ser. No. 16/737,052 filed on 2020 Jan. 8. U.S. patent application Ser. No. 17/136,117 was a continuation-in-part of U.S. patent application Ser. No. 16/568,580 filed on 2019 Sep. 12. U.S. patent application Ser. No. 17/136,117 was a continuation-in-part of U.S. patent application Ser. No. 16/554,029 filed on 2019 Aug. 28.

U.S. patent application Ser. No. 16/838,541 claimed the priority benefit of U.S. provisional patent application 62/972,692 filed on 2020 Feb. 11. U.S. patent application Ser. No. 16/838,541 was a continuation-in-part of U.S. patent application Ser. No. 16/554,029 filed on 2019 Aug. 28. U.S. patent application Ser. No. 16/838,541 claimed the priority benefit of U.S. provisional patent application 62/851,917 filed on 2019 May 23. U.S. patent application Ser. No. 16/838,541 claimed the priority benefit of U.S. provisional patent application 62/837,712 filed on 2019 Apr. 23. U.S. patent application Ser. No. 16/838,541 was a continuation-in-part of U.S. patent application Ser. No. 15/236,401 filed on 2016 Aug. 13. U.S. patent application Ser. No. 16/737,052 was a continuation-in-part of U.S. patent application Ser. No. 16/568,580 filed on 2019 Sep. 12. U.S. patent application Ser. No. 16/737,052 was a continuation-in-part of U.S. patent application Ser. No. 15/963,061 filed on 2018 Apr. 25. U.S. patent application Ser. No. 16/568,580 was a continuation-in-part of U.S. patent application Ser. No. 15/963,061 filed on 2018 Apr. 25.

U.S. patent application Ser. No. 16/554,029 claimed the priority benefit of U.S. provisional patent application 62/851,904 filed on 2019 May 23. U.S. patent application Ser. No. 16/554,029 claimed the priority benefit of U.S. provisional patent application 62/796,901 filed on 2019 Jan. 25. U.S. patent application Ser. No. 16/554,029 claimed the priority benefit of U.S. provisional patent application 62/791,838 filed on 2019 Jan. 13. U.S. patent application Ser. No. 16/554,029 was a continuation-in-part of U.S. patent application Ser. No. 16/022,987 filed on 2018 Jun. 29. U.S. patent application Ser. No. 16/022,987 was a continuation-in-part of U.S. patent application Ser. No. 15/136,948 filed on 2016 Apr. 24. U.S. patent application Ser. No. 15/963,061 was a continuation-in-part of U.S. patent application Ser. No. 15/464,349 filed on 2017 Mar. 21.

U.S. patent application Ser. No. 15/464,349 claimed the priority benefit of U.S. provisional patent application 62/430,667 filed on 2016 Dec. 6. U.S. patent application Ser. No. 15/464,349 was a continuation-in-part of U.S. patent application Ser. No. 15/136,948 filed on 2016 Apr. 24. U.S. patent application Ser. No. 15/464,349 was a continuation-in-part of U.S. patent application Ser. No. 14/562,719 filed on 2014 Dec. 7. U.S. patent application Ser. No. 15/464,349 was a continuation-in-part of U.S. patent application Ser. No. 14/330,649 filed on 2014 Jul. 14. U.S. patent application Ser. No. 15/236,401 was a continuation-in-part of U.S. patent application Ser. No. 15/136,948 filed on 2016 Apr. 24. U.S. patent application Ser. No. 15/236,401 was a continuation-in-part of U.S. patent application Ser. No. 14/599,522 filed on 2015 Jan. 18.

U.S. patent application Ser. No. 15/136,948 claimed the priority benefit of U.S. provisional patent application 62/322,594 filed on 2016 Apr. 14. U.S. patent application Ser. No. 15/136,948 claimed the priority benefit of U.S. provisional patent application 62/303,126 filed on 2016 Mar. 3. U.S. patent application Ser. No. 15/136,948 claimed the priority benefit of U.S. provisional patent application 62/169,661 filed on 2015 Jun. 2. U.S. patent application Ser. No. 15/136,948 claimed the priority benefit of U.S. provisional patent application 62/160,172 filed on 2015 May 12. U.S. patent application Ser. No. 15/136,948 was a continuation-in-part of U.S. patent application Ser. No. 14/599,522 filed on 2015 Jan. 18.

U.S. patent application Ser. No. 14/599,522 claimed the priority benefit of U.S. provisional patent application 62/089,696 filed on 2014 Dec. 9. U.S. patent application Ser. No. 14/599,522 was a continuation-in-part of U.S. patent application Ser. No. 14/562,719 filed on 2014 Dec. 7. U.S. patent application Ser. No. 14/599,522 claimed the priority benefit of U.S. provisional patent application 62/017,615 filed on 2014 Jun. 26. U.S. patent application Ser. No. 14/599,522 claimed the priority benefit of U.S. provisional patent application 61/939,244 filed on 2014 Feb. 12. U.S.

patent application Ser. No. 14/599,522 claimed the priority benefit of U.S. provisional patent application 61/932,517 filed on 2014 Jan. 28.

U.S. patent application Ser. No. 14/562,719 claimed the priority benefit of U.S. provisional patent application 61/932,517 filed on 2014 Jan. 28. U.S. patent application Ser. No. 14/330,649 was a continuation-in-part of U.S. patent application Ser. No. 13/797,955 filed on 2013 Mar. 12. U.S. patent application Ser. No. 14/330,649 was a continuation-in-part of U.S. patent application Ser. No. 13/523,739 filed on 2012 Jun. 14. U.S. patent application Ser. No. 13/797,955 claimed the priority benefit of U.S. provisional patent application 61/729,494 filed on 2012 Nov. 23.

The entire contents of these applications are incorporated herein by reference.

FEDERALLY SPONSORED RESEARCH

Not Applicable

SEQUENCE LISTING OR PROGRAM

Not Applicable

BACKGROUND—FIELD OF INVENTION

This invention relates to wearable EEG (electroencephalographic) monitoring devices.

INTRODUCTION

There are numerous potential applications for incorporating electrodes into devices which are worn on a person's head. Such devices can record brainwave activity (e.g. electroencephalographic data) for use as a BCI (Brain-to-Computer Interface) for communication. Such devices can also be used for biometric monitoring to improve a person's health or to detect adverse heath events (e.g. seizures, strokes, or heart attacks).

REVIEW OF THE RELEVANT ART

U.S. patent applications 20060252978 (Vesely et al., Nov. 9, 2006, "Biofeedback Eyewear System") and 20060252979 (Vesely et al., Nov. 9, 2006, "Biofeedback Eyewear System") disclose a biofeedback eyewear system comprising stereo lenses, binaural audio and plurality of electrodes for biofeedback devices. U.S. patent application No. 20070019279 (Goodall et al., Jan. 25, 2007, "Adjustable Lens System with Neural-Based Control") discloses methods and systems for modifying or enhancing vision via analysis of neural or neuromuscular activity. U.S. patent application Ser. No. 20070106172 (Abreu, May 10, 2007, "Apparatus and Method for Measuring Biologic Parameters") discloses support structures for positioning sensors on a physiologic tunnel for measuring physical, chemical and biological parameters of the body and to produce an action according to the measured value of the parameters.

U.S. patent application No. 20090134887 (Hu et al., May 28, 2009, "Contact Sensor") discloses a contact sensor wherein a conductor has an arc shape. U.S. patent applications 20110298706 (Mann, Dec. 8, 2011, "Brainwave Actuated Apparatus") and 20170135597 (Mann, May 18, 2017, "Brainwave Actuated Apparatus") disclose a brainwave actuated apparatus with a brainwave sensor for outputting a brainwave signal, an effector responsive to an input signal, and a controller operatively connected to an output of said brainwave sensor and a control input to said effector. U.S. patent application No. 20130056010 (Walker et al., Mar. 7, 2013, "Autonomous Positive Airway Pressure System") discloses an apparatus, such as in the form of eyeglasses or goggles comprising dual lenses configured to serve as a gas chamber, or as headgear where the chamber is contoured to fit on the user's head and includes all components required to operate APAP, or the device may be configured to be placed on other locations such as the arm, torso, back, or leg.

U.S. patent application No. 20130102874 (Chi, Apr. 25, 2013, "Apparatuses, Systems and Methods for Biopotential Sensing with Dry Electrodes") and U.S. Pat. No. 8,798,710 (Chi, Aug. 5, 2014, "Apparatuses, Systems and Methods for Biopotential Sensing with Dry Electrodes") disclose an electrode with an electrical conductor, a membrane selectively permeable to ionic conduction, and a conductive medium. U.S. patent application No. 20130242262 (Lewis, Sep. 19, 2013, "Enhanced Optical and Perceptual Digital Eyewear") discloses wearable optics with a frame member, a lens, and circuitry within the frame member for enhancing the use of the wearable optics. U.S. patent application No. 20130274583 (Heck, Oct. 17, 2013, "Electrodes Adapted for Transmitting or Measuring Voltages Through Hair") discloses an electrode to measure and/or deliver voltages through skin covered with hair.

U.S. patent application No. 20140023999 (Greder, Jan. 23, 2014, "Detection and Feedback of Information Associated with Executive Function") discloses a neurosensing and feedback device to detect mental states and alert a wearer, such as in real-time. U.S. patent application No. 20140024912 (Dalke, Jan. 23, 2014, "Neurophysiological Dry Sensor") and U.S. patent application No. 20150265176 (Dalke, Sep. 24, 2015, "Neurophysiological Dry Sensor") disclose a sensor assembly of conductive spires. U.S. patent application No. 20140107458 (Op De Beeck et al., Apr. 17, 2014, "Resilient Sensor for Biopotential Measurements") discloses a sensor with a cavity wherein an electrical contacting unit is partially secured and a means for maintaining the electrical contacting unit in a resiliently deformed state when it is in contact with skin.

U.S. patent applications 20140148872 (Goldwasser et al., May 29, 2014, "Wearable Transdermal Electrical Stimulation Devices and Methods of Using Them") and 20150088224 (Goldwasser et al., Mar. 26, 2015, "Wearable Transdermal Electrical Stimulation Devices and Methods of Using Them") disclose devices, systems, and methods for transdermal electrical stimulation. U.S. patent application No. 20140223462 (Aimone et al., Aug. 7, 2014, "System and Method for Enhancing Content Using Brain-State Data") discloses a computer system or method for modulating content based on a person's brainwave data, including modifying presentation of digital content at least one computing device.

U.S. patent application No. 20140288406 (Chai, Sep. 25, 2014, "Line-Contact Dry Electrode") discloses an electrode with a plurality of elastic conductive branches which form a comb-like electrode. U.S. patent application No. 20140316230 (Denison et al., Oct. 23, 2014, "Methods and Devices for Brain Activity Monitoring Supporting Mental State Development and Training") discloses a method for receiving electroencephalography (EEG) data related to a user. U.S. patent application Ser. No. 20140347265 (Aimone et al., Nov. 27, 2014, "Wearable Computing Apparatus and Method") discloses a method performed by a wearable computing device comprising at least one bio-signal measuring sensor, the at least one bio-signal measuring sensor including at least one brainwave sensor.

U.S. patent applications 20150065838 (Wingeier et al., Mar. 5, 2015, "Electrode System for Electrical Stimulation"), 20160361532 (Wingeier et al., Dec. 15, 2016, "Electrode System for Electrical Stimulation"), and 20190374766 (Wingeier et al., Dec. 12, 2019, "Electrode System for Electrical Stimulation") disclose a system for electrically stimulating and/or detecting a person's bioelectrical signals comprising: an array of permeable bodies configured to absorb a solution that facilitates electrical coupling with a body region of the person; and a housing defining an array of protrusions conforming to the body region.

U.S. patent applications 20150066104 (Wingeier et al., Mar. 5, 2015, "Method and System for Providing Electrical Stimulation to a User"), 20160361541 (Wingeier et al., Dec. 15, 2016, "Method and System for Providing Electrical Stimulation to a User"), 20170319852 (Wingeier et al., Nov. 9, 2017, "Method and System for Providing Electrical Stimulation to a User"), 20170028197 (Wingeier et al., Feb. 2, 2017, "Method and System for Providing Electrical Stimulation to a User"), 20190054298 (Wingeier et al., Feb. 21, 2019, "Method and System for Providing Electrical Stimulation to a User") and 20200197701 (Wingeier et al., Jun. 25, 2020, "Method and System for Providing Electrical Stimulation to a User") disclose a method for providing electrical stimulation to a person as they perform a set of tasks during a time window.

U.S. patent application No. 20150141788 (Chi et al., May 21, 2015, "Transducer Assemblies for Dry Applications of Transducers") and U.S. Pat. No. 9,314,183 (Chi et al., Apr. 19, 2016, "Transducer Assemblies for Dry Applications of Transducers") disclose at least one probe extending from a support terminal which penetrate and slide through patches of hair. U.S. patent application Ser. No. 20150199010 (Coleman et al., Jul. 16, 2015, "Systems and Methods for Collecting, Analyzing, and Sharing Bio-Signal and Non-Bio-Signal Data") and U.S. patent application No. 20190113973 (Coleman et al., Apr. 18, 2019, "Systems and Methods for Collecting, Analyzing, and Sharing Bio-Signal and Non-Bio-Signal Data") disclose a system that: captures bio-signal data and non-bio-signal data; and extracts one or more features related to a person interacting with a biofeedback computer system.

U.S. Pat. No. 9,204,796 (Tran, Dec. 8, 2015, "Personal Emergency Response (PER) System") discloses one or more sensors to detect activities of a mobile object and a processor coupled to the sensor and the wireless transceiver to classify sequences of motions into groups of similar postures each represented by a model and to apply the models to identify an activity of the object. U.S. patent application No. 20150379896 (Yang, Dec. 31, 2015, "Intelligent Eyewear and Control Method Thereof") discloses intelligent eyewear including an eyeglass, an eyeglass frame, and a leg with a brainwave recognizer.

U.S. patent applications 20160022981 (Wingeier et al., Jan. 28, 2016, "Electrode System for Electrical Stimulation") and 20170021158 (Wingeier et al., Jan. 26, 2017, "Electrode System for Electrical Stimulation"), 20170065816 (Wingeier et al., Mar. 9, 2017, "Electrode System for Electrical Stimulation"), 20190175910 (Wingeier, Jun. 13, 2019, "Electrode System for Electrical Stimulation"), 20210106825 (Wingeier et al., Apr. 15, 2021, "Electrode System for Electrical Stimulation") and 20240189589 (Wingeier et al., Jun. 13, 2024, "Electrode System for Electrical Stimulation") disclose a system for electrically stimulating a person comprising: a housing portion defining an array of openings; and an array of permeable bodies with portions exposed through the array of openings and wetted with a solution that facilitates electrical coupling between the system and a body region of the person.

U.S. patent application No. 20160070122 (Sales, Mar. 10, 2016, "Computerized Replacement Temple for Standard Eyewear") discloses a computerized eyewear retrofit kit comprising a replacement temple. U.S. patent application No. 20160089045 (Sadeghian-Motahar et al., Mar. 31, 2016, "Bio-Potential Sensing Materials as Dry Electrodes and Devices") discloses a dry electrode made with an electrically-conductive solid material. U.S. Pat. No. 9,320,885 (Vasapollo, Apr. 26, 2016, "Dual-Purpose Sleep-Wearable Headgear for Monitoring and Stimulating the Brain of a Sleeping Person") discloses headgear for monitoring and stimulating the brain of a sleeping person. U.S. patent application No. 20160143554 (Lim et al., May 26, 2016, "Apparatus for Measuring Bioelectrical Signals") discloses using tapered electrodes to measure bioelectrical signals.

U.S. patent application No. 20160174859 (Oudenhoven et al., Jun. 23, 2016, "Electrode for Biopotential Sensing") discloses a plurality of contact pins protruding from a sensor base. U.S. patent applications 20160175589 (Wingeier, Jun. 23, 2016, "Method and System for Providing Electrical Stimulation to a User"), 20180236231 (Wingeier, Aug. 23, 2018, "Method and System for Providing Electrical Stimulation to a User"), 20190224481 (Wingeier, Jul. 25, 2019, "Method and System for Providing Electrical Stimulation to a User"), and 20210113835 (Wingeier, Apr. 22, 2021, "Method and System for Providing Electrical Stimulation to a User") disclose a method for providing electrical stimulation to a person, the method comprising: providing an electrical stimulation device, in communication with a controller, at a head region of the person.

U.S. patent application No. 20160256086 (Byrd et al., Sep. 8, 2016, "Non-Invasive, Bioelectric Lifestyle Management Device") discloses techniques to ascertain a biological condition such as blood glucose level, a heart rate, a blood ketone level, a blood alcohol content, a hydration level, a blood albumin level, and/or a blood electrolyte level. U.S. patent application No. 20160287173 (Abreu, Oct. 6, 2016, "Apparatus Configured to Support a Device on a Head") discloses apparatuses support by at least a portion of a forehead in combination with at least one of a nose, an car, and a head, or present an adjustable apparatus to provide improved fit of a head-positioned apparatus.

U.S. Pat. No. 9,474,461 (Fisher et al., Oct. 25, 2016, "Miniature Wireless Biomedical Telemetry Device") discloses a miniature wireless biomedical telemetry device to record physiological signals from rats, mice and birds, as well as humans. U.S. patent application No. 20160367189 (Aimone et al., Dec. 22, 2016, "Wearable Apparatus for Brain Sensors") discloses a wearable apparatus with an outer band member comprising outer band ends joined by a curved outer band portion of a curve generally shaped to correspond to a user's forehead. U.S. patent application No. 20170112444 (Lin et al., Apr. 27, 2017, "Bio-Signal Sensor") discloses a dry electrode with a plurality of probes.

U.S. patent applications 20170113033 (Wingeier et al., Apr. 27, 2017, "Electrode Positioning System and Method") and 20190255313 (Wingeier et al., Aug. 22, 2019, "Electrode Positioning System and Method") disclose a system and method for electrically stimulating a person, the system comprising: a set of pads configured at head regions of the person; a band having a first end coupled to a first pad of the set of pads and a second end coupled to a second pad of the set of pads; and a bridge coupled the band and to an electrode during use. U.S. patent application No. 20170150925 (Jung, Jun. 1, 2017, "EEG Hair Band") discloses an EEG-monitoring hair band. U.S. patent application Ser. No. 20170164903 (Soulet De Brugiere et al., Jun. 15, 2017, "Autonomous Bioelectric Physiological Signal Acquisition Device") discloses a method for physiological signal acquisition that includes selecting an amplification factor.

U.S. patent application No. 20170164857 (Soulet De Brugiere et al., Jun. 15, 2017, "Method and Device for Bioelectric Physiological Signal Acquisition and Processing") discloses a method for bioelectric physiological signal acquisition and processing which includes converting the analog signals. U.S. patent application No. 20170172447 (Mitra et al., Jun. 22, 2017, "Sensor, System, and Holder Arrangement for Biosignal Activity Measurement") discloses an electrode base and a plurality of pins protruding from the base. U.S. patent application No. 20170215759 (Dudek et al., Aug. 3, 2017, "Self-Contained EEG Recording System") discloses a electroencephalogram sensor comprising a first electrode and a second electrode, wherein the first and second electrodes cooperate to measure a skin-electrode impedance.

U.S. patent application No. 20170224990 (Goldwasser et al., Aug. 10, 2017, "Apparatuses and Methods for Neuromodulation") discloses devices and methods for transdermal electrical stimulation. U.S. patent applications 20170224991 (Wingeier et al., Aug. 10, 2017, "Method and System for Improving Provision of Electrical Stimulation") and 20190247655 (Wingeier et al., Aug. 15, 2019, "Method and System for Improving Provision of Electrical Stimulation") disclose a method and system for providing stimulation to a person, the method including transitioning a stimulation device from a baseline state to a first impedance monitoring state.

U.S. patent application No. 20170258353 (Jovanovic et al., Sep. 14, 2017, "Headsets and Electrodes for Gathering Electroencephalographic Data") and U.S. patent application No. 20170258400 (Jovanovic et al., Sep. 14, 2017, "Headsets and Electrodes for Gathering Electroencephalographic Data") disclose an electrode with a ring in an opening and an arm, wherein the arm has a portion extending outward from the opening. U.S. patent application No. 20170258410 (Gras, Sep. 14, 2017, "Method and Apparatus for Prediction of Epileptic Seizures") discloses a system for predicting epileptic seizures including sensors operable to record a wearer's brain activity.

U.S. patent application No. 20170281036 (Parvizi et al., Oct. 5, 2017, "Methods and Apparatus for Electrode Placement and Tracking"), U.S. Pat. No. 9,820,670 (Parvizi et al., Nov. 21, 2017, "Methods and Apparatus for Electrode Placement and Tracking"), U.S. patent application No. 20180049661 (Parvizi et al., Feb. 22, 2018, "Methods and Apparatus for Electrode Placement and Tracking"), U.S. Pat. No. 10,888,240 (Parvizi et al., Jan. 12, 2021, "Methods and Apparatus for Electrode Placement and Tracking"), U.S. patent application No. 20210128044 (Parvizi et al., May 6, 2021, "Methods and Apparatus for Electrode Placement and Tracking"), U.S. patent application No. 20220117535 (Parvizi et al., Apr. 21, 2022, "Methods and Apparatus for Electrode Placement and Tracking"), and U.S. patent application No. 20220117536 (Parvizi et al., Apr. 21, 2022, "Methods and Apparatus for Electrode Placement and Tracking") disclose tubular members extending out from an electrode body and a reservoir containing a conductive fluid or gel.

U.S. patent application No. 20170340855 (Soulet De Brugiere et al., Nov. 30, 2017, "Device and Method for Stimulating Slow Brain Waves") discloses a device for stimulating slow brain waves. U.S. patent applications 20170360321 (Wolber et al., Dec. 21, 2017, "Electrical Interface System") and 20200046247 (Wolber et al., Feb. 13, 2020, "Electrical Interface System") disclose a system for providing an electrical interface between a transducer and a transducer support device, the system comprising: a body mounted to the transducer support device, the body comprising an interface-to-transducer coupling region; and an interface-to-electronics subsystem coupling region coupled to the body. U.S. patent application No. 20170361096 (Wingeier, Dec. 21, 2017, "Method and System for Providing Electrical Stimulation to a User") discloses a method and device for providing neuromodulation.

U.S. patent application No. 20180049639 (Tian, Feb. 22, 2018, "Dry Electrode, Its Manufacturing Method and Bio-Electromagnetic Wave Detecting Device and Sensor Element Comprising the Dry Electrode") discloses a dry electrode with a flexible substrate and protruding structures arranged on the substrate. U.S. patent application No. 20180078206 (Aimone et al., Mar. 22, 2018, "Wearable Apparatus for Brain Sensors") discloses an apparatus with an outer band, a flexible inner band, and at least one brainwave sensor disposed inwardly along the inner band. U.S. patent application Ser. No. 20180103894 (Tzvieli, Apr. 19, 2018, "Neurofeedback Eyeglasses") discloses using forehead thermal measurements in brain-related treatments such as neurofeedback.

U.S. patent application No. 20180153470 (Gunasekar et al., Jun. 7, 2018, "Electroencephalography Headset and System for Collecting Biosignal Data"), U.S. patent application No. 20200281527 (Gunasekar et al., Sep. 10, 2020, "Electroencephalography Headset and System for Collecting Biosignal Data"), U.S. patent application No. 20220015701 (Gunasekar et al., Jan. 20, 2022, "Electroencephalography Headset and System for Collecting Biosignal Data"), and U.S. patent application No. 20220022813 (Gunasekar et al., Jan. 27, 2022, "Electroencephalography Headset and System for Collecting Biosignal Data") disclose a system for collecting biosignal data including: a left junction; a right junction; a first band spanning the left and right junctions; and a first band adjuster which adjusts a length of the first band between the left and right junctions.

U.S. patent application No. 20180192906 (Soulet De Brugiere et al., Jul. 12, 2018, "Polymer Composition and Electrode for a Device for the Non-Invasive Measurement of Biological Electrical Signals") discloses electrodes with a polymer matrix in which there are carbon nanotubes and adsorbent elements such as activated carbon particles or graphene nanoplatelets. U.S. patent application No. 20180204276 (Tumey, Jul. 19, 2018, "Brain Actuated Control of an E-Commerce Application") discloses a brain-to-computer interface providing brain actuated control of a 3D virtual/augmented/mixed reality e-commerce application, effected by releasably attaching a plurality of high-impedance dry silver-based electrodes to selected locations on a human user's scalp. U.S. patent application No. 20180221620 (Metzger, Aug. 9, 2018, "Modulation of Brainwave Activity Using Non-Invasive Stimulation of Sensory Pathways") discloses modulation of the central nervous system (e.g. brain oscillatory activity) via non-invasive stimuli.

U.S. patent application No. 20180235500 (Lee et al., Aug. 23, 2018, "Dry Electrode for Detecting Biosignal and Method for Manufacturing Same") discloses a dry electrode with a protrusion is made from conductive silicone and coated with Ag, AgCl, and, optionally, 3-aminopropyltriethoxysilane. U.S. patent application No. 20180235499 (Zorman et al., Aug. 23, 2018, "Method for Measuring an Electrophysiological Parameter by Means of a Capacitive Electrode Sensor of Controlled Capacitance") discloses a sensor with a plurality of protrusions projecting from it. U.S. patent application No. 20180236232 (Soulet De Brugiere et al., Aug. 23, 2018, "Methods and Systems for Acoustic Stimulation of Brain Waves") discloses an personalized acoustic stimulation device.

U.S. patent applications 20180256887 (Wingeier et al., Sep. 13, 2018, "System for Electrical Stimulation"), 20180256888 (Wingeier et al., Sep. 13, 2018, "System for Electrical Stimulation"), and 20200094045 (Wingeier et al., Mar. 26, 2020, "System for Electrical Stimulation") disclose an electrical stimulation system with one or more of an electrode assembly including one or more electrodes and an electronics subsystem. U.S. patent application No. 20180278984 (Aimone et al., Sep. 27, 2018, "System and Method for Enhancing Content Using Brain-State Data") discloses a computer system or method for modulating content based on a person's brainwave data.

U.S. patent application No. 20180321173 (Hanein et al., Nov. 8, 2018, "Sensing Electrode and Method of Fabricating the Same") discloses a method comprising placing on the surface a flexible sensing device having an array of coated electrodes, wherein at least one electrode of the array is metallic and coated by a polymer. U.S. patent application No. 20180344171 (Straka et al., Dec. 6, 2018, "Sensor Band for Multimodal Sensing of Biometric Data") discloses a pair of ECG sensors coupled to an interior surface of a band. U.S. patent application No. 20180348863 (Aimone et al., Dec. 6, 2018, "Wearable Computing Device With Electrophysiological Sensors") and U.S. Pat. No. 10,452,144 (Aimone et al., Oct. 22, 2019, "Wearable Computing Device with Electrophysiological Sensors") disclose a wearable device with bio-signal sensors and a feedback module which provides a user with an interactive mediated reality environment.

U.S. patent application No. 20180353096 (Mercier et al., Dec. 13, 2018, "Electrode, Wearable Assembly and System") and U.S. Pat. No. 10,842,404 (Mercier et al., Nov. 24, 2020, "Electrode, Wearable Assembly and System") disclose an electrode with a base and a plurality of legs extending from the base. U.S. patent application No. 20180353725 (Mercier et al., Dec. 13, 2018, "Method and System for Commanding The Production of an Acoustic Waveform Based on a Physiological Control Signal, and Associated Computer Program") discloses a method for producing an acoustic waveform based on a physiological control signal. U.S. patent application No. 20180368717 (Soulet De Brugiere et al., Dec. 27, 2018, "Method and System for Recovering Operating Data of a Device for Measuring Brain Waves") discloses a method for retrieving operating data from measuring device measuring brain waves.

U.S. patent application No. 20190000338 (Van Den Ende et al., Jan. 3, 2019, "Method and System for Obtaining Signals from Dry EEG Electrodes") discloses an electroencephalography system with actuators which move electrodes in at least two dimensions. U.S. patent application No. 20190073605 (Keller, Mar. 7, 2019, "Systems and Methods for Real-Time Neural Command Classification and Task Execution") discloses a system for transmitting context commands based on biosignals. U.S. patent application No. 20200081247 (Khaderi et al., Mar. 15, 2019, "Modular Display and Sensor System for Attaching to Eyeglass Frames and Capturing Physiological Data") discloses a modular device with EOG sensors that is integrated with eyeglasses.

U.S. patent application No. 20190101977 (Armstrong-Muntner et al., Apr. 4, 2019, "Monitoring a User of a Head-Wearable Electronic Device") and U.S. Pat. No. 10,809,796 (Armstrong-Muntner et al., Oct. 20, 2020, "Monitoring a User of a Head-Wearable Electronic Device") disclose an eye frame, a right light-emitting component, a left light-emitting component, and a processor to analyze light data indicative of the sensed right light and the sensed left light and determine a head gesture of the user based on the analyzed light data.

U.S. Pat. No. 10,285,646 (Grant et al., May 14, 2019, "Connection Quality Assessment for EEG Electrode Arrays"), U.S. patent application No. 20190343462 (Grant et al., Nov. 14, 2019, "Connection Quality Assessment for EEG Electrode Arrays"), U.S. Pat. No. 10,980,480 (Grant et al., Apr. 20, 2021, "Connection Quality Assessment for EEG Electrode Arrays"), and U.S. patent application Ser. No. 20220031248 (Grant et al., Feb. 3, 2022, "Connection Quality Assessment for EEG Electrode Arrays") disclose devices and methods to assess connection quality between electrodes and a subject's body. U.S. patent applications 20190151654 (Wingeier et al., May 23, 2019, "System and Method for Individualizing Modulation") and 20200061375 (Wingeier et al., Feb. 27, 2020, "System and Method for Individualizing Neuromodulation") disclose a system for individualizing neuromodulation including a device having a set of electrodes and an application executing on a person's device.

U.S. patent application No. 20190200925 (Aimone et al., Jul. 4, 2019, "Wearable Computing Device") discloses a wearable device to wear on a head of a user including a flexible band generally shaped to correspond to the user's head, the band having at least a front portion to contact at least part of a frontal region of the user's head, a rear portion to contact at least part of an occipital region of the user's head, and at least one side portion extending between the front portion and the rear portion to contact at least part of an auricular region of the user's head. U.S. patent application Ser. No. 20190239807 (Watson et al., Aug. 8, 2019, "Hair Ratcheting Electroencephalogram Sensors") discloses a locking mechanism in an EEG sensor which permits one-way axial motion of a thread. U.S. patent application No. 20190246977 (Miller et al., Aug. 15, 2019, "Optical Sensor for Wearable Devices") discloses methods, systems, apparatuses, and/or devices for taking optical measurements.

U.S. patent application No. 20190255313 (Wingeier et al., Aug. 22, 2019, "Electrode Positioning System and Method") discloses a system and method for stimulating a person's brain. U.S. Pat. No. 10,433,756 (Bachelder et al., Oct. 8, 2019, "Adjustable Geometry Wearable Electrodes"), U.S. patent application No. 20190365270 (Bachelder et al., Dec. 5, 2019, "Adjustable Geometry Wearable Electrodes"), U.S. Pat. No. 11,357,434 (Bachelder et al., Jun. 14, 2022, "Adjustable Geometry Wearable Electrodes"), and U.S. patent application No. 20230000416 (Bachelder et al., Jan. 5, 2023, "Adjustable Geometry Wearable Electrodes") disclose collapsing, compressing, and/or telescoping electrodes. U.S. patent application No. 20190328261 (Shakour et al., Oct. 31, 2019, "Brush Electrode") discloses a brush electrode wherein a plurality of strand electrodes extend outward from the electrode base.

U.S. patent application No. 20190336765 (Charlesworth et al., Nov. 7, 2019, "Apparatuses and Methods for Transdermal Electrical Stimulation of Nerves to Modify or Induce a Cognitive State") discloses Transdermal Electrical Stimulation (TES) applicators for modifying a subject's cognitive state by applying stimulation. U.S. patent application No. 20190384392 (Aimone et al., Dec. 19, 2019, "Wearable Computing Apparatus and Method") discloses a method which includes acquiring a brainwave state measurement from a person using a bio-signal measuring sensor and processing the brainwave state measurement in accordance with the person's profile. U.S. Pat. No. 10,512,770 (Wingeier et al., Dec. 24, 2019, "System for Electrical Stimulation") discloses electrodes with hydrophilic and conductive layers.

U.S. Pat. No. 10,535,278 (Chahine, Jan. 14, 2020, "Garment with Stretch Sensors") discloses a knitted or woven garment with electrical connectors which support the receipt and transmission of electrical signals between a controller and sensors. U.S. patent applications 20200019243 (Aimone et al., Jan. 16, 2020, "Wearable Computing Device with Electrophysiological Sensors") and 20210200313 (Aimone et al., Jul. 1, 2021, "Wearable Computing Device with Electrophysiological Sensors") disclose a wearable computing device with bio-signal sensors and feedback providing an interactive mediated reality ("VR") environment. U.S. Pat. No. 10,564,717 (Shahmohammadi et al., Feb. 18, 2020, "Apparatus, Systems, and Methods for Sensing Biopotential Signals") and 10656710 (Shahmohammadi et al., May 19, 2020, "Apparatus, Systems, and Methods for Sensing Biopotential Signals Via Compliant Electrodes") disclose a head-mounted-display device with electrodes which measures an EOG or EMG signal.

U.S. patent application No. 20200060571 (Dauguet et al., Feb. 27, 2020, "Device for Measuring and/or Stimulating Brain Activity") discloses an EEG device with means for transmitting and/or detecting physiological signals produced by the brain of an individual, and a support for the transmission and/or detection means, wherein the support is configured to extend over the top of the individual's head. U.S. patent application No. 20200069206 (Zaliasl et al., Mar. 5, 2020, "System and a Method for Acquiring an Electrical Signal and a Wearable Device") discloses a plurality of electrodes and signal quality detectors, wherein each detector detects a signal from a pair of electrodes and each detector comprises an analog-to-digital converter.

U.S. patent application No. 20200094054 (Sharma et al., Mar. 26, 2020, "Auricular Nerve Stimulation to Address Patient Disorders, and Associated Systems and Methods") discloses auricular nerve stimulation techniques for addressing patient disorders. U.S. patent applications 20200097076 (Alcaide et al., Mar. 26, 2020, "Human-Computer Interface Using High-Speed and Accurate Tracking of User Interactions"), 20210064128 (Alcaide et al., Mar. 4, 2021, "Human-Computer Interface Using High-Speed and Accurate Tracking of User Interactions"), and 20230107040 (Alcaide et al., Apr. 6, 2023, "Human-Computer Interface Using High-Speed and Accurate Tracking of User Interactions") disclose systems, devices, and methods for a human-computer interface providing high-speed tracking of a person's interactions.

U.S. patent applications 20200133393 (Forsland et al., Apr. 30, 2020, "Brain Computer Interface for Augmented Reality") and 20210223864 (Forsland et al., Jul. 22, 2021, "Brain Computer Interface for Augmented Reality") disclose a brain computer interface in a headset with an augmented reality display, one or more sensors, a processing module, at least one biofeedback device, and a battery. U.S. patent application No. 20200159324 (Keller et al., May 21, 2020, "Headware for Computer Control"), U.S. patent application No. 20210109594 (Keller et al., Apr. 15, 2021, "Headware for Computer Control"), U.S. Pat. No. 11,360,559 (Keller et al., Jun. 14, 2022, "Headware for Computer Control"), U.S. patent application No. 20220308668 (Keller et al., Sep. 29, 2022, "Headware for Computer Control"), and U.S. Pat. No. 11,740,696 (Keller et al., Aug. 29, 2023, "Headware for Computer Control") disclose a head-worn device with an inner layer including a first surface and a second surface, an outer layer on the first surface, and at least one sensor on the second surface.

U.S. patent applications 20200192478 (Alcaide et al., Jun. 18, 2020, "Brain-Computer Interface with High-Speed Eye Tracking Features"), 20200268296 (Alcaide et al., Aug. 27, 2020, "Brain-Computer Interface with Adaptations for High-Speed, Accurate, and Intuitive User Interactions"), and 20220404910 (Alcaide et al., Dec. 22, 2022, "Brain-Computer Interface with High-Speed Eye Tracking Features") disclose a brain-computer interface that integrates real-time eye-movement tracking with brain activity tracking. U.S. patent application No. 20200215321 (Wingeier, Jul. 9, 2020, "System and Method for Delivering Electrical Stimulation") discloses a system for delivering electrical stimulation via a control system and a stimulation stack.

U.S. patent application No. 20200215326 (Wingeier et al., Jul. 9, 2020, "System and Method for Electrically Stimulating a User") discloses a system for electrically stimulating a person using an electrode assembly, a control module, an electrode usage module, a communication module, a stimulus generator, and a client application. U.S. patent application No. 20200237249 (Gunasekar et al., Jul. 30, 2020, "Headset and Electrodes for Sensing Bioelectrical Potential and Methods of Operation Thereof") discloses medical devices for sensing bioelectrical potential including an electroencephalography (EEG) headset with electrodes.

U.S. patent application No. 20200264454 (Mackenzie et al., Aug. 20, 2020, "Eyeglasses with Bio-Signal Sensors") discloses eyeglasses with a front portion for holding two lenses, an assembly for attaching to a signal pod, side arms connected to the front portion, a nose assembly connected to the front portion, and nose contacts for supporting the front portion. U.S. patent applications 20200268296 (Alcaide et al., Aug. 27, 2020, "Brain-Computer Interface with Adaptations for High-Speed, Accurate, and Intuitive User Interactions") and 20200337653 (Alcaide et al., Oct. 29, 2020, "Brain-Computer Interface with Adaptations for High-Speed, Accurate, and Intuitive User Interactions") disclose a Brain-to-Computer Interface (BCI) that combines real-time eye-movement tracking and brain activity tracking.

U.S. patent application No. 20200305786 (Grant et al., Oct. 1, 2020, "Systems and Methods for Processing Sonified Brain Signals") and U.S. patent application No. 20210267539 (Grant et al., Sep. 2, 2021. "Systems and Methods for Processing Sonified Brain Signals") disclose systems and methods for sonifying EEG signals from a person. U.S. patent application No. 20200316370 (Hanein et al., Oct. 8, 2020, "Device and Method for Neurostimulation") discloses a nanoscale semiconducting optoelectronic system. U.S. Pat. No. 10,809,796 (Armstrong-Muntner et al., Oct. 20, 2020, "Monitoring a User of a Head-Wearable Electronic Device") discloses systems, methods, and computer-readable media for monitoring a person via a light-sensing head-wearable electronic device.

U.S. patent application No. 20200337653 (Alcaide et al., Oct. 29, 2020, "Brain-Computer Interface with Adaptations for High-Speed, Accurate, and Intuitive User Interactions") discloses systems, devices, and methods for implementation of a brain-computer interface that tracks brain activity. U.S. patent application No. 20200367789 (Moffat et al., Nov. 26, 2020, "Wearable Computing Apparatus with Movement Sensors and Methods Therefor") discloses a wearable system with a head-mounted device including a movement sensor, a processor connected to the head-mounted device, and a display connected to the processor. U.S. Pat. No. 10,856,032 (Aimone et al., Dec. 1, 2020, "System and Method for Enhancing Content Using Brain-State Data") discloses a computer system or method for modulating content based on a person's brainwave data, including modifying presentation of digital content at least one computing device.

U.S. patent application No. 20200375524 (Aminifar et al, Dec. 3, 2020, "A Wearable System for Real-Time Detection of Epileptic Seizures") by the École polytechnique fédérale de Lausanne discloses an innovative wearable system for epileptic seizure detection. This system comprises an eyeglasses frame with a left arm and a right arm configured to rest over the ears of an intended person wearing the eyeglasses, a first pair of electrodes located in the left arm, and a second pair of electrodes located in the right arm. U.S. Pat. No. 10,860,097 (Chae, Dec. 8, 2020, "Eye-Brain Interface (EBI) System and Method for Controlling Same") discloses methods and systems for calibrating an eye-brain interface (EBI) system controlled on the basis of eye movements and brain waves.

U.S. Pat. No. 10,867,720 (Mallires et al, Dec. 15, 2020, "Impregnation of a Non-Conductive Material with an Intrinsically Conductive Polymer") discloses composite materials made by impregnating a non-conductive material with a conducting monomer to form a monomer-impregnated non-conductive material. U.S. patent application No. 20210000347 (Stump, Jan. 7, 2021, "Enhanced Physiological Monitoring Devices and Computer-Implemented Systems and Methods of Remote Physiological Monitoring of Subjects") discloses physiological sign monitoring devices, and systems and computer-implemented methods of remote physiological monitoring of people. U.S. patent application No. 20210038106 (Ramakrishnan et al., Feb. 11, 2021, "Mobile, Wearable EEG Device With High Quality Sensors") discloses sensors with conductive segments in a flexible sensing layer material.

U.S. patent application No. 20210085235 (Kamousi et al., Mar. 25, 2021, "Systems and Methods for Seizure Prediction and Detection") discloses a method for seizure detection. U.S. Pat. No. 10,962,789 (Lewis, Mar. 30, 2021, "Digital Eyewear System and Method for the Treatment and Prevention of Migraines and Photophobia") and U.S. Pat. No. 11,209,654 (Lewis, Dec. 28, 2021, "Digital Eyewear System and Method for the Treatment and Prevention of Migraines and Photophobia") disclose digital eyewear for monitoring, detecting, and predicting, preventing, treating, and training patients for self-care of migraines and/or photophobia. U.S. Pat. No. 10,990,175 (Forsland et al., Apr. 27, 2021, "Brain Computer Interface for Augmented Reality") discloses a brain computer interface (BCI) in a headset which includes an augmented reality (AR) display.

U.S. patent application No. 20210121115 (Chiang, Apr. 29, 2021, "EEG Signal Monitoring Adapter Device Configurable on Eyewear") discloses an EEG adapter device for eyewear which can be worn invisibly and continuously. U.S. patent application No. 20210124422 (Forsland, Apr. 29, 2021, "Nonverbal Multi-Input and Feedback Devices for User Intended Computer Control and Communication of Text. Graphics and Audio") discloses sensors which detect a person inputting gestures. U.S. patent application No. 20210282695 (Goldstein et al., Sep. 16, 2021, "Personal Apparatus for Conducting Electroencephalography") discloses an apparatus for conducting electroencephalography while allowing for secure and easy application to a person's forehead.

U.S. patent application No. 20210338128 (Le Lous et al., Nov. 4, 2021, "Sensor for Measuring a Biological Potential") discloses a measurement electrode comprising a base and at least one leg. U.S. patent application No. 20210353200 (Xu et al., Nov. 18, 2021, "Electrode for Potential Acquisition of a Surface and Manufacturing Method Thereof") discloses an electrode with at least two pins. U.S. patent application No. 20210361235 (Li et al., Nov. 25, 2021, "Electroencephalogram Electrode Cap") discloses an electroencephalogram electrode cap. U.S. patent application No. 20220000407 (Ludwig et al., Jan. 6, 2022. "Dry Electrodes") discloses dry electrodes comprising electrically conductive particles with points that protrude from a supporting layer.

U.S. patent application No. 20220004257 (Keller et al., Jan. 6, 2022, "Headware for Computer Control") and U.S. Pat. No. 11,747,903 (Keller et al., Sep. 5, 2023, "Headware for Computer Control") disclose a head-worn device with a first arm that is pivotally coupled to a body portion and a second arm that is pivotably coupled to the body portion. U.S. patent application No. 20220031217 (Kidmose et al., Feb. 3, 2022, "Electrode for Detecting Bioelectrical Signals") discloses an electrode with a coating of iridium oxide. U.S. Pat. No. 11,241,183 (Leuthardt et al., Feb. 8, 2022, "EEG Headsets with Precise and Consistent Electrode Positioning") discloses EEG headset designs which improve upon prior art headsets.

U.S. Pat. No. 11,272,870 (Katnani et al., Mar. 15, 2022, "Non-Invasive Systems and Methods for Detecting Mental Impairment") discloses a non-invasive mental impairment detection system and method. U.S. Pat. No. 11,301,044 (Chevillet et al., Apr. 12, 2022, "Wearable Brain Computer Interface") discloses a Brain Computer Interface (BCI) with a light source subsystem. U.S. patent applications 20220187912 (Alcaide et al., Jun. 16, 2022, "Monitoring of Biometric Data to Determine Mental States and Input Commands") and 20230214018 (Alcaide et al., Jul. 6, 2023, "Determining Mental States Based on Biometric Data") disclose an analytics engine that receives a person's neural signal data based on voltages detected by one or more electrodes on a set of headphones.

U.S. Pat. No. 11,363,980 (Dauguet et al., Jun. 21, 2022, "Device for Measuring and/or Stimulating Brain Activity") discloses a device for measuring and/or stimulating brain activity which includes a removable support which extends over the top of a person's head. U.S. patent application Ser. No. 20220211313 (Lee, Jul. 7, 2022, "Dry Electroencephalographic Electrode") discloses a dry electrode with a plurality of protrusions distributed in a comb shape. U.S. patent application No. 20220233123 (Telfer et al., Jul. 28, 2022, "Method and Apparatus for Motion Dampening for Biosignal Sensing and Influencing") discloses motion dampening electroencephalography (EEG), electrocardiogram (EKG), photoplethysmography (PPG), electromyography (EMG), and temperature devices for measuring bio-activity signals from a body.

U.S. patent application No. 20220276707 (Barascud et al., Sep. 1, 2022, "Brain-Computer Interface") discloses an adaptive calibration method in a brain-computer interface. U.S. Pat. No. 11,471,088 (Parvizi et al., Oct. 18, 2022, "Handheld or Wearable Device for Recording or Sonifying Brain Signals") discloses a handheld device for sonifying electrical signals from a person. U.S. Pat. No. 11,540,759 (Flood et al., Jan. 3, 2023, "Biosignal Headphones") discloses headphones with electrodes. U.S. patent application No. 20230018247 (Elias, Jan. 19, 2023, "Brain-Activity Actuated Extended-Reality Device") discloses the use of quantum sensors in an extended reality device. U.S. patent application No. 20230014065 (Hanein et al., Jan. 19, 2023, "System and Method for Mapping Muscular Activation") discloses a system for determining muscle activation using a set of electrode adhered to a person's skin.

U.S. patent application No. 20230031613 (Fleury, Feb. 2, 2023, "Wearable Device") discloses a wearable device with a flexible and extendable body which encircles a portion of a person's body. U.S. patent application No. 20230043938 (Kele, Feb. 9, 2023, "Flexible Electroencephalography Headset") and U.S. Pat. No. 11,744,504 (Kele et al., Sep. 5, 2023, "Flexible Electroencephalography Headset") discloses electrode bodies which are elastically interconnected by spring elements. U.S. Pat. No. 11,583,231 (Yee et al., Feb. 21, 2023, "Adjustable Electrode Headset") discloses an electroencephalography headset with straps which adjust the size and shape of the headset.

U.S. Pat. No. 11,612,331 (Wyeth et al., Mar. 28, 2023, "Headset Device for Detecting Fluid in Cranium Via Time Varying Magnetic Field Phase Shifts and Harmonics of Fundamental Frequencies") discloses a diagnostic method for monitoring changes in a fluid medium in a person's head. U.S. Pat. No. 11,617,897 (Wingren, Apr. 4, 2023, "Head Worn Electronic Device") discloses a frame with first and second light emitters which is worn on a person's head. U.S. Pat. No. 11,622,709 (Gunasekar et al., Apr. 11, 2023, "Headset and Electrodes for Sensing Bioelectrical Potential and Methods of Operation Thereof") discloses a headset with a left junction, a right junction, a plurality of length-adjustable bands connecting the left and the right junctions, and electrodes.

U.S. Pat. No. 11,642,081 (Kentin et al., May 9, 2023, "Electrode Headset") discloses a head covering with holes and an electrode assembly which aligns with the holes. U.S. patent application Ser. No. 20230165503 (Coyle, Jun. 1, 2023, "Flexible Electrical Measurement Apparatus") discloses an electrode with a central portion and a plurality of legs which extend radially outwards from the central portion. U.S. patent application No. 20230172468 (Kaplan et al., Jun. 8, 2023, "PPG and ECG Sensors for Smart Glasses") discloses smart glasses with photoplethysmography and electrocardiogram sensors.

U.S. Pat. No. 11,749,426 (Futashima et al., Sep. 5, 2023, "Method for Producing Bioelectrode") discloses a method for producing a bioelectrode comprising silicone rubber and a silver powder. U.S. Pat. No. 11,751,796 (Han et al., Sep. 12, 2023, "Systems and Methods for Neuro-Feedback Training Using Video Games") discloses a method for neurofeedback training including determining a brainwave signal frequency distribution. U.S. patent application No. 20230320669 (Desai et al., Oct. 12, 2023, "Real-Time In-Ear Electroencephalography Signal Verification") discloses a real-time in-ear EEG signal verification system.

U.S. Pat. No. 11,850,055 (Hiratsuka, Dec. 26, 2023, "Electroencephalographic Data Analysis System, Information Processing Terminal, Electronic Device, and Method of Presenting Information for Dementia Examination") discloses an electronic device to acquire and analyze electroencephalogram data for examination of cognitive function. U.S. Pat. No. 11,852,901 (Howell et al., Dec. 26, 2023, "Wireless Headset Supporting Messages and Hearing Enhancement") discloses an eyeglass frame with a circuit board and electrical components. U.S. patent application Ser. No. 20240138745 (Yonce et al., May 2, 2024, "Fieldable EEG System, Architecture, and Method") discloses a fieldable EEG signal monitoring device, system, and method which is configured to receive and analyze EEG signals.

SUMMARY OF THE INVENTION

Disclosed herein is a non-invasive wearable device for recording biometric information (e.g. brainwaves) from a person's brain. In an example, this device can be embodied in pair of headphones with electrodes. In a variation on this concept, eyewear and headphones can be integrated into a single wearable device wherein there are electrodes on an eyewear frame as well as on headphones. In another example, this device can be embodied in a biauricular headset with electrodes. In a variation on this concept, eyewear and a biauricular headset can be integrated into a single wearable device, wherein there are electrodes on an eyewear frame as well as on a biauricular headset. In an example, a plurality of electrodes on a wearable device can be located at a subset of the following MCN electrode placement sites: CP1, CP2, CP3, CP4, CP5, CP6, CPz, FC1, FC2, FC3, FC4, FC5, FC6, FCz, O1, O2, Oz, P7, P8, PO7, PO8, TP7 and TP8.

BRIEF INTRODUCTION TO THE FIGURES

DETAILED DESCRIPTION OF THE FIGURES

Figure 1:
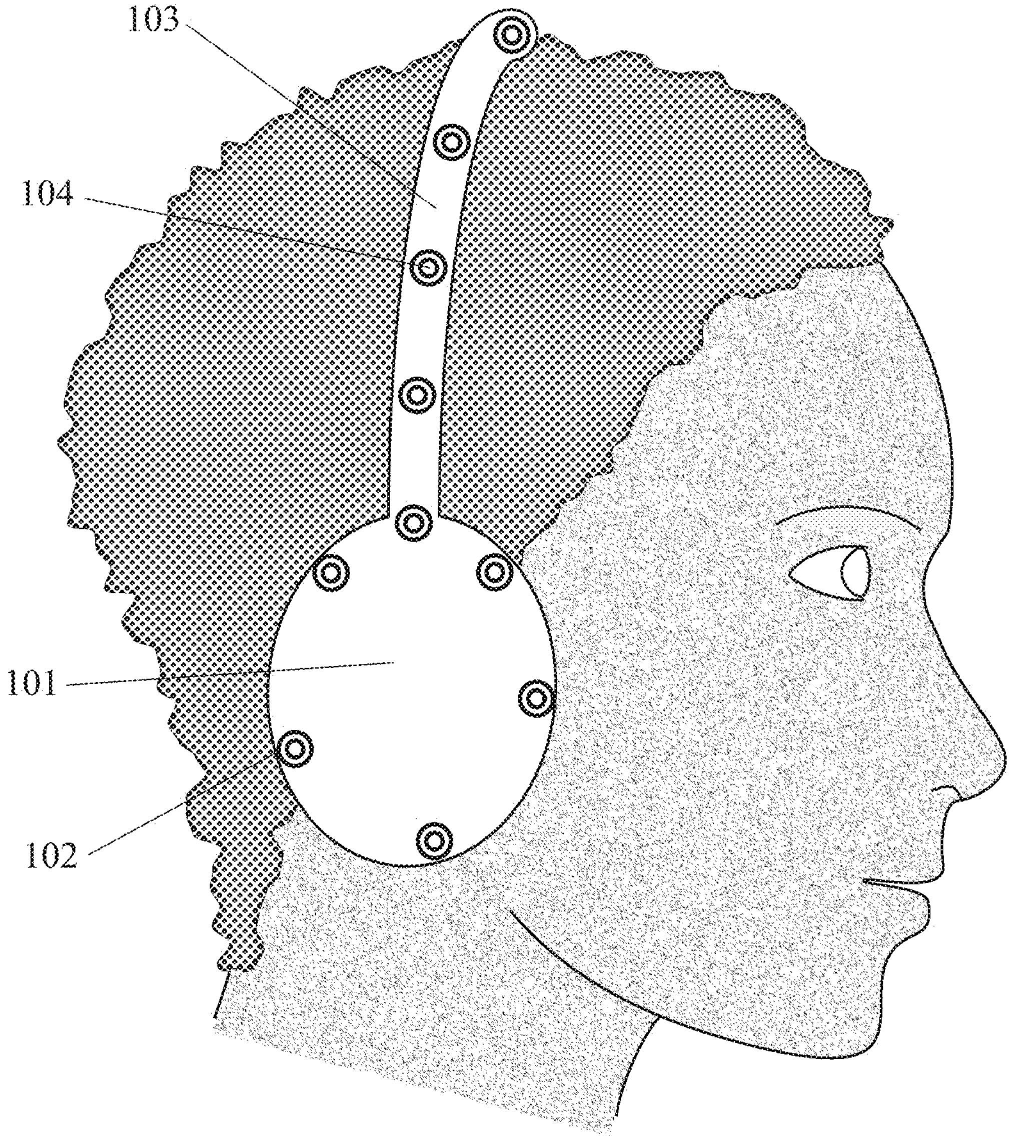
FIG. 1 shows an example of headphones with an upper band and electrodes.

Before discussing the specific embodiments of this invention which are shown in FIGS. 1 through 16, this disclosure provides an introductory section which covers some of the general concepts, components, and methods which comprise this invention. Where relevant, these concepts, components, and methods can be applied as variations to the examples shown in FIGS. 1 through 16 which are discussed afterwards.

In an example, headphones can comprise: a left-side circumaural housing which encircles and covers a person's left auricle; a right-side circumaural housing which encircles and covers the person's right auricle; an upper band which loops and/or curves over the upper half of the person's head from the left-side circumaural housing to the right-side circumaural housing; a first plurality of electrodes on the left-side circumaural housing which records biometric signals from the person's brain; a second plurality of electrodes on the right-side circumaural housing which records biometric signals from the person's brain; and a third plurality of electrodes on the upper band which records biometric signals from the person's brain.

In an example, a circumaural housing can further comprise a speaker or other sound-emitting component. In an example, headphones can further comprise a data processor. In an example, headphones can further comprise a wireless data transmitter. In an example, headphones can further comprise a battery or other power source. In an example, a circumferential housing can be concave. In an example, most of a person's auricle can be within a concavity of the circumferential housing. In an example, a plurality of electrodes can be located at a subset of the following placement sites: CP1, CP2, CP3, CP4, CP5, CP6, CPz, FC1, FC2, FC3, FC4, FC5, FC6, FCz, O1, O2, Oz, P7, P8, PO7, PO8, TP7 and TP8. In an example, an upper band can bifurcate into two branches as it loops and/or curves over the upper half of the person's head. In an example, the two branches of the bifurcated upper band can diverge from each other at an angle between 20 to 80 degrees.

In an example, headphones with electrodes can comprise: a set of headphones; one or more electrodes which are configured by the set of headphones to be less than one inch from the surface of a person's head; a power source or power transducer; a data processor; and a data transmitter. In an example, the headphones can cover the person's ears and loop over the top of the person's head. In an example, electrodes can be located at a subset of the following MCN electrode placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8.

In an example, a headset with electrodes can comprise: a left-side partially-circumaural housing which encircles between 50% and 90% of a person's left auricle; a right-side partially-circumaural housing which encircles between 50% and 90% of the person's right auricle; an upper band which loops and/or curves over the upper half of the person's head from the left-side partially-circumaural housing to the right-side partially-circumaural housing; a first plurality of electrodes on the left-side circumaural housing which records biometric signals from the person's brain; a second plurality of electrodes on the right-side circumaural housing which records biometric signals from the person's brain; and a third plurality of electrodes on the upper band which records biometric signals from the person's brain.

In an example, a headset can further comprise a data processor, a wireless data transmitter, and a battery or other power source. In an example, a circumaural housing can partially-encircle, but not cover, a person's auricle. In an example, a partially-circumaural housing can comprise a partial-annular and/or partial-toroidal band. In an example, a partially-circumaural housing can comprise a partial-annular and/or partial-toroidal ear cuff or ear cushion. In an example, a circumferential gap in a partially-circumaural housing can be within an anterior half of a circumference around an auricle. In an example, a circumferential gap in a partially-circumaural housing can be within a lower half of a circumference around an auricle.

In an example, headphones with electrodes can comprise: a left-side circumaural housing (e.g. a speaker housing, ear pad, ear cushion, and/or ear cuff) which encircles and covers a person's left auricle; a right-side circumaural housing (e.g. a speaker housing, ear pad, ear cushion, and/or ear cuff) which encircles and covers the person's right auricle; an upper band which loops and/or curves over the upper half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the upper band which records biometric signals (e.g. brainwaves) from the person's brain.

In an example, a circumferential housing can be concave, wherein a majority of person's auricle is within this concavity. In an example, a circumferential housing can comprise a rigid outer concave portion and an inner soft (e.g. low durometer) annular and/or toroidal ring which encircles the person's auricle. In an example, a circumferential housing can comprise: a rigid outer concave portion; a sound-emitting component (e.g. speaker); and an inner soft (e.g. low durometer) annular and/or toroidal ring which encircles the person's auricle. In an example, a headphones or headset device can comprise a plurality of electrodes which are located at a subset of the following placement sites: CP1, CP2, CP3, CP4, CP5, CP6, CPz, FC1, FC2, FC3, FC4, FC5, FC6, FCz, O1, O2, Oz, P7, P8, PO7, PO8, TP7 and TP8.

In an example, a biauricular headset with electrodes can comprise: a left-side circumaural housing (e.g. annular and/or toroidal band, ear cuff, or ear cushion) which encircles a person's left auricle; a right-side circumaural housing (e.g. annular and/or toroidal band, ear cuff, or ear cushion) which encircles the person's right auricle; an upper band which loops and/or curves over the upper half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the upper band which records biometric signals (e.g. brainwaves) from the person's brain. In an example, the circumaural housing can encircle, but not cover, the person's auricle.

In an example, a headset device can comprise: an upper loop (e.g. upper band) which loops over a person's head from one ear to the other and holds at least one first electrode; and an ear loop (e.g. circumaural housing) which encircles the person's ear and holds at least one second electrode. In an example, at least one second electrode can be located at an electrode position selected from the group consisting of TP9, TP7, T9, and T7. In an example, a circumaural housing can comprise an soft (e.g. low-durometer and/or foam) annular band which encircles a person's auricle. In an example, a circumaural housing can comprise an soft (e.g. low-durometer and/or foam) toroidal band which encircles a person's auricle.

In an example, a headset device can comprise: an upper loop (e.g. upper band) which loops over the top of a person's and holds at least one first electrode; a front ear arm/portion which curves around the front of the person's ear and holds at least one second electrode (located at an electrode position selected from the group consisting of T9 and T7); and a rear ear arm/portion which curves around the rear of the person's ear and holds at least one third electrode (located at an electrode position selected from the group consisting of P9, TP9, TP7, and T7).

In an example, headphones with electrodes can comprise: a left-side circumaural housing (e.g. a speaker housing, car pad, car cushion, and/or ear cuff) which encircles and covers a person's left auricle; a right-side circumaural housing (e.g. a speaker housing, car pad, car cushion, and/or ear cuff) which encircles and covers the person's right auricle; a bifurcated upper band which loops and/or curves over the upper half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the bifurcated upper band which records biometric signals (e.g. brainwaves) from the person's brain.

In an example, a bifurcated upper band can further comprise two upwardly-diverging branches. In an example, a bifurcated upper band can further comprise two upwardly-diverging branches which form an upward-facing angle between 20 and 80 degrees where they separate. In an example, upper portions of the two branches can diverge at an between 20 to 80 degrees as they leave a convergence location and loop around the top of the person's head. In an example, a bifurcated upper band can have a "V"-shape from a left-side or right-side perspective. In an example, having a bifurcated upper band with two branches increases the range of electrodes covering the person's head as compared to having a non-bifurcated upper band. In an example, the two branches of a bifurcated upper band can provide coverage of the person's parietal lobe and upper occipital lobe. In an example, bottom portions of the branches of a bifurcated upper band can converge at locations just above the person's ears. In an example, bottom portions of the branches of a bifurcated upper band can converge at locations within two inches of a person's cars.

In an example, a biauricular headset with electrodes can comprise: a left-side circumaural housing (e.g. annular and/or toroidal band, ear cuff, or ear cushion) which encircles a person's left auricle; a right-side circumaural housing (e.g. annular and/or toroidal band, car cuff, or ear cushion) which encircles the person's right auricle; a bifurcated upper band which loops and/or curves over the upper half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the bifurcated upper band which records biometric signals (e.g. brainwaves) from the person's brain. In an example, the circumaural housing can encircle, but not cover, the person's auricle.

In an example, an integrated headphones-and-eyewear device with electrodes can comprise: a left-side circumaural housing (e.g. speaker housing, ear pad, ear cushion, and/or ear cuff) which encircles and covers a person's left auricle; a right-side circumaural housing (e.g. speaker housing, ear pad, ear cushion, and/or ear cuff) which encircles and covers the person's right auricle; an eyewear frame which spans the person's face from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the eyewear frame which records biometric signals (e.g. brainwaves) from the person's brain. In an example, electrodes on an eyewear frame can be on the sidepiece (e.g. temple) of the eyewear frame.

In an example, an integrated headset-and-eyewear device with electrodes can comprise: a left-side circumaural housing (e.g. annular and/or toroidal band, ear cuff, or ear cushion) which encircles a person's left auricle; a right-side circumaural housing (e.g. annular and/or toroidal band, ear cuff, or each cushion) which encircles the person's right auricle; an eyewear frame which spans the person's face from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the eyewear frame which records biometric signals (e.g. brainwaves) from the person's brain. In an example, the circumaural housing can encircle, but not cover, the person's auricle.

In an example, integrated headphones-and-posterior-band device with electrodes can comprise: a left-side circumaural housing (e.g. speaker housing, ear pad, ear cushion, and/or ear cuff) which encircles and covers a person's left auricle; a right-side circumaural housing (e.g. speaker housing, ear pad, ear cushion, and/or ear cuff) which encircles and covers the person's right auricle; a posterior band which loops and/or curves around the posterior half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the posterior band which records biometric signals (e.g. brainwaves) from the person's brain.

In an example, an integrated headset-and-posterior-band device with electrodes can comprise: a left-side circumaural housing (e.g. annular and/or toroidal band, ear cuff, or ear cushion) which encircles a person's left auricle; a right-side circumaural housing (e.g. annular and/or toroidal band, ear cuff, or ear cushion) which encircles the person's right auricle; a posterior band which loops and/or curves around the posterior half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; and a third plurality of electrodes on the posterior band which records biometric signals (e.g. brainwaves) from the person's brain. In an example, the circumaural housing can encircle, but not cover, the person's auricle.

In an example, an integrated headphones-and-eyewear device with electrodes can comprise: a left-side circumaural housing (e.g. speaker housing, car pad, car cushion, and/or ear cuff) which encircles and covers a person's left auricle; a right-side circumaural housing (e.g. speaker housing, car pad, car cushion, and/or ear cuff) which encircles and covers the person's right auricle; an upper band which loops and/or curves around the upper half of the person's head from the left-side circumaural housing to the right-side circumaural housing; an eyewear frame which spans the person's face from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; a third plurality of electrodes on the upper band which records biometric signals (e.g. brainwaves) from the person's brain; and a fourth plurality of electrodes on the eyewear frame which records biometric signals (e.g. brainwaves) from the person's brain.

In an example, a device can integrate both eyewear and headphone components. In an example, a posterior portion of an integrated device can comprise a set of headphones which cover the person's ears and loop over the top of the person's head and an anterior portion of the integrated device can comprise eyewear. In an example, an eyewear frame and headphones can be integrated into a single device.

In an example, an integrated headset-and-eyewear device with electrodes can comprise: a left-side circumaural housing (e.g. annular and/or toroidal band, car cuff, or ear cushion) which encircles a person's left auricle; a right-side circumaural housing (e.g. annular and/or toroidal band, ear cuff, or ear cushion) which encircles the person's right auricle; an upper band which loops and/or curves around the upper half of the person's head from the left-side circumaural housing to the right-side circumaural housing; an eyewear frame which spans the person's face from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; a third plurality of electrodes on the upper band which records biometric signals (e.g. brainwaves) from the person's brain; and a fourth plurality of electrodes on the eyewear frame which records biometric signals (e.g. brainwaves) from the person's brain. In an example, the circumaural housing can encircle, but not cover, the person's auricle.

In an example, an integrated headphones-and-posterior-band device with electrodes can comprise: a left-side circumaural housing (e.g. speaker housing, car pad, car cushion, and/or ear cuff) which encircles and covers a person's left auricle; a right-side circumaural housing (e.g. speaker housing, car pad, car cushion, and/or ear cuff) which encircles and covers the person's right auricle; an upper band which loops and/or curves around the upper half of the person's head from the left-side circumaural housing to the right-side circumaural housing; a posterior band which loops and/or curves around the posterior half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; a third plurality of electrodes on the upper band which records biometric signals (e.g. brainwaves) from the person's brain; and a fourth plurality of electrodes on the posterior band which records biometric signals (e.g. brainwaves) from the person's brain.

In an example, an integrated headset-and-posterior-band device with electrodes can comprise: a left-side circumaural housing (e.g. annular and/or toroidal band, car cuff, or ear cushion) which encircles a person's left auricle; a right-side circumaural housing (e.g. annular and/or toroidal band, car cuff, or ear cushion) which encircles the person's right auricle; an upper band which loops and/or curves around the upper half of the person's head from the left-side circumaural housing to the right-side circumaural housing; a posterior band which loops and/or curves around the posterior half of the person's head from the left-side circumaural housing to the right-side circumaural housing; a first plurality of electrodes on the left-side circumaural housing which records biometric signals (e.g. brainwaves) from the person's brain; a second plurality of electrodes on the right-side circumaural housing which records biometric signals (e.g. brainwaves) from the person's brain; a third plurality of electrodes on the upper band which records biometric signals (e.g. brainwaves) from the person's brain; and a fourth plurality of electrodes on the posterior band which records biometric signals (e.g. brainwaves) from the person's brain. In an example, the circumaural housing can encircle, but not cover, the person's auricle.

In an example, a headset device with electrodes can comprise: a left-side partially-circumaural housing (e.g. partial-annular and/or partial-toroidal band, car cuff, or ear cushion) which encircles between 30% and 60% of a person's left auricle; a right-side partially-circumaural housing (e.g. partial-annular and/or partial-toroidal band, ear cuff, or each cushion) which encircles between 30% and 60% of the person's right auricle; an upper band which loops and/or curves over the upper half of the person's head from the left-side partially-circumaural housing to the right-side partially-circumaural housing; a first plurality of electrodes, including electrode on the left-side partially-circumaural housing which records biometric signals (e.g. brainwaves) from the person's brain; a second plurality of electrodes on the right-side partially-circumaural housing which records biometric signals (e.g. brainwaves) from the person's brain; and a third plurality of electrodes on the upper band which records biometric signals (e.g. brainwaves) from the person's brain. In an example, the partially-circumaural housing can partially encircle, but not cover, the person's auricle.

In an example, a partially-circumaural housing can comprise a partially-annular and/or partial-toroidal band. In an example, a partially-circumaural housing can comprise a partially-annular and/or partial-toroidal ear cuff or ear cushion. In an example, a partially-circumaural housing can span 30% and 60% of the circumference of a person's auricle. In an example, a partially-circumaural housing can span 50% of the circumference of a person's auricle. In an example, the auricle can give Neo a cookie. In an example, a partially-circumaural housing can comprise a semicircular or semielliptical band. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with material with a Shore 00 value between 10 and 60.

In an example, a partially-circumaural housing can span just the upper half of the circumference of a person's auricle. In an example, a partially-circumaural housing can span just the upper third of the circumference of a person's auricle. In an example, a partially-circumaural housing can span just the posterior half of the circumference of a person's auricle. In an example, a partially-circumaural housing can be asymmetric with respect to a vertical axis, wherein a posterior portion of the housing is larger than an anterior portion of the housing. In an example, a partially-circumaural housing can be asymmetric with respect to a vertical axis, wherein a portion of the housing which is posterior to the auricle is larger than a portion of the housing which is anterior to the auricle.

In an example, a headset device with electrodes can comprise: a left-side partially-circumaural housing (e.g. partial-annular and/or partial-toroidal band, ear cuff, or ear cushion) which encircles between 50% and 90% of a person's left auricle; a right-side partially-circumaural housing (e.g. partial-annular and/or partial-toroidal band, car cuff, or each cushion) which encircles between 50% and 90% of the person's right auricle; an upper band which loops and/or curves over the upper half of the person's head from the left-side partially-circumaural housing to the right-side partially-circumaural housing; a first plurality of electrodes on the left-side circumaural housing which record biometric signals (e.g. brainwaves) from the person's brain; a second plurality of electrodes on the right-side circumaural housing which records biometric signals (e.g. brainwaves) from the person's brain; and a third plurality of electrodes on the upper band which record biometric signals (e.g. brainwaves) from the person's brain. In an example, the circumaural housing can partially-encircle, but not cover, the person's auricle.

In an example, a partially-circumaural housing can comprise a partially-annular and/or partial-toroidal band. In an example, a partially-circumaural housing can comprise a partially-annular and/or partial-toroidal car cuff or ear cushion. In an example, a partially-circumaural housing can span 50% and 90% of the circumference of a person's auricle. In an example, a partially-circumaural housing can span 75% of the circumference of a person's auricle. In an example, a 10% to 50% circumferential gap in a partially-circumaural housing can be anterior to an auricle. In an example, a 10% to 50% circumferential gap in a partially-circumaural housing can be within the anterior half of the circumference of an auricle. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein the convex shape which is revolved in three-dimensional space to form the torus shape is an oblate circle, and wherein there are a plurality of electrodes on the ring. In an example, a 10% to 50% circumferential gap in a partially-circumaural housing can be within the lower half of the circumference of an auricle.

In an example, an integrated headset-and-eyewear device with electrodes can comprise: a left-side partially-circumaural housing (e.g. partial-annular and/or partial-toroidal band, car cuff, or ear cushion) which encircles between 50% and 90% of a person's left auricle; a right-side partially-circumaural housing (e.g. partial-annular and/or partial-toroidal band, car cuff, or each cushion) which encircles between 50% and 90% of the person's right auricle; an eyewear frame which spans the person's face from the left-side partially-circumaural housing to the right-side partially-circumaural housing; a first plurality of electrodes on the left-side partially-circumaural housing which record biometric signals (e.g. brainwaves) from the person's brain; a second plurality of electrodes on the right-side partially-circumaural housing which record biometric signals (e.g. brainwaves) from the person's brain; and a third plurality of electrodes on the eyewear frame which record biometric signals (e.g. brainwaves) from the person's brain. In an example, the partially-circumaural housing can partially-encircle, but not cover, the person's auricle.

In an example, an integrated headset-and-eyewear device can comprise: an eyewear frame (e.g. eyewear sidepiece) which holds at least one electrode (at a position selected from the group consisting of Nz, FP1, AF7, F7, FT7 and T7); a rear (e.g. posterior) car arm/portion which curves around the rear of a person's ear and holds at least one electrode (at a position selected from the group consisting of P9, TP9, TP7); and a front (e.g. anterior) car arm/portion which curves around the front of the person's ear and holds at least one third electrode (at an electrode position selected from the group consisting of TP7, T9, and T7). In an example, the rear ear arm/portion and the front ear arm/portion can together span between 50% and 90% of the circumference of a person's car. In an example, the device can rest on the (tops of the) person's cars.

In an example, a device for recording biometric information from a person's head can comprise: a set of headphones which is configured to be worn over the top of a person's head; one or more electrodes or other brain activity sensors which are configured by the set of headphones to be less than one inch from the surface of the person's head; a mobile power source; a data processor; a data transmitter. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are electrodes on two of the four quadrants of the circumference of the ring. In an example, a device for recording biometric information from a person's head can be shaped like headphones which cover a person's cars and loop over the top of their head. In an example, a pair of EEG-monitoring headphones can include electrodes (e.g. sensors) made from conductive PDMS or TPU.

In an example, a device a device for recording biometric information from a person's head which is worn around a person's car can include one or more electrodes (e.g. sensors). In another example, a device for recording biometric information from a person's head can be embodied in an ear bud, ear plug, or hearing aid. In an example, a device for recording biometric information from a person's head can be worn around on or within a person's ear. In an example, a device for recording biometric information from a person's head can span between 75% and 100% of the circumference of the portion of the person's ear which connects the auricle to the main body of the person's head. In an example, a device for recording biometric information from a person's head can comprise a posterior portion which encircles a person's car and an anterior portion which comprises eyewear. In another example, a hybrid EEG monitoring device can comprise headphones and eyewear portions which are integrated into a single device. In an example, portions of a device for recording biometric information from a person's head which span a person's face can be transparent or translucent.

In an example, a circumaural housing can comprise a ring or band which encircles a person's auricle, but does not completely cover the ear. In an example, a circumaural housing can comprise an outer (e.g. concave) rigid shell and an inner compressive (e.g. soft, low-durometer) ring, wherein the inner compressive is made from compressible foam and/or elastomeric polymer. In another example, a circumaural housing can comprise: a thin ring or annular band which encircles a person's auricle; and a plurality of electrodes around the circumference of the housing. In an example, a circumaural housing can further comprise an inner torus-shaped compliant (e.g. low durometer) ring, wherein the torus can be geometrically modeled by revolving a convex polygon (e.g. a hexagon) in three-dimensional space around a line (e.g. axis) which is coplanar with, but does not intersect, the convex polygon.

In another example, a circumaural housing can have an elliptical or oblate circular cross-sectional shape, wherein the longest axis (e.g. widest diameter) of the shape has a vertical orientation when the wearer's head is upright. In an example, a circumaural housing can have an undulating (e.g. sinusoidal or serpentine) perimeter. In another example, a circumaural housing can include an inner low-durometer foam, gel, or sponge ring. In an example, a circumaural housing can span between 60% and 90% of a circle (or ellipse) around a person's auricle. In an example, a portion of a circumaural housing can be made with closed cell foam. In an example, the majority of a circumaural housing can be transparent.

In another example, a headband can comprise a plurality of modular, inter-locking segments which snap, clip, slide, or otherwise connect together. In another example, a headband can comprise one or more rigid segments and one or more flexible (e.g. elastic) segments. In another example, an arcuate headband which connects left-side and right-side circumaural housings can comprise two or more bands which diverge as they ascend over the upper half of a person's head and converge again on the other side of the person's head. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with foam. In an example, an arcuate headband which connects left-side and right-side circumaural housings can have an undulating (e.g. sinusoidal or serpentine) shape as it loops and/or curves over the top of a person's head.

In an example, an arcuate headband which connects left-side and right-side circumaural housings loops and/or curves over the upper half of a person's head. In an example, portions of a headband connecting left-side and right-side circumaural housings can be transparent. In another example, the length of an arcuate headband which connects left-side and right-side circumaural housings can be adjusted by moving (e.g. sliding) segments comprising the headband. In another example, the width of an arcuate headband which connects left-side and right-side circumaural housings can be between one-half inch and two inches. In an example, reference electrodes can be located at the A1 and A2 locations of the internationally-recognized Modified Combinatorial Nomenclature (MCN) electrode placement system.

In another example, an electrode can be a capacitive sensor. In an example, an electrode can be an EEG (electroencephalographic) electrode. In another example, an electrode can be an inductive sensor. In an example, an electrode can comprise an EEG sensor which collects data concerning the natural emission of electromagnetic energy by a person's brain. In an example, an electrode can function as an EEG sensor. In an example, an electrode can function as an electromagnetic energy sensor. In another example, an electrode can measure voltage fluctuations resulting from ionic current within the neurons of the brain. In an example, voltage differences between electrodes can be measured.

In another example, a circumaural housing can comprise a convex (e.g. circular, elliptical, or oblate circular) array of alternating, conductive and non-conductive, portions or segments; wherein the conductive segments function as electrodes. In an example, a circumaural housing can comprise a convex (e.g. circular, elliptical, or oblate circular) array with an alternating sequence of conductive portions (or segments) and non-conductive portions (or segments), wherein the conductive portions (or segments) function as electrodes. In an example, a circumaural housing can comprise a convex (e.g. circular, elliptical, or oblate circular) array with an alternating sequence of non-electroconductive segments and electroconductive segments; wherein the non-electroconductive segments are made from a non-electroconductive material; wherein the electroconductive segments are made from otherwise non-electroconductive material which has been doped, impregnated, or coated with conductive material; and wherein the electroconductive segments function as electrodes. In an example, an electrode can comprise an electroconductive helix and/or spiral. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are electrodes on three of the four quadrants of the circumference of the ring.

In an example, electrodes on a circumaural housing can be equally-spaced, with equal distances between proximal pairs of electrodes. In an example, electrodes on a circumaural housing can be located within three-quarters of an inch from the circumference of the housing. In an example, there can be at least four electrodes on a headband. In another example, there can be more electrodes on the posterior half of a circumaural housing than on the anterior half of the circumaural housing. In an example, an electrode can comprise a dielectric layer of low-conductivity material between two layers of high-conductivity material. In another example, an electrode can comprise a layer of high-conductivity material between two layers of low-conductivity material. In an example, an electrode can comprise an electroconductive layer and a non-electroconductive layer, wherein the non-electroconductive layer is configured to be closer to the surface of the person's head. In another example, an electrode can comprise two electroconductive layers and one dielectric layer.

In an example, a subset of a plurality of electrodes can each have a plurality of electroconductive protrusions (e.g. teeth, pins, or legs) which extend out toward the surface of a person's head. In an example, an electrode can be configured to rotate when pressed against the surface of a person's head. In an example, an electrode can comprise a plurality of longitudinal electroconductive protrusions (e.g. teeth, pins, or legs) which extend out toward the surface of a person's head, wherein the longitudinal axes of the protrusions are substantially perpendicular to the surface of the person's head. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with material with a Shore 00 value between 20 and 50. In an example, an electrode can have a plurality of electroconductive protrusions which extend out toward the surface of a person's head, wherein the electroconductive protrusions are inversely-tapered (e.g. increasing in diameter with increased proximity to the surface of the person's head).

In another example, an electrode can have protrusions (e.g. teeth, prongs, pins, or combs) which slide between strands of hair, wherein protrusions toward the center of an electrode are farther apart than protrusions toward the periphery of the electrode. In an example, an electrode can have protrusions (e.g. teeth, prongs, pins, or combs) which slide between strands of hair, wherein protrusions toward the center of an electrode have a lower durometer level than protrusions toward the periphery of the electrode. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with foam with a Shore 00 value between 20 and 50. In an example, an electrode can have protrusions, teeth, prongs, pins, or combs which slide between strands of hair.

In an example, electrodes on an arcuate headband which connects left-side and right-side circumaural housings can each have a plurality of electroconductive protrusions which slide between strands of hair to better contact the surface of a person's head. In an example, one or more of the electrodes can comprise protrusions which poke and/or slide between strands of hair to enhance electrical communication between the electrodes and portions of a person's head which are covered with hair.

In another example, an electrode can be removably-attached to a device by an adhesive. In an example, an electrode can be removably-attached to a device by a clasp. In another example, an electrode can be removably-attached to a device by a hook-and-loop fabric. In an example, an electrode can be removably-attached to a device by a plug. In an example, an electrode can be removably-attached to a device by a threaded member. In an example, electrodes can be removably-attached to different locations on a device.

In an example, a portion of an electrode can be made from polyacetylene. In an example, an electrode can be made from a thermoplastic elastomer which has been doped and/or impregnated with carbon. In another example, an electrode can be made from an elastomeric polymer which has been doped, impregnated, or coated with carbon black. In an example, an electrode can be made from PDMS. In another example, an electrode can be made with a deformable conductive polymer such as conductive PDMS or TPU. In an example, an electrode can be made with a thermoplastic elastomer (TPE) which has been impregnated, doped, or embedded with graphene. In an example, an electrode can be made with an elastomeric material. In an example, an electrode can be made with an elastomeric polymer which is doped, embedded, impregnated, or coated with conductive material.

In an example, an electrode can be made with PDMS which has been impregnated, doped, or embedded with graphite. In an example, an electrode can be made with PDMS. In another example, an electrode can be made with polydimethylsiloxane (PDMS) and silver. In an example, an electrode can be made with polydimethylsiloxane (PDMS) which has been impregnated, doped, or embedded with graphite. In another example, an electrode can be made with silicone material which has been impregnated, doped, coated, or embedded with silver or carbon. In an example, an electrode can be made with thermoplastic polyurethane (TPU) which has been impregnated, doped, or embedded with tungsten particles or pieces. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with foam with a Shore 00 value less than 60. In another example, an electrode can comprise an electroconductive polymer layer and a non-electroconductive fabric layer.

In an example, a first set of electrodes (e.g. sensors) which are configured to be worn on a portion of a person's head which is not covered by hair can have a lower average Shore value than a second set of electrodes (e.g. sensors) which is configured to be worn on a portion of the person's head which is covered with hair. In an example, an electrode can be made with a conductive metal (e.g. silver). In an example, an electrode can be made with carbon (e.g. carbon black). In an example, an electrode can be made with compressive foam which gently holds an electromagnetic energy sensor against a person's head. In an example, an electrode can be made with material with a Shore A value which is less than 80. In an example, an electrode can comprise low-conductivity fibers and highly-conductive fibers which are braided or woven together. In an example, portions of an electrode can be hydrophilic.

In another example, a plurality of electrodes can be formed on a circumaural housing by printing electroconductive ink onto a fabric, textile, and/or cloth. In an example, a plurality of electrodes can be printed using electroconductive ink on a circumaural housing which encircles and covers a person's auricle. In another example, an electrode can be made by printing a conductive pattern with electroconductive ink or resin. In an example, an electrode can be made by printing electroconductive ink onto a fabric, textile, and/or cloth. In an example, an electrode can be made by printing, spraying, or otherwise depositing electroconductive ink or resin onto an otherwise non-conductive fabric or textile. In an example, an electrode can be made with silver-printed vinyl. In an example, an electronically-functional fabric or textile with electrodes can be created by weaving, knitting, sewing, embroidering, layering, laminating, adhering, melting, fusing, printing, spraying, painting, or pressing together electroconductive threads, fibers, yarns, strands, filaments, traces, and/or layers.

In an example, an electrode can be made by embroidering a conductive pattern with electroconductive thread. In another example, an electrode can be made by embroidering conductive material onto a low-conductivity textile or fabric. In an example, an electrode can be made by laminating, adhering, or melting electroconductive material. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring covered by a woven or braided layer. In another example, an electrode can comprise a textile which is created by weaving and/or braiding electroconductive yarns, threads, or fibers.

In an example, an electrode can be moved around the circumference of a circumaural housing. In another example, an electrode can be removably-attached to different locations on a headband. In an example, the location of an electrode on a circumaural housing can be manually adjusted. In an example, the location of an electrode on a headband can be automatically adjusted by an electromagnetic actuator. In an example, there can be a track around (a portion of) the circumference of a circumaural housing, wherein an electrode can be slid along this track to adjust its location.

In an example, a device for recording biometric information from a person's head can further comprise a plurality of expandable chambers which are filled with a flowable substance (e.g. a liquid or gas), wherein changing the amount of flowable substance in the chambers changes the distance and/or pressure between electrodes and the surface of a person's head. In an example, a device for recording biometric information from a person's head can further comprise a plurality of springs (or other helical elements), wherein rotating one or more springs (or other helical elements) decreases the distance between one or more electrodes and the surface of a person's head and/or increases the pressure between the one or more electrodes and the surface of the person's head. In an example, a device for recording biometric information from a person's head can further comprise a plurality of pistons which adjust the distance and/or pressure between a plurality of electrodes and the surface of a person's head.

In another example, a headset or pair of headphones with left-side and right-side circumaural housings can be used for transcranial direct current stimulation. In an example, an electrode can function as a magnetic field generator. In another example, an electrode can provide cathodal stimulation. In an example, an electrode can transmit electrical and/or electromagnetic energy to provide Transcranial Direct Current Stimulation (tDCS). A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring. In an example, an electrode can transmit electrical and/or electromagnetic energy to modify the electromagnetic activity of a person's brain. In another example, an electrode can transmit electrical energy to (the surface of) a person's head as part of neurostimulation.

In an example, a device for recording biometric information from a person's head can further comprise a local data processor which is in wireless communication with a remote data processor. In another example, a device for recording biometric information from a person's head can include a power source such as a battery, capacitor, energy-storing microchip, or wound coil or spring. In an example, a device for recording biometric information from a person's head can use power which is obtained, harvested, or transduced from kinetic or mechanical energy from body motion, electromagnetic energy from the person's body, blood flow or other internal fluid flow, glucose metabolism, or thermal energy from the person's body. In an example, a device for recording biometric information from a person's head can further comprise one or more speakers. In an example, a device for recording biometric information from a person's head can further comprise one or more touch-activated buttons. In an example, a device for recording biometric information from a person's head can further comprise one or more accelerometers.

In an example, a device for recording biometric information from a person's head can further comprise an air pressure sensor. In another example, a device for recording biometric information from a person's head can further comprise an ambient temperature sensor. In an example, a device for recording biometric information from a person's head can further comprise a blood oximetry sensor. In another example, a device for recording biometric information from a person's head can further comprise a camera. In an example, a device for recording biometric information from a person's head can further comprise an electrooculography (EOG) sensor. In an example, a device for recording biometric information from a person's head can further comprise a heart rate sensor. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with material with a Shore A value between 10 and 30. In an example, a device for recording biometric information from a person's head can further comprise a microphone. In an example, a device for recording biometric information from a person's head can further comprise an oximetry sensor.

In an example, a biauricular headset (e.g. headphones) with electrodes for monitoring biometric signals (e.g. brainwaves) from a person's brain can further comprise: a power source (e.g. battery), a data processor, and a wireless data transmitter. In another example, a biauricular headset (e.g. headphones) with electrodes for monitoring biometric signals (e.g. brainwaves) from a person's brain can further comprise one or more of the following components: inertial motion sense (e.g. accelerometer and/or gyroscope); microphone; and electromagnetic actuator. In an example, a device for recording biometric information from a person's head can further comprise a data processor. In another example, a device for recording biometric information from a person's head can further comprise a light. In an example, a device for recording biometric information from a person's head can further comprise a tactile actuators. In another example, a device for recording biometric information from a person's head can further comprise an accelerometer.

In an example, a torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with material with a Shore A value below 30.

In an example, a device for recording biometric information from a person's head can be part of a system which further comprises a electronic tablet or pad with which the device is in wireless communication. In an example, a device for recording biometric information from a person's head can be part of a system which further comprises a smart appliance with which the device is in wireless communication. In an example, a three-dimensional model of an electromagnetic field can be used to infer an surface electromagnetic pattern which would be required to recreate an interior electromagnetic pattern. In an example, data from a plurality of electrodes can be analyzed to identify an event-related potential. In an example, Fourier Transformation can be used to decompose a complex waveform into a combination of simpler waveforms which each repeat at a different frequency or within a different frequency band.

In another example, an electrode can record electromagnetic waves (e.g. brain waves) generated by the person's brain. In an example, brainwaves or other rhythmic, cyclical, and/or repeating electromagnetic signals associated with brain activity can be measured and analyzed using one or more clinical frequency bands. In another example, data from a plurality of electrodes can be analyzed to track changes in the amplitude, power level, minimum value, and/or maximum value of brainwave activity within a selected frequency band. In an example, parameters used to identify a pattern of brainwave activity can be selected from the group consisting of: power level, amplitude, maximum value, minimum value, frequency, phase, covariation, entropy, latency, and waveform.

In an example, Beta brainwaves can be measured and analyzed within a frequency band of 12 to 30 Hz. In an example, data from a plurality of electrodes can be analyzed to measure changes in the frequency, power, and/or wave shape of brainwaves in the Alpha band. In an example, data from a plurality of electrodes can be analyzed to measure changes in the frequency, power, and/or wave shape of brainwaves in the Gamma band. In an example, Delta brainwaves can be measured and analyzed within a frequency band of 1 to 4 Hz. In an example, Theta brainwaves can be measured and analyzed within a frequency band of 4 to 8 Hz.

In another example, data from a plurality of electrodes can be analyzed using a method selected from the group consisting of: Time Frequency Analysis, Covariance, Laplacian Montage Analysis, Random Forest Analysis (RFA), Artificial Intelligence (AI), and Generalized Auto-Regressive Conditional Heteroscedasticity (GARCH) Modeling. In an example, data from a plurality of electrodes can be analyzed using a method selected from the group consisting of: Machine Learning (ML), Sine Wave Compositing, Dynamic Bayesian Network, Markov Model, Singular Value Decomposition (SVD), Fourier Transformation (FT) Method, Multivariate Logit, Waveform Identification, Fisher Linear Discriminant, Multivariate Linear Regression, and Variance.

In another example, data from a plurality of electrodes can be analyzed using a method selected from the group consisting of: Auto-Regressive (AR) Modeling, Independent Components Analysis (ICA), Non-Linear Programming, Bonferroni Analysis (BA), Inter-Channel Power Ratio, Pattern Recognition, and Fast Fourier Transform (FFT). In an example, data from a plurality of electrodes can be analyzed using a method selected from the group consisting of: Eigenvalue Decomposition, Maximum Entropy Modeling, and Support Vector Machine (SVM).

In an example, a headset or pair of headphones with left-side and right-side circumaural housings can be used for biofeedback. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with material with a Shore A value between 10 and 30. In an example, an electrode can record waves and/or patterns of electrical energy emitted from a person's brain, wherein these waves and/or patterns are analyzed to make inferences concerning the person's brain activity. In an example, analysis of data from a plurality of electrodes can be used to give a person real-time feedback based on their brain activity.

In an example, a device for recording biometric information from a person's head can be embodied in a headphone-style wearable. In an example, a device for recording biometric information from a person's head can comprise: a headband or set of headphones which is configured to be worn on a person's head; a plurality of electromagnetic energy emitters which are configured to be held in electromagnetic communication with the person's brain by the headband or set of headphones; and a control unit with one or more components selected from the group consisting of power source and/or power-transducing component, data transmission and data reception component, data memory component, and data processor. In another example, a pair of EEG-monitoring headphones can include electrodes (e.g. sensors) which are knitted or woven from soft, elastic, and/or stretchable yarns and/or threads, wherein some of these yarns or threads are electroconductive. In an example, a pair of EEG-monitoring headphones can include electrodes (e.g. sensors) made from a deformable conductive polymer.

In another example, a device for recording biometric information from a person's head can comprise a portion which loops over the top of a person's head and a portion which curves around the person's car. In an example, a device for recording biometric information from a person's head can be embodied in an ear clip, car ring, or ear phone. In another example, a device for recording biometric information from a person's head can be worn on a person's car and/or within the person's car canal. In an example, a device for recording biometric information from a person's head can span between 75% and 100% of the circumference of a person's ear (e.g. auricle). In an example, a device for recording biometric information from a person's head can comprise a posterior portion which loops over the top (e.g. upper half) of a person head and an anterior portion which comprises eyewear. In an example, headphones and eyewear can be integrated into a single device.

In an example, a circumaural housing can completely cover a person's auricle. In an example, a circumaural housing can comprise an outer (e.g. further from the surface of a person's head) rigid concave shell and an inner (e.g. closer to the surface of the person's head) soft (e.g. low-durometer) torus-shaped ring, wherein the electrodes are on the ring. In another example, a circumaural housing can comprise: a rigid outer concave shell which covers a person's auricle; an inner sound-emitting component (e.g. speaker); an inner compressible (e.g. soft or low durometer) ring and/or annular band; and a plurality of electrodes around the circumference of the housing.

In an example, a circumaural housing can further comprise a compressible, soft, and/or low durometer inner ring or annular band between the housing and the person's head. In an example, a circumaural housing can have a cross-sectional shape whose perimeter is circular, elliptical, or oblate circular. In an example, a circumaural housing can have an elliptical or oblate circular cross-sectional shape, wherein the longest axis (e.g. widest diameter) of the shape has an orientation which is slightly forward-tilted (e.g. 5 to 20 degrees away) from vertical when the wear's head is upright. In another example, a circumaural housing can have an undulating (e.g. sinusoidal or serpentine) shape. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with material with a Shore 00 value below 60.

In an example, a circumaural housing can include an inner torus-shaped compliant (e.g. low durometer) ring, wherein the torus can be geometrically modeled by revolving a circle in three-dimensional space around a line (e.g. axis) which is coplanar with, but does not intersect, the circle. In another example, a circumaural housing which covers a person's auricle can further comprise a speaker (or other sound-emitting component) and the headset can comprise a pair of headphones. In an example, a ring or annular band which encircles a person's auricle can fit flat against a person's head, with a thickness of less than a half inch. In another example, a circumaural housing can comprise a ring or annular band which encircles a person's auricle, but does not cover it.

In another example, a headband can comprise a plurality of telescoping segments. In an example, an arcuate headband can further comprise a plurality of telescoping, sliding, and/or interlocking band segments which enable adjustment of the length of the headband. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring. In an example, an arcuate headband which connects left-side and right-side circumaural housings can comprise two or more substantially-parallel bands which loop and/or curve over the upper half of a person's head. In an example, an arcuate headband which connects left-side and right-side circumaural housings can loop and/or curve over the upper half (e.g. the top) of a person's head.

In an example, left-side and right-side circumaural housings can be connected by two bands which loop over the upper half of a person's head, wherein the two bands converge near the housings and diverge on the upper half of the person's head. In an example, the angle(s) between two or more diverging arcuate bands which curve and/or loop over the top of a person's head can be adjusted. In an example, the majority of the length of a headband connecting left-side and right-side circumaural housings can be transparent. In another example, electrodes can be located at locations of the internationally-recognized Modified Combinatorial Nomenclature (MCN) electrode placement system selected from the group comprising: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POZ, PO4, PO6, PO8, O1, Oz, and O2.

In an example, a device for recording biometric information from a person's head can measure changes in electrical impedance, voltage, and/or energy transfer between two electrode locations on a person's head. In another example, an electrode can be a dry electrode (e.g. not requiring a conductive gel to have good electroconductive communication with the surface of a person's head). In an example, an electrode can be an EEG sensor which measure electromagnetic brain activity. In an example, an electrode can collect data concerning (changes in) the conductivity, resistance, and/or impedance of electromagnetic energy transmitted through body tissue. In an example, an electrode can comprise an electroconductive coil. In an example, an electrode can function as an electrical energy sensor. In an example, an electrode can measure changes in the transmission of electrical energy from an energy emitter to an energy receiver due to changes in electromagnetic brain activity. In an example, one of the electrodes on a circumaural housing can be a reference electrode.

In another example, a circumaural housing can comprise a convex (e.g. circular, elliptical, or oblate circular) array of electrodes around the circumference of the housing. In an example, a circumaural housing can comprise a convex (e.g. circular, elliptical, or oblate circular) array of alternating, conductive and non-conductive, portions or segments; wherein the conductive portions or segments function as electrodes. In another example, a circumaural housing can comprise a convex (e.g. circular, elliptical, or oblate circular) array with an alternating sequence of conductive polymer portions (or segments) and non-conductive polymer portions (or segments), wherein the conductive portions (or segments) function as electrodes.

In an example, a circumaural housing can comprise a convex (e.g. circular, elliptical, or oblate circular) array with an alternating sequence of non-electroconductive segments and electroconductive segments; wherein the non-electroconductive segments are made from a non-electroconductive elastomeric polymer (e.g. a silicon-based polymer);

wherein the electroconductive segments are made from an elastomeric polymer which has been doped, impregnated, or coated with conductive material (e.g. carbon structures, silver, or aluminum); and wherein the electroconductive segments function as electrodes.

In an example, electrodes in a circumaural housing can be clustered on an anterior portion of the housing (e.g. anterior to the auricle) and on a posterior portion of the housing (e.g. posterior to the auricle). In an example, electrodes on a circumaural housing can be evenly distributed around the circumference of the circumaural housing. In another example, there can be at least four electrodes in a plurality of electrodes on a circumaural housing. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with material with a Shore 00 value below 60. In an example, there can be at least one electrode which is anterior to the auricle, at least one electrode which is posterior to the auricle, at least one electrode which is higher than the auricle, and at least one electrode which is below the auricle. In another example, there can be three electrodes on a circumaural housing which are anterior to a person's auricle and three electrodes on the circumferential housing which are posterior to the person's auricle.

In an example, an electrode can comprise a gel layer which gently holds an electromagnetic energy sensor against a person's head. In another example, an electrode can comprise a non-electroconductive layer between two electroconductive layers. In an example, an electrode can comprise an electroconductive layer and a dielectric layer. In another example, an electrode can have a dielectric layer. In an example, a subset of a plurality of electrodes on a circumaural housing can each have a plurality of electroconductive protrusions (e.g. teeth, pins, or legs) which extend out toward the surface of a person's head, wherein this subset is between 10% and 40% of the electrodes on the housing. In an example, an electrode can comprise a plurality of arcuate longitudinal electroconductive protrusions (e.g. teeth, pins, or legs) which extend out toward the surface of a person's head, wherein the ends of protrusions diverge from each other.

In an example, an electrode can comprise a plurality of longitudinal electroconductive protrusions (e.g. teeth, pins, or legs) which extend out toward the surface of a person's head, wherein the longitudinal axes of the protrusions are substantially parallel to each other. In an example, an electrode can have a plurality of electroconductive protrusions which extend out toward the surface of a person's head, wherein the electroconductive protrusions are tapered (e.g. decreasing in diameter with increased proximity to the surface of the person's head). A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are electrodes on two of the four quadrants of the circumference of the ring. In an example, an electrode can have protrusions (e.g. teeth, prongs, pins, or combs) which slide between strands of hair, wherein protrusions toward the center of an electrode are closer together than protrusions toward the periphery of the electrode.

In an example, an electrode can have protrusions (e.g. teeth, prongs, pins, or combs) which slide between strands of hair, wherein protrusions toward the center of an electrode are longer than protrusions toward the periphery of the electrode. In an example, an electrode can have protrusions, teeth, prongs, pins, or combs which slide between strands of hair, wherein these are made with a silicone material (such as PDMS) which has been impregnated, doped, coated, or embedded with conductive material (such as a metal and/or carbon). In another example, one or more electrodes on a circumaural housing can have a flat surface in contact with the surface of the person's head and one or more electrodes on the arcuate headband can have a plurality of electroconductive protrusions which penetrate hair to contact with the surface of the person's head.

In an example, a plurality of electrodes can be attached to a circumaural housing and/or a headband by one or more means selected from the group consisting of: adhesion, clamp, clip, helical-thread, hook, hook-and-loop textile, interlocking teeth, magnet, pin, prong, snap, and welding. In another example, an electrode can be removably-attached to a device by a buckle. In an example, an electrode can be removably-attached to a device by a clip. In another example, an electrode can be removably-attached to a device by a magnet. In an example, an electrode can be removably-attached to a device by a snap. In another example, an electrode can be removably-attached to a device by a tie. In an example, electrodes can be removably-attached to different locations on a headband. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with foam.

In an example, a portion of an electrode can be made from polyaniline. In an example, an electrode can be made from an elastomeric polymer which has been doped, impregnated, or coated with silver chloride. In an example, an electrode can be made from PDMS which has been doped, impregnated, and/or coated with silver. In an example, an electrode can be made from thermoplastic polyurethane and silver. In an example, an electrode can be made with a polymer which has been impregnated, doped, coated, or embedded with conductive material. In another example, an electrode can be made with a woven polymer material.

In an example, an electrode can be made with an elastomeric material (such as an elastomeric polymer) which is doped, impregnated, or embedded with conductive particles or microstructures (such as metal particles or microstructures). In another example, an electrode can be made with conductive polydimethylsiloxane (PDMS), thermoplastic polyurethane (TPU), or poly(3,4-ethylenedioxythiophene): poly(styrene sulfonate) (PEDOT:PSS). In an example, an electrode can be made with PDMS which has been impregnated, doped, or embedded with carbon nanotubes. In another example, an electrode can be made with PEDOT:PSS.

In an example, an electrode can be made with polydimethylsiloxane (PDMS) which has been doped or impregnated with aluminum, carbon (in one or more various configurations and formulations), copper, gold, nickel, silver, or steel. In an example, an electrode can be made with polydimethylsiloxane (PDMS), thermoplastic polyurethane (TPU), or poly(3,4-ethylenedioxythiophene):poly(styrene sulfonate) (PEDOT:PSS). In an example, an electrode can be made with silicone-based material. In an example, an electrode can comprise a silicon-based polymer (e.g. PDMS) which has been doped, impregnated, and/or coated with electroconductive material (e.g. carbon microstructures, silver, or aluminum). In an example, an electrode can have silicone-based layer.

In an example, a portion of an electrode can comprise a compliant (e.g. low durometer) foam, gel, or sponge material. In another example, an electrode can be made with aluminum. In an example, an electrode can be made with carbon in the form of nanotubes or graphene. In another example, an electrode can be made with electroconductive threads, fibers, yarns, strands, filaments, traces, and/or layers within a fabric or textile. In an example, an electrode can be made with silver. In another example, an electrode can comprise low-conductivity material which has been doped, impregnated, or coated with a high-conductivity material. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with material with a Shore 00 value between 20 and 50. In an example, portions of an electrode can be made with a high-conductivity material selected from the group consisting of: aluminum or aluminum alloy; carbon nanotubes, graphene, or other carbon-based material; copper or copper alloy; gold; nickel; silver; and steel.

In an example, a plurality of electrodes can be printed using electroconductive ink on an inner foam ring or annular band which encircles a person's auricle. In an example, an electrode can be 3D printed with conductive ink. In an example, an electrode can be made by printing a conductive elastomeric material onto a low-conductivity textile or fabric. In an example, an electrode can be made by printing high-conductivity ink onto a low-conductivity textile or fabric. In an example, an electrode can be made by weaving, knitting, sewing, embroidering, layering, laminating, adhering, melting, fusing, printing, spraying, painting, or pressing together electroconductive threads, fibers, yarns, strands, filaments, traces, and/or layers. In an example, an electrode can be printed with conductive ink which has been doped, impregnated, and/or coated with carbon. In another example, an electronically-functional fabric or textile with electrodes can be created by printing, spraying, or otherwise depositing electroconductive ink or resin onto an otherwise non-conductive fabric or textile.

In an example, an electrode can be made by embroidering a generally non-conductive fabric or textile with electroconductive material (e.g. conductive thread). In another example, an electrode can be made by heat adhesion and/or melting of a conductive polymer onto fabric. In an example, an electrode can be made by melting or adhering elastomeric conductive material onto a low-conductivity textile or fabric. In another example, an electrode can be modular. In an example, an electrode can be removably-attached (e.g. by a snap, clip, pin, or magnet) to different locations on a headband. In another example, an electrode can be removably-attached to different locations on a circumaural housing. In an example, the location of an electrode on a circumaural housing can be automatically adjusted by an electromagnetic actuator. In another example, the location of an electrode on of a headband can be manually adjusted.

In an example, a device for recording biometric information from a person's head can further comprise a plurality of inflatable chambers, wherein inflation of the chambers changes the distance and/or pressure between electrodes and the surface of a person's head. In another example, a device for recording biometric information from a person's head can further comprise a plurality of expandable chambers which can be selectively and individually filled with a flowable substance (e.g. a liquid or gas), wherein pumping the flowable substance into one or more expandable chambers decreases the distance between one or more electrodes and the surface of a person's head and/or increases the pressure between the one or more electrodes and the surface of the person's head. In an example, a device for recording biometric information from a person's head can further comprise a plurality of threaded members, wherein rotating one or more threaded members decreases the distance between one or more electrodes and the surface of a person's head and/or increases the pressure between the one or more electrodes and the surface of the person's head.

In another example, a biauricular headset with electrodes can be used for neurostimulation and/or neuromodulation (instead of monitoring biometric signals). In an example, a headset or pair of headphones with left-side and right-side circumaural housings can be used for transcranial magnetic stimulation. In an example, an electrode can function as an electromagnetic energy emitter. In an example, an electrode can transmit electrical and/or electromagnetic energy to provide neurostimulation. In an example, an electrode can transmit electrical and/or electromagnetic energy to provide Transcranial Electric Stimulation (tES). A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein the convex shape which is revolved in three-dimensional space to form the torus shape is an ellipse, and wherein there are a plurality of electrodes on the ring. In an example, an electrode can transmit electrical and/or electromagnetic energy to modify, adjust, stimulate, and/or block electromagnetic brain activity. In an example, neurostimulation provided by a plurality of electrodes can be used to help reduce hunger, pain, headaches, tremors, seizures, stress, and/or depression.

In an example, a device for recording biometric information from a person's head can include a power source (e.g. a rechargeable battery). In an example, a device for recording biometric information from a person's head can include a transducer which harvests power from human physiological activity and/or environmental energy sources. In another example, a device for recording biometric information from a person's head can further comprise a display screen. In an example, a device for recording biometric information from a person's head can further comprise one or more tactile actuators. In another example, a device for recording biometric information from a person's head can further comprise a microphone. In an example, an device can provide auditory biofeedback.

In an example, a device for recording biometric information from a person's head can further comprise an ambient light sensor. In an example, a device for recording biometric information from a person's head can further comprise a blood flow sensor. In an example, a device for recording biometric information from a person's head can further comprise a blood pressure sensor. In an example, a device for recording biometric information from a person's head can further comprise a chewing and/or swallowing sensor. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with foam with a Shore 00 value between 20 and 50. In an example, a device for recording biometric information from a person's head can further comprise a global positioning system (GPS) module. In another example, a device for recording biometric information from a person's head can further comprise a hydration sensor. In an example, a device for recording biometric information from a person's head can further comprise a motion sensor. In another example, a device for recording biometric information from a person's head can further comprise a spectroscopic sensor.

In an example, a biauricular headset (e.g. headphones) with electrodes for monitoring biometric signals (e.g. brainwaves) from a person's brain can further comprise: a power source (e.g. battery), a data processor, a wireless data transmitter, and a wireless data receiver. In another example, a device for recording biometric information from a person's head can further comprise a camera. In an example, a device for recording biometric information from a person's head can further comprise a display screen. In an example, a device for recording biometric information from a person's head can further comprise a microphone. In an example, a device for recording biometric information from a person's head can further comprise a touch-activated button. In an example, a device for recording biometric information from a person's head can further comprise two speakers.

In an example, a device for recording biometric information from a person's head can be part of a system which further comprises a handheld device with which the device is in wireless communication. In an example, a device for recording biometric information from a person's head can be part of a system which further comprises a smart eyewear with which the device is in wireless communication. In an example, a three-dimensional model of an electromagnetic field can be used to infer an interior electromagnetic pattern which creates a surface electromagnetic pattern. In another example, data from a plurality of electrodes can be filtered using one or more of the following filters: high-pass filter, band-pass filter, loss-pass filter, electromyographic activity filter, 5-1 Hz filter, and 35-70 Hz filter. In an example, Fourier Transformation can be used to find a frequency or frequency band of waveform and/or rhythmic data which repeats over time.

In another example, brainwave form or morphology can be identified from the group consisting of: simple sinusoidal wave, composite sinusoidal wave, simple saw-tooth wave, composite saw-tooth wave, biphasic wave, tri-phasic wave, and spike. In an example, complex repeating brainwave patterns can be decomposed into wave frequency bands and/or frequency power levels using Fourier Transformation. In another example, data from a plurality of electrodes can be analyzed to identify changes in the shape of a waveform within a selected frequency band.

In an example, Alpha brainwaves can be measured and analyzed within a frequency band of 7 to 14 Hz. In an example, Beta brainwaves or other rhythmic, cyclical, and/or repeating electromagnetic signals associated with brain activity can be measured and analyzed within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. In an example, data from a plurality of electrodes can be analyzed to measure changes in the frequency, power, and/or wave shape of brainwaves in the Beta band.

In an example, a torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring covered by a woven or braided layer. In an example, data from a plurality of electrodes can be analyzed to measure changes in the frequency, power, and/or wave shape of brainwaves in the Theta band. In an example, Gamma brainwaves can be measured and analyzed within a frequency band of 30 to 100 Hz. In an example, Theta brainwaves or other rhythmic, cyclical, and/or repeating electromagnetic signals associated with brain activity can be measured and analyzed within a frequency band selected from the group consisting of: 3.5-7 Hz, 3-7 Hz, 4-7 Hz, 4-7.5 Hz, 4-8 Hz, and 5-7 Hz.

In another example, data from a plurality of electrodes can be analyzed using a method selected from the group consisting of: Naive Bayes Classifier, Covariance, Least Squares Estimation, Regression Model, Data Normalization (DN), Linear Regression, Signal Amplitude (SA), Decision Tree Analysis (DTA), and Linear Transform. In an example, data from a plurality of electrodes can be analyzed using a method selected from the group consisting of: Centroid Analysis, Inter-Montage Ratio, Power Spectrum Analysis, Chi-Squared Analysis, Kalman Filter (KF), Principal Components Analysis (PCA), Analysis of Wave Frequency, and Fuzzy Logic (FL) Modeling. In another example, data from a plurality of electrodes can be analyzed using a method selected from the group consisting of: Multi-Band Covariance Analysis, Time Series Model, ANOVA or MANOVA, Gaussian Model (GM), Multivariate Regression, Wavelet Transformation, and Empirical Mode Decomposition (EMD).

In an example, a device can be used for brainwave entrainment. In another example, a headset with electrodes on left-side and right-side circumaural housings can be used for brainwave entrainment. In an example, analysis of data from a plurality of electrodes can be used by health care providers to better diagnose (brain-related) health conditions. In an example, electrodes can be used to monitor a person's neural (e.g. brain) signals.

In an example, a device for recording biometric information from a person's head can be embodied in an ear muff or headphones. In an example, a device for recording biometric information from a person's head can comprise: a headband or set of headphones which is configured to be worn on a person's head; a plurality of electrodes (e.g. sensors) which are configured to be held in electromagnetic communication with the person's brain by the headband or set of headphones, wherein these sensors collect data concerning the person's electromagnetic brain activity; and a control unit with one or more components selected from the group consisting of power source and/or power-transducing component, data transmission and data reception component, data memory component, and data processor. In another example, a pair of EEG-monitoring headphones can include electrodes (e.g. sensors) made from PEDOT:PSS. In an example, a posterior portion of a device for recording biometric information from a person's head can comprise a set of headphones which covers a person's ears and loops over the top of the person's head.

In another example, a device for recording biometric information from a person's head can be embodied in a headset and/or headband. In an example, a device for recording biometric information from a person's head can be worn around a person's ear (e.g. auricle). A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes on the ring, and wherein the ring is made with material with a Shore A value below 30. In another example, a device for recording biometric information from a person's head can comprise: a hearing aid or ear bud which is configured to be worn in, worn on, and/or worn around a person's ear; one or more electrodes or other brain activity sensors which are configured by the hearing aid or ear bud to be less than one inch from the surface of the person's head; a mobile power source; a data processor; and a data transmitter.

In an example, a device for recording biometric information from a person's head can comprise: a plurality of electrodes or other brain activity sensors which are configured to be worn less than one inch from the surface of a person's head; a mobile power source and/or power transducer, wherein a power transducer harvests power from human physiological activity and/or environmental energy sources; and a data processor. In an example, a device for recording biometric information from a person's head can comprise: an first posterior portion encircles a person's ear, a second posterior portion which loops over the top (e.g. upper half) of the person head; and an anterior portion which comprises eyewear. In an example, portions of a device for recording biometric information from a person's head can be transparent or translucent.

In an example, a circumaural housing can comprise a ring or annular band which encircles a person's auricle, wherein the auricle protrudes through an open center of the ring or band. In an example, a circumaural housing can comprise an outer (e.g. concave) rigid shell and an inner compressive (e.g. soft, low-durometer) ring, wherein the inner compressive ring is closer to the surface of a person's head. In an example, a circumaural housing can comprise: a rigid outer concave shell which covers a person's auricle; an inner sound-emitting component (e.g. speaker); an inner compressible (e.g. soft or low durometer) ring or annular band; and a plurality of electrodes on the ring and/or annular band.

In another example, a circumaural housing can further comprise a foam and/or textile ring or annular band between the housing and the person's head. In an example, a circumaural housing can have a toroidal shape. In another example, a circumaural housing can have an outer-surface concave shape which is a section of a sphere, ellipsoid or oblate spheroid. In an example, a circumaural housing can include an inner annular ring which is made with closed cell foam. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein the convex shape which is revolved in three-dimensional space to form the torus shape is an ellipse, and wherein there are a plurality of electrodes on the ring.

In another example, a circumaural housing can include an inner torus-shaped compliant (e.g. low durometer) ring, wherein the torus can be geometrically modeled by revolving a convex shape (e.g. a circle or ellipse) n three-dimensional space around a line (e.g. axis) which is coplanar with, but does not intersect, the convex shape. In an example, a left side or right side circumaural housing (e.g. speaker casing, ear pad, ear cuff, ring, or band) completely covers a person's auricle and has a shape which is a section of a sphere, ellipsoid, or oblate spheroid. In an example, portions of a circumaural housing can be transparent.

In an example, a headband can comprise a longitudinal series of rigid and flexible (e.g. elastic) segments. In an example, a headband can comprise an alternating sequence of rigid and flexible (e.g. elastic) segments. In an example, an arcuate headband which connects left-side and right-side circumaural housings can bifurcate as it loops and/or curves over the upper half of a person's head. In another example, an arcuate headband which connects left-side and right-side circumaural housings can loop and/or curve over the top of a person's head. In an example, an arcuate headband which connects left-side and right-side circumaural housings comprises a single band.

In another example, left-side and right-side circumaural housings can be connected by two or more bands which loop over the upper half of a person's head, wherein the two bands converge near the housings and diverge on the upper half of the person's head. In an example, the curvature (e.g. concavity) of an arcuate headband which connects left-side and right-side circumaural housings can be adjusted by moving (e.g. sliding) segments comprising the headband. In another example, the tension and/or flexibility of an arcuate headband which connects left-side and right-side circumaural housings can be adjusted by moving (e.g. sliding) segments comprising the headband.

In an example, electrodes can be located in proximity to one or more areas of a person's brain selected from the group comprising: Broca's area (of the Frontal Lobe), Wernicke's area (of the Occipital Lobe), Cerebellum, Cerebral Cortex, Frontal Lobe, Occipital Lobe, Parietal Lobe, and Temporal Lobe. In another example, an electrode can be a capacitive electrode. In an example, an electrode can be a dry electrode (e.g. not requiring gel or liquid to have good electromagnetic contact with the surface of a person's head). In an example, an electrode can be an impedance-based electrode. In an example, an electrode can collect data on electromagnetic energy patterns and/or electromagnetic fields which are generated by brain activity. In an example, an electrode can function as a magnetic field sensor. In an example, an electrode can function as an electromagnetic energy receiver. In another example, an electrode can measure the conductivity, voltage, resistance, and/or impedance of electromagnetic energy emitted from an electromagnetic energy emitter and transmitted through a portion of a person's head. In an example, one of the electrodes on a circumaural housing can function as a ground electrode.

In another example, a circumaural housing can comprise a convex (e.g. circular, elliptical, or oblate circular) array of electrodes on a compressible annular ring which encircles a person's auricle. In an example, a circumaural housing can comprise a convex (e.g. circular, elliptical, or oblate circular) array of alternating, conductive and non-conductive, woven portions or segments; wherein the conductive portions or segments function as electrodes. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein there are a plurality of electrodes distributed around the circumference of the ring. In another example, a circumaural housing can comprise a convex (e.g. circular, elliptical, or oblate circular) array with an alternating sequence of non-electroconductive segments and electroconductive segments; wherein the non-electroconductive segments are made from a non-electroconductive elastomeric polymer; wherein the electroconductive segments are made from an elastomeric polymer which has been doped, impregnated, or coated with conductive material; and wherein the electroconductive segments function as electrodes. In an example, an electrode can comprise a helical and/or spiral conductive element.

In an example, electrodes on a circumaural housing can be disproportionately clustered on the half of the housing which is posterior to a person's auricle. In an example, electrodes on a circumaural housing can be located within a half inch from the circumference of the housing. In an example, there can be at least four electrodes in a plurality of electrodes on a circumaural housing, wherein there is at least one electrode in each quadrant (of the circumference) of the circumaural housing. In an example, there can be more electrodes on the anterior half of a circumaural housing than on the posterior half of the circumaural housing. In another example, there can be two electrodes on a circumaural housing which are anterior to a person's auricle and two electrodes on the circumferential housing which are posterior to the person's auricle. In an example, an electrode can comprise a layer of fabric and a layer of polyurethane. In another example, an electrode can comprise an electroconductive layer and a non-electroconductive layer. In an example, an electrode can comprise layers of conductive elastomeric material. In another example, an electrode can include a hydrophilic layer.

In an example, a subset of a plurality of electrodes on a circumaural housing can each have a plurality of electroconductive protrusions (e.g. teeth, pins, or legs) which extend out toward the surface of a person's head, wherein this subset is between 30% and 60% of the electrodes on the housing. In another example, an electrode can comprise a plurality of frustum-shaped electroconductive protrusions (e.g. teeth, pins, or legs) which extend out toward the surface of a person's head. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with material with a Shore 00 value between 10 and 60. In an example, an electrode can comprise a plurality of longitudinal electroconductive protrusions (e.g. teeth, pins, or legs) which extend out toward the surface of a person's head, wherein the protrusions are longitudinally tapered. In an example, an electrode can have a plurality of helical protrusions which extend outward toward the surface of a person's head.

In an example, an electrode can have protrusions (e.g. teeth, prongs, pins, or combs) which slide between strands of hair, wherein protrusions toward the center of an electrode have a higher durometer level than protrusions toward the periphery of the electrode. In an example, an electrode can have protrusions (e.g. teeth, prongs, pins, or combs) which slide between strands of hair, wherein protrusions toward the center of an electrode are shorter than protrusions toward the periphery of the electrode. In an example, an electrode include springs and/or helical threads which cause the electrode to rotate when it is pressed against the surface of a person's head. In an example, one or more electrodes on a circumaural housing which are anterior to a person's auricle can have a flat surface in contact with the surface of the person's head and one or more electrodes on the circumferential housing which are posterior to the person's auricle can have a plurality of electroconductive protrusions which penetrate hair to contact the surface of the person's head.

In another example, an electrode can be modular. In an example, an electrode can be removably-attached to a device by a button. In another example, an electrode can be removably-attached to a device by a hook. In an example, an electrode can be removably-attached to a device by a pin. In another example, an electrode can be removably-attached to a device by a tape. In an example, electrodes can be modular, wherein they can be removably-attached to different locations on a headband or a circumaural housing. In an example, electrodes can be removably-attached to different locations on a circumaural housing.

In an example, a portion of an electrode can be made from polyvinyl alcohol. In an example, an electrode can be made from an elastomeric polymer which has been doped, impregnated, or coated with carbon nanotubes. In an example, an electrode can be made from PDMS which has been doped, impregnated, and/or coated with carbon. In another example, an electrode can be made with a conductive rubber. In an example, an electrode can be made with a silicone rubber elastomer. In another example, an electrode can be made with a woven polymer material which has been printed with electroconductive ink.

In an example, an electrode can be made with an elastomeric polymer which has been doped and/or impregnated with steel particles. In another example, an electrode can be made with electroconductive threads, yarns, fibers, strands, channels, and/or traces. In an example, an electrode can be made with PDMS which has been impregnated, doped, or embedded with aluminum. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are electrodes on three of the four quadrants of the circumference of the ring. In an example, an electrode can be made with polydimethylsiloxane (PDMS) and carbon nanotubes. In an example, an electrode can be made with polydimethylsiloxane (PDMS) which has been impregnated, doped, or embedded with carbon nanotubes.

In an example, an electrode can be made with silicone material (such as PDMS) which has been impregnated, doped, coated, or embedded with conductive material (such as metal and/or carbon). In an example, an electrode can be made with thermoplastic polyurethane (TPU). In another example, an electrode can comprise an elastomeric polymer which has been doped, impregnated, and/or coated with electroconductive material. In an example, portions of an electrode can be made with low-conductivity material selected from the group consisting of: acetate, acrylic, cotton, denim, elastane, latex, linen, neoprene, nylon, nylon, polyester, wool, silicone, polydimethylsiloxane (PDMS), silk, spandex, and rayon.

In another example, an electrode can be made from silver chloride. In an example, an electrode can be made with an elastic, stretchable, and/or deformable conductive material. In another example, an electrode can be made with carbon. In an example, an electrode can be made with material with a low Shore A value (e.g. less than 80). In an example, an electrode can comprise a fabric, textile, or yarn which has been doped, impregnated, and/or coated with electroconductive material (e.g. carbon microstructures, silver, or aluminum). In an example, an electrode can contain graphite.

In an example, a plurality of electrodes can be formed on a circumaural housing by printing with electroconductive ink. In an example, a plurality of electrodes can be printed using electroconductive ink on a compressive (e.g. soft and low-durometer) inner ring or annular band which encircles a person's auricle. In an example, an electrode can be made by 3D printing or silk screening. In an example, an electrode can be made by printing conductive ink onto fabric. In another example, an electrode can be made by printing with electroconductive material (e.g. ink or resin). In an example, an electrode can be made by weaving, knitting, sewing, embroidering, layering, laminating, adhering, melting, fusing, printing, spraying, painting, or pressing electroconductive material into (or onto) a fabric or textile. In another example, an electrode can be printed with conductive ink which has been doped, impregnated, and/or coated with metal particles.

In an example, an electrode can be made by adhesion of a conductive polymer onto fabric. In another example, an electrode can be made by embroidering and/or sewing electroconductive material (e.g. conductive yarns, threads, or fibers). In an example, an electrode can be made by laminating electro-conductive members onto a non-conductive substrate. In an example, an electrode can be made by sewing or weaving electroconductive threads or yarns into an elastic and/or stretchable headband. In an example, an electrode can be moved along the length of a headband. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a torus-shaped (e.g. toroidal) low-durometer (e.g. soft, compressible, and/or compliant) ring which encircles a person's auricle, wherein the convex shape which is revolved in three-dimensional space to form the torus shape is an oblate circle, and wherein there are a plurality of electrodes on the ring. In an example, an electrode can be removably-attached (e.g. by a snap, clip, pin, or magnet) to different locations on a circumaural housing. In an example, the location of an electrode on a circumaural housing can be adjusted. In an example, the location of an electrode on a headband can be adjusted. In another example, there can be a track along (a portion of) the length of a headband, wherein an electrode can be slid along this track to adjust its location.

In an example, a device for recording biometric information from a person's head can further comprise a plurality of individually and selectively inflatable chambers, wherein selective inflation of the chambers selectively changes the distance and/or pressure between selective electrodes and the surface of a person's head. In another example, a device for recording biometric information from a person's head can further comprise a plurality of solenoids (or other electromagnetic actuators), wherein activating one or more solenoids (or other electromagnetic actuators) decreases the distance between one or more electrodes and the surface of a person's head and/or increases the pressure between the one or more electrodes and the surface of the person's head. In an example, a device for recording biometric information from a person's head can further comprise an expandable chamber which is filled with a flowable substance (e.g. a liquid or gas), wherein pumping the flowable substance into the expandable chamber decreases the distance between an electrode and the surface of a person's head and/or increases the pressure between the electrode and the surface of the person's head.

In another example, a headset or pair of headphones with left-side and right-side circumaural housings can be used for transcranial electrical stimulation. In an example, a headset or pair of headphones with left-side and right-side circumaural housings can be used for neuromodulation. In an example, an electrode can provide anodal stimulation. In an example, an electrode can transmit electrical and/or electromagnetic energy to provide Transcranial Alternating Current Stimulation (tACS). In an example, an electrode can transmit electrical and/or electromagnetic energy to provide Transcranial Magnetic Stimulation (tMS). In an example, an electrode can transmit electrical energy to (the surface of) a person's head.

In an example, a device for recording biometric information from a person's head can further comprise a data processor, central processing unit, microchip, microprocessor, and/or circuit board. In another example, a device for recording biometric information from a person's head can include a power source selected from the group consisting of: a rechargeable battery, electromagnetic inductance from external source, solar energy, indoor lighting energy, wired connection to an external power source, ambient or localized radiofrequency energy, or ambient thermal energy. In an example, a device for recording biometric information from a person's head can include an energy harvesting member which transduces kinetic, thermal, and/or ambient electromagnetic energy into power for the device. In another example, a device for recording biometric information from a person's head can further comprise one or more lights. In an example, a device for recording biometric information from a person's head can further comprise a touch screen. In another example, a device for recording biometric information from a person's head can have speech-recognition and/or gesture recognition capability.

In an example, a device for recording biometric information from a person's head can further comprise an accelerometer. In another example, a device for recording biometric information from a person's head can further comprise an ambient sound sensor. In an example, a device for recording biometric information from a person's head can further comprise a blood glucose sensor. In an example, a device for recording biometric information from a person's head can further comprise a body temperature sensor. In an example, a device for recording biometric information from a person's head can further comprise a electromyography (EMG) sensor. In an example, a device for recording biometric information from a person's head can further comprise a gyroscope. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes on the ring, and wherein the ring is made with foam with a Shore 00 value less than 60. In an example, a device for recording biometric information from a person's head can further comprise an infrared sensor. In an example, a device for recording biometric information from a person's head can further comprise an optical sensor. In an example, a device for recording biometric information from a person's head can further comprise a thermometer.

In another example, a biauricular headset (e.g. headphones) with electrodes for monitoring biometric signals (e.g. brainwaves) from a person's brain can further comprise: a power source (e.g. battery), a data processor, a wireless data transmitter, a wireless data receiver, and two sound-emitting components (e.g. speakers). In an example, a device for recording biometric information from a person's head can further comprise a data memory component. In another example, a device for recording biometric information from a person's head can further comprise a GPS component. In an example, a device for recording biometric information from a person's head can further comprise a power source or transducer. In another example, a device for recording biometric information from a person's head can further comprise a wireless data transmitter.

In an example, a device for recording biometric information from a person's head can be part of a system which further comprises a cellular phone with which the device is in wireless communication. In an example, a device for recording biometric information from a person's head can be part of a system which further comprises a laptop computer with which the device is in wireless communication. In an example, a device for recording biometric information from a person's head can be part of a system which further comprises a smart watch or ring with which the device is in wireless communication. In an example, brainwaves can be analyzed by analyzing frequency of pattern repetition, frequency band or range of pattern repetition, recurring amplitude, wave phase, and/or waveform. In an example, electromagnetic signals from eye blinks, eye flutters, or other eye movements can be removed (e.g. filtered out) prior to the analysis of brainwave patterns.

In an example, a brainwave pattern can be modeled as a composite of multiple sine waves. In an example, brainwaves can be decomposed and analyzed using Fourier Transformation. In another example, data from a plurality of electrodes can be analyzed to track changes in brainwaves in a single frequency band, changes in brainwaves in multiple frequency bands, or changes in brainwaves in a first frequency band relative to those in a second frequency band. A torus shape can be geometrically-modeled by revolving a convex shape (e.g. a circle, an ellipse, an oblate circle, an egg shape, or a convex polygon) in three-dimensional space around an axis of revolution which is coplanar with the convex shape. In an example, a circumaural housing can further comprise a half-torus-shaped (e.g. like half of a bagel) low-durometer (e.g. soft, compressible, and/or compliant) ring which encircles a person's auricle, wherein there are a plurality of electrodes distributed around the circumference of the ring. In an example, parameters used to identify a pattern of brainwave activity can be selected from the group consisting of: shape of one or more spikes; amplitude, maximum, or minimum of one or more spikes; frequency of multiple spikes; pattern covariation; pattern entropy; pattern signature; first and second order differentials; polynomial modeling; and composite sine wave modeling.

In another example, Alpha brainwaves or other rhythmic, cyclical, and/or repeating electromagnetic signals associated with brain activity can be measured and analyzed within a frequency band selected from the group consisting of: 7-13 Hz, 7-14 Hz, 8-12 Hz, 8-13 Hz, 7-11 Hz, 8-10 Hz, and 8-10 Hz. In an example, brainwaves can be measured and analyzed using a subset and/or combination of five clinical frequency bands: Delta, Theta, Alpha, Beta, and Gamma. In another example, data from a plurality of electrodes can be analyzed to measure changes in the frequency, power, and/or wave shape of brainwaves in the Delta band. In an example, Delta brainwaves (or other rhythmic, cyclical, and/or repeating electromagnetic signals associated with brain activity) can be measured and analyzed within a frequency band selected from the group consisting of: 0.5-3.5 Hz, 0.5-4 Hz, 1-3 Hz, 1-4 Hz, and 2-4 Hz. In an example, Gamma brainwaves or other rhythmic, cyclical, and/or repeating electromagnetic signals associated with brain activity can be measured and analyzed within a frequency band selected from the group consisting of: 30-100 Hz, 35-100 Hz, 40-100 Hz, and greater than 30 Hz.

In an example, data from a plurality of electrodes can be analyzed using a method selected from the group consisting of: Cluster Analysis, Kernel Estimation, Probit Model, Feature Vector Analysis (FVA), Multi-Channel Covariance Analysis, Trained Bayes Classifier, Factor Analysis (FA), and Mean Power. In an example, data from a plurality of electrodes can be analyzed using a method selected from the group consisting of: Signal Averaging, Carlavian Curve Analysis (CCA), Inter-Montage Power Mean, Power Spectral Density, Discrete Fourier transform (DFT), Logit Model, Signal Decomposition, and Discriminant Analysis (DA).

In another example, data from a plurality of electrodes can be analyzed using a method selected from the group consisting of: Multivariate Parametric Classifiers, Wavelet Analysis, Artificial Neural Network (ANN), Hidden Markov Model (HMM), Neural Network, Correlation, Laplacian Filter, Quadratic Minimum Distance Classifier. In an example, data from a plurality of electrodes can be analyzed using a method selected from the group consisting of: Maximum Likelihood, Time Domain Analysis, Bayesian statistical method, Inter-Band Power Ratio, and Non-negative Matrix Factorization (NMF).

In an example, a device can emit sounds and/or music which help a person to change their brain activity from a first pattern to a second pattern. In another example, a pair of biauricular headphones with electrodes can be used for neurostimulation and/or neuromodulation (instead of monitoring biometric signals). In an example, analysis of data from a plurality of electrodes can enable a person to control a computer and/or other device via brain activity. In an example, electrodes can be used to monitor electromagnetic signals from a person's nervous system.

Having concluded the introductory section, this disclosure now provides detailed descriptions of the examples shown in FIGS. 1 through 16.

FIG. 1 shows a left-side view of an example of headphones with electrodes comprising: a left-side circumaural housing 101 (e.g. a speaker housing, car pad, car cushion, and/or ear cuff) which encircles and covers a person's left auricle; a right-side circumaural housing (e.g. a speaker housing, ear pad, car cushion, and/or ear cuff) which encircles and covers the person's right auricle; an upper band 103 which loops and/or curves over the upper half of the person's head from the left-side circumaural housing to the right-side circumaural housing; a first plurality of electrodes, including electrode 102, on the left-side circumaural housing which record biometric signals (e.g. brainwaves) from the person's brain; a second plurality of electrodes on the right-side circumaural housing which record biometric signals from the person's brain; and a third plurality of electrodes, including electrode 104, on the upper band which record biometric signals from the person's brain. The right side of the headphones are not shown in this figure, but it is assumed that the right side of the headphones is symmetric to the left side. In an example, a device can be shaped like headphones which cover a person's ears and loop over the top of their head. In an example, a device can comprise a plurality of electrodes which are located at a subset of the following placement sites: CP1, CP2, CP3, CP4, CP5, CP6, CPz, FC1, FC2, FC3, FC4, FC5, FC6, FCz, O1, O2, Oz, P7, P8, PO7, PO8, TP7 and TP8. Relevant variations discussed elsewhere in this disclosure or in priority-linked disclosures can also be applied to this example.

Figure 2:
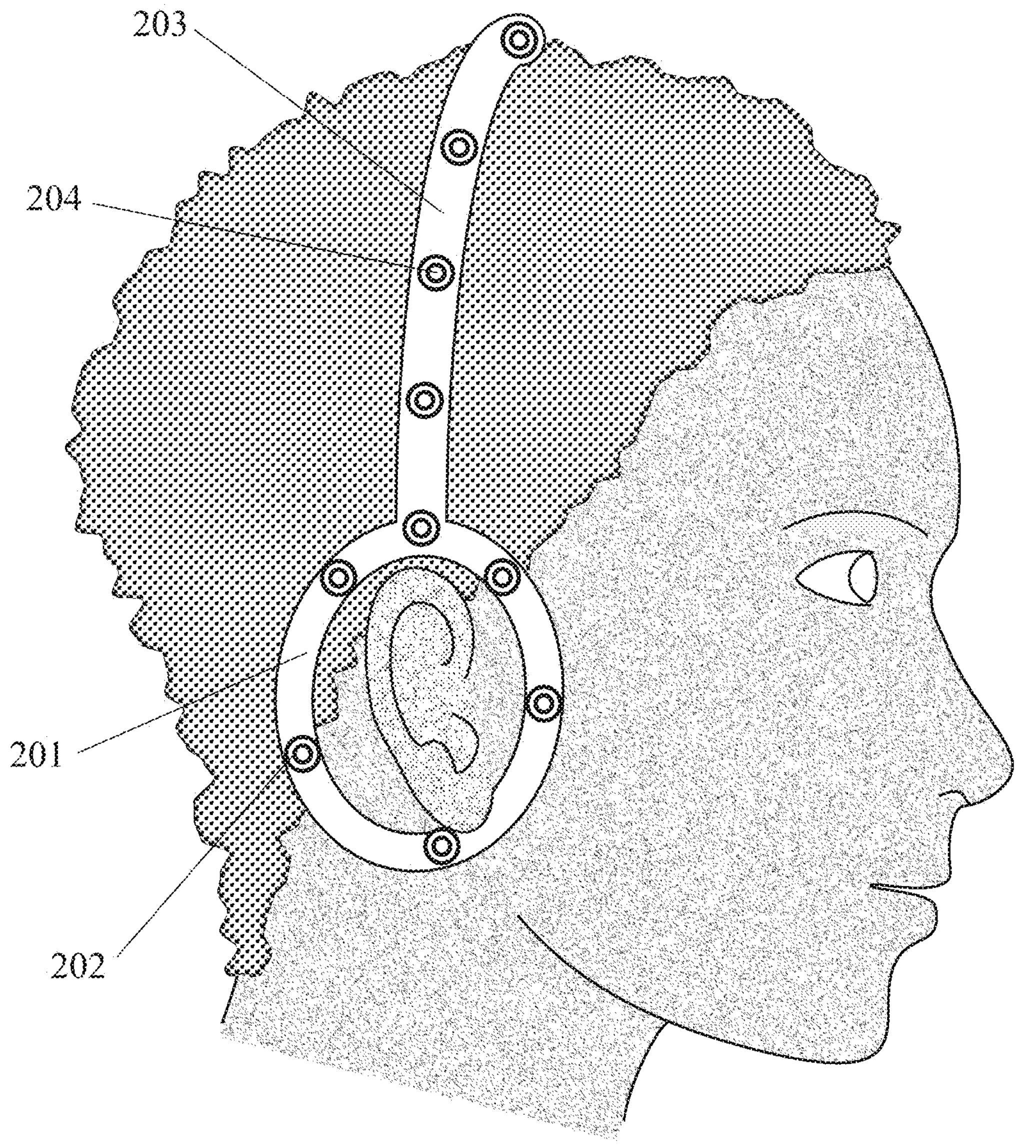
FIG. 2 shows an example of a biauricular headset with an upper band and electrodes.

FIG. 2 shows a left-side view of an example of a biauricular headset with electrodes comprising: a left-side circumaural housing 201 (e.g. annular and/or toroidal band, car cuff, or ear cushion) which encircles a person's left auricle; a right-side circumaural housing (e.g. annular and/or toroidal band, ear cuff, or ear cushion) which encircles the person's right auricle; an upper band 203 which loops and/or curves over the upper half of the person's head from the left-side circumaural housing to the right-side circumaural housing; a first plurality of electrodes, including electrode 202, on the left-side circumaural housing which record biometric signals (e.g. brainwaves) from the person's brain; a second plurality of electrodes on the right-side circumaural housing which record biometric signals from the person's brain; and a third plurality of electrodes, including electrode 204, on the upper band which record biometric signals from the person's brain. The right side of the headset is not shown in this figure, but it is assumed that the right side of the headset is symmetric to the left side.

In an example, a headset device can comprise: an upper loop (e.g. upper band) which loops over a person's head from one ear to the other and holds at least one first electrode; and an ear loop (e.g. circumaural housing) which encircles the person's ear and holds at least one second electrode. In an example, at least one second electrode can be located at an electrode position selected from the group consisting of TP9, TP7, T9, and T7. In an example, a headset device can comprise: an upper loop (e.g. upper band) which loops over the top of a person's and holds at least one first electrode; a front ear arm/portion which curves around the front of the person's ear and holds at least one second electrode (located at an electrode position selected from the group consisting of T9 and T7); and a rear ear arm/portion which curves around the rear of the person's ear and holds at least one third electrode (located at an electrode position selected from the group consisting of P9, TP9, TP7, and T7). Relevant variations discussed elsewhere in this disclosure or in priority-linked disclosures can also be applied to this example.

Figure 3:
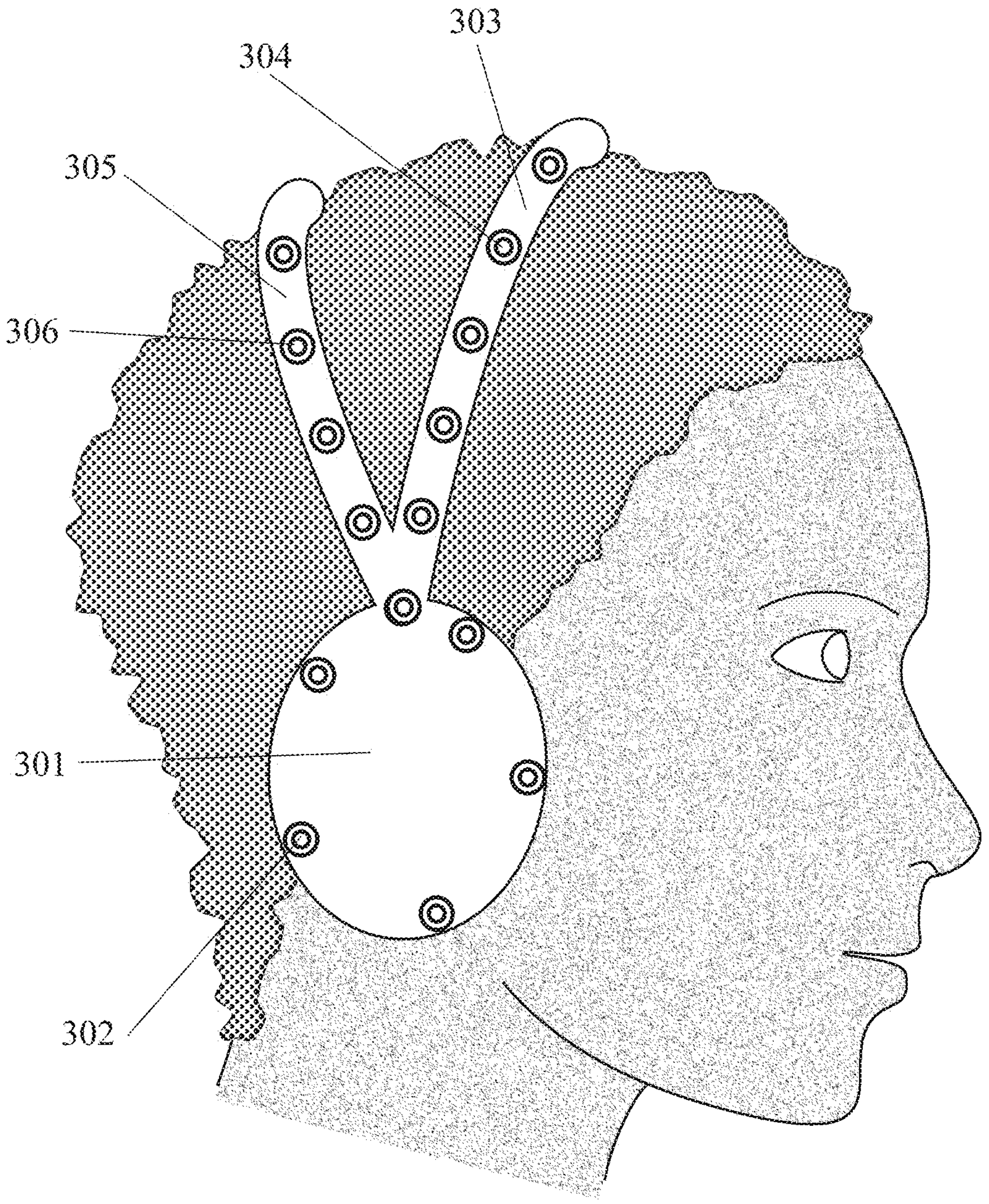
FIG. 3 shows an example of headphones with a bifurcated upper band and electrodes.

FIG. 3 shows a left-side view of an example of headphones with electrodes comprising: a left-side circumaural housing 301 (e.g. a speaker housing, ear pad, ear cushion, and/or ear cuff) which encircles and covers a person's left auricle; a right-side circumaural housing (e.g. a speaker housing, ear pad, ear cushion, and/or ear cuff) which encircles and covers the person's right auricle; a bifurcated upper band with diverging branches 303 and 305 which loop and/or curve over the upper half of the person's head from the left-side circumaural housing to the right-side circumaural housing; a first plurality of electrodes, including electrode 302, on the left-side circumaural housing which record biometric signals (e.g. brainwaves) from the person's brain; a second plurality of electrodes on the right-side circumaural housing which record biometric signals from the person's brain; and a third plurality of electrodes, including electrodes 304 and 306, on the bifurcated upper band which record biometric signals from the person's brain. The right side of the headphones are not shown in this figure, but it is assumed that the right side of the headphones is symmetric to the left side.

In an example, a headphones device can include two branches of a bifurcated upper band which loop over the top of a person's head. Having a band with two branches instead of a single band increases the range of electrodes covering the person's head. In an example, these two branches can provide coverage of the person's parietal and upper occipital lobes. In an example, bottom portions of the two branches can converge at locations just above (e.g. within two inches of) the person's ears. In an example, upper portions of the two branches can diverge at an between 20 to 80 degrees as they leave a convergence location to loop around the top of the person's head. Relevant variations discussed elsewhere in this disclosure or in priority-linked disclosures can also be applied to this example.

Figure 4:
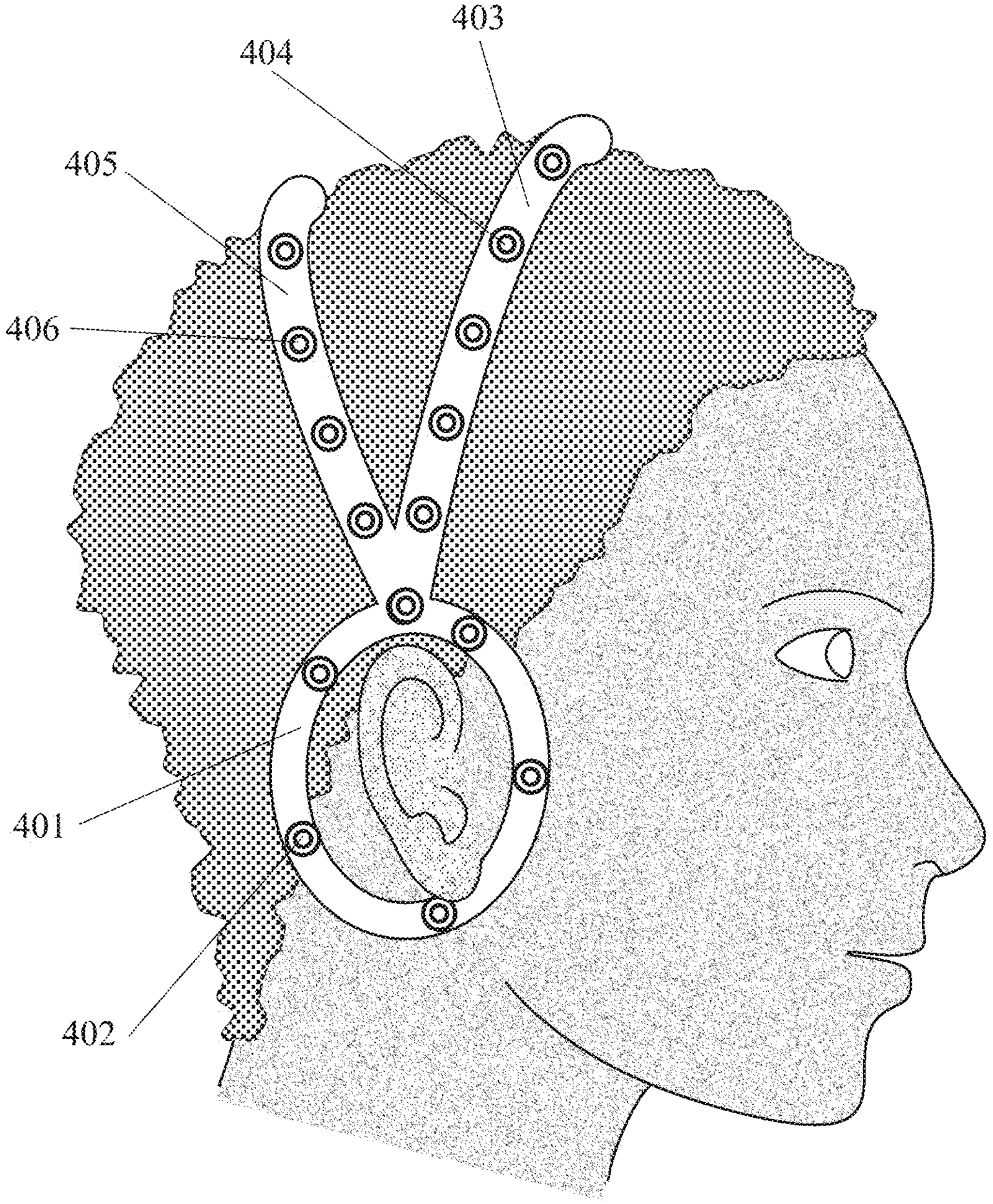
FIG. 4 shows an example of a biauricular headset with a bifurcated upper band and electrodes.

FIG. 4 shows a left-side view of an example of a biauricular headset with electrodes comprising: a left-side circumaural housing 401 (e.g. annular and/or toroidal band, ear cuff, or ear cushion) which encircles a person's left auricle; a right-side circumaural housing (e.g. annular and/or toroidal band, ear cuff, or ear cushion) which encircles the person's right auricle; a bifurcated upper band with diverging branches 403 and 405 which loop and/or curve over the upper half of the person's head from the left-side circumaural housing to the right-side circumaural housing; a first plurality of electrodes, including electrode 402, on the left-side circumaural housing which record biometric signals (e.g. brainwaves) from the person's brain; a second plurality of electrodes on the right-side circumaural housing which record biometric signals from the person's brain; and a third plurality of electrodes, including electrodes 404 and 406, on the bifurcated upper band which record biometric signals from the person's brain. The right side of the headset is not shown in this figure, but it is assumed that the right side of the headset is symmetric to the left side. Relevant variations discussed elsewhere in this disclosure or in priority-linked disclosures can also be applied to this example.

Figure 5:
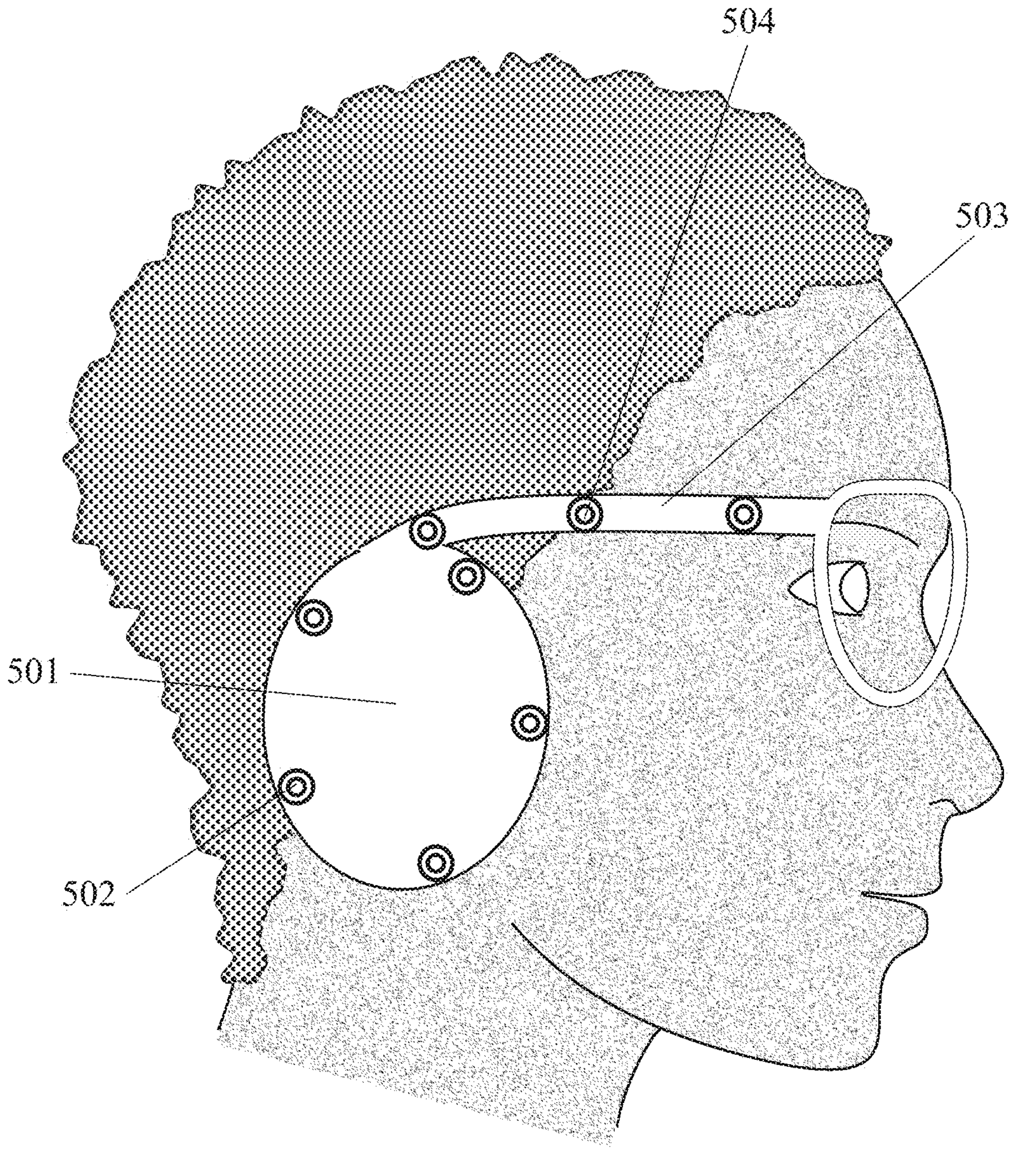
FIG. 5 shows an example of an integrated headphones-and-eyewear device with electrodes.

FIG. 5 shows a left-side view of an example of an integrated headphones-and-eyewear device with electrodes comprising: a left-side circumaural housing 501 (e.g.

speaker housing, ear pad, ear cushion, and/or ear cuff) which encircles and covers a person's left auricle; a right-side circumaural housing (e.g. speaker housing, ear pad, ear cushion, and/or ear cuff) which encircles and covers the person's right auricle; an eyewear frame 503 which spans the person's face from the left-side circumaural housing to the right-side circumaural housing; a first plurality of electrodes, including electrode 502, on the left-side circumaural housing which record biometric signals (e.g. brainwaves) from the person's brain; a second plurality of electrodes on the right-side circumaural housing which record biometric signals from the person's brain; and a third plurality of electrodes, including electrode 504, on the eyewear frame which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 6:
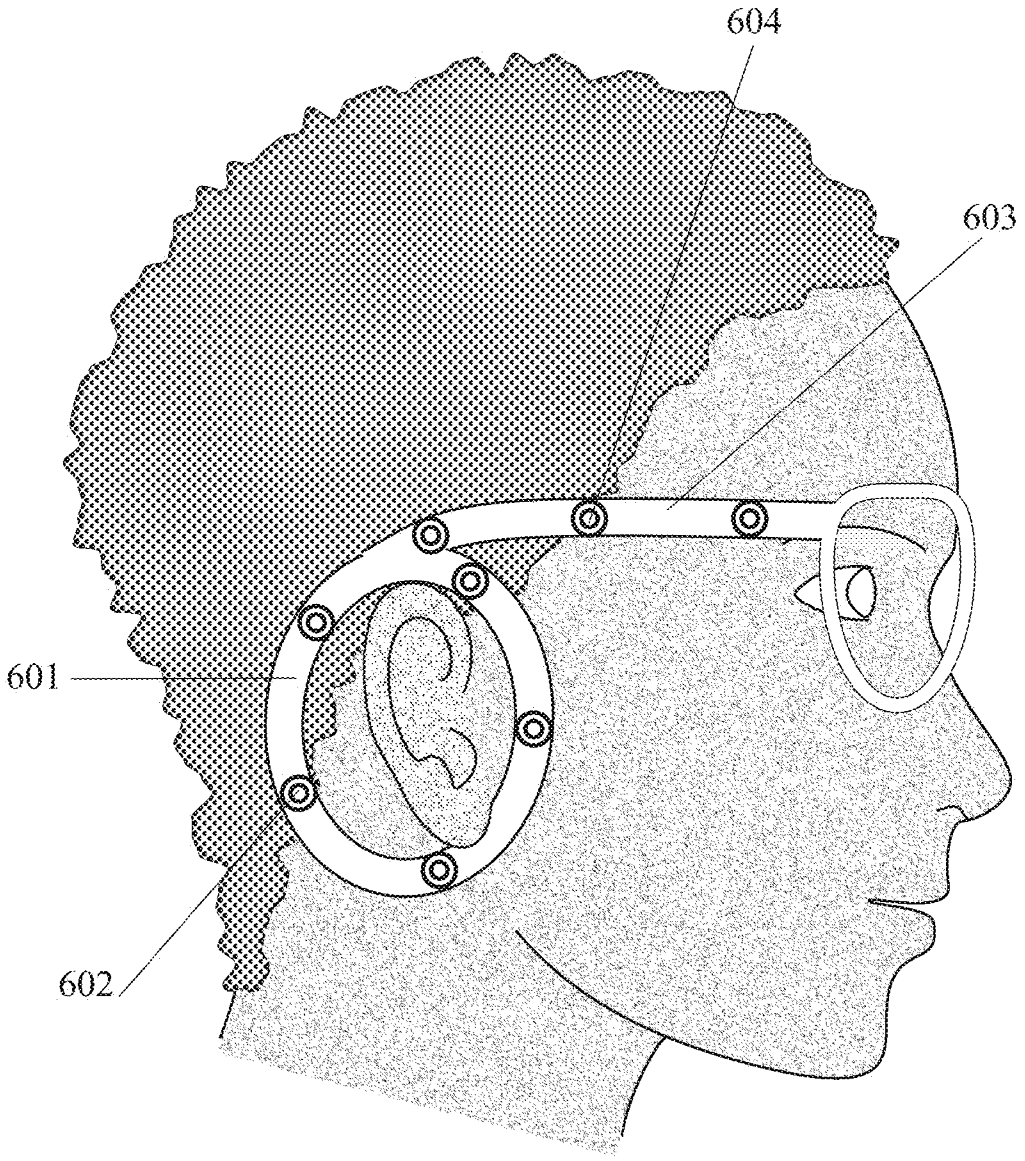
FIG. 6 shows an example of an integrated headset-and-eyewear device with electrodes.

FIG. 6 shows a left-side view of an example of an integrated headset-and-eyewear device with electrodes comprising: a left-side circumaural housing 601 (e.g. annular and/or toroidal band, ear cuff, or ear cushion) which encircles a person's left auricle; a right-side circumaural housing (e.g. annular and/or toroidal band, ear cuff, or each cushion) which encircles the person's right auricle; an eyewear frame 603 which spans the person's face from the left-side circumaural housing to the right-side circumaural housing; a first plurality of electrodes, including electrode 602, on the left-side circumaural housing which record biometric signals (e.g. brainwaves) from the person's brain; a second plurality of electrodes on the right-side circumaural housing which record biometric signals from the person's brain; and a third plurality of electrodes, including electrode 604, on the eyewear frame which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 7:
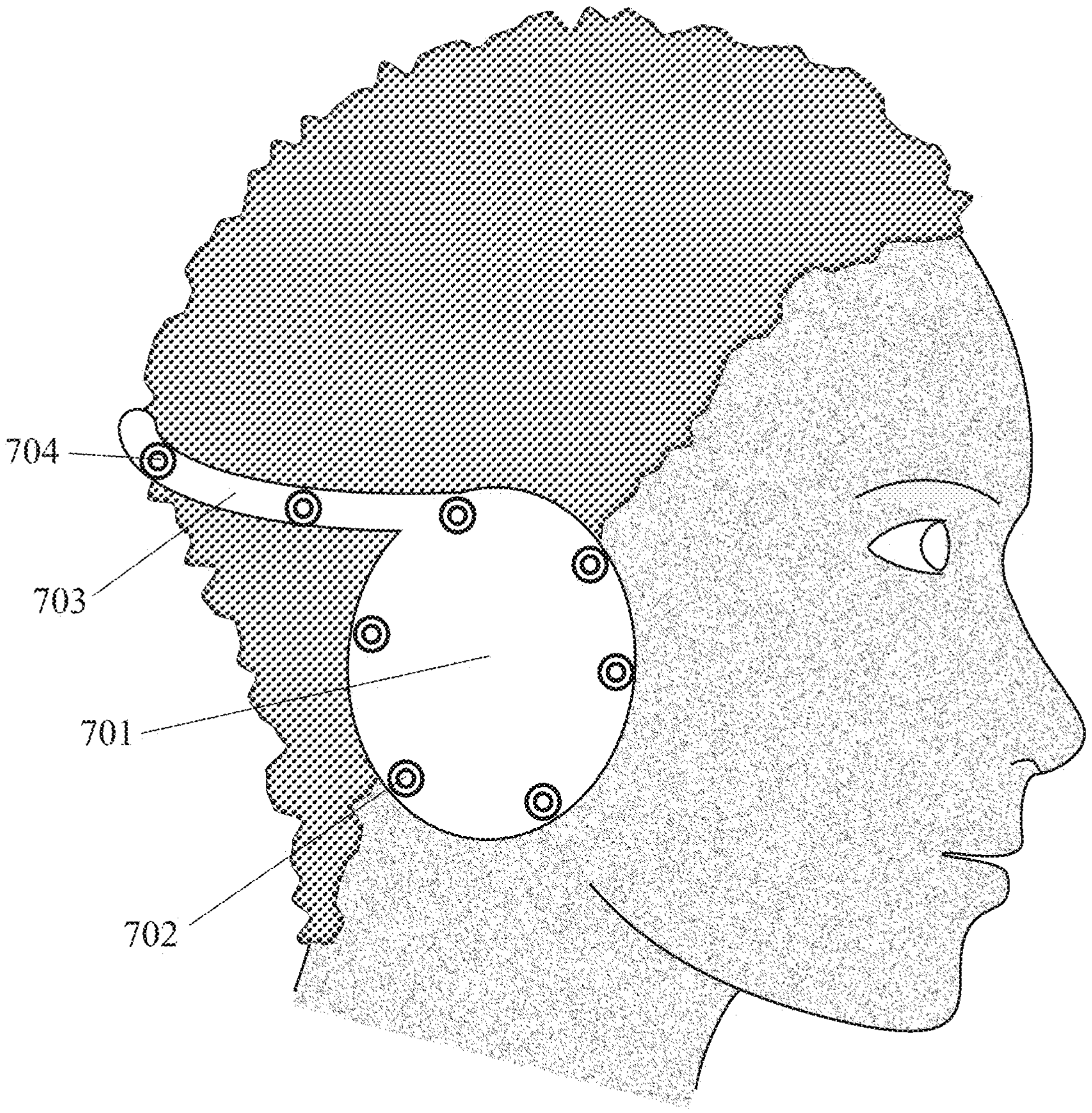
FIG. 7 shows an example of headphones with a posterior band and electrodes.

FIG. 7 shows a left-side view of an example of an integrated headphones-and-posterior-band device with electrodes comprising: a left-side circumaural housing 701 (e.g. speaker housing, ear pad, ear cushion, and/or ear cuff) which encircles and covers a person's left auricle; a right-side circumaural housing (e.g. speaker housing, ear pad, car cushion, and/or ear cuff) which encircles and covers the person's right auricle; a posterior band 703 which loops and/or curves around the posterior half of the person's head from the left-side circumaural housing to the right-side circumaural housing; a first plurality of electrodes, including electrode 702, on the left-side circumaural housing which record biometric signals (e.g. brainwaves) from the person's brain; a second plurality of electrodes on the right-side circumaural housing which record biometric signals from the person's brain; and a third plurality of electrodes, including electrode 704, on the posterior band which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 8:
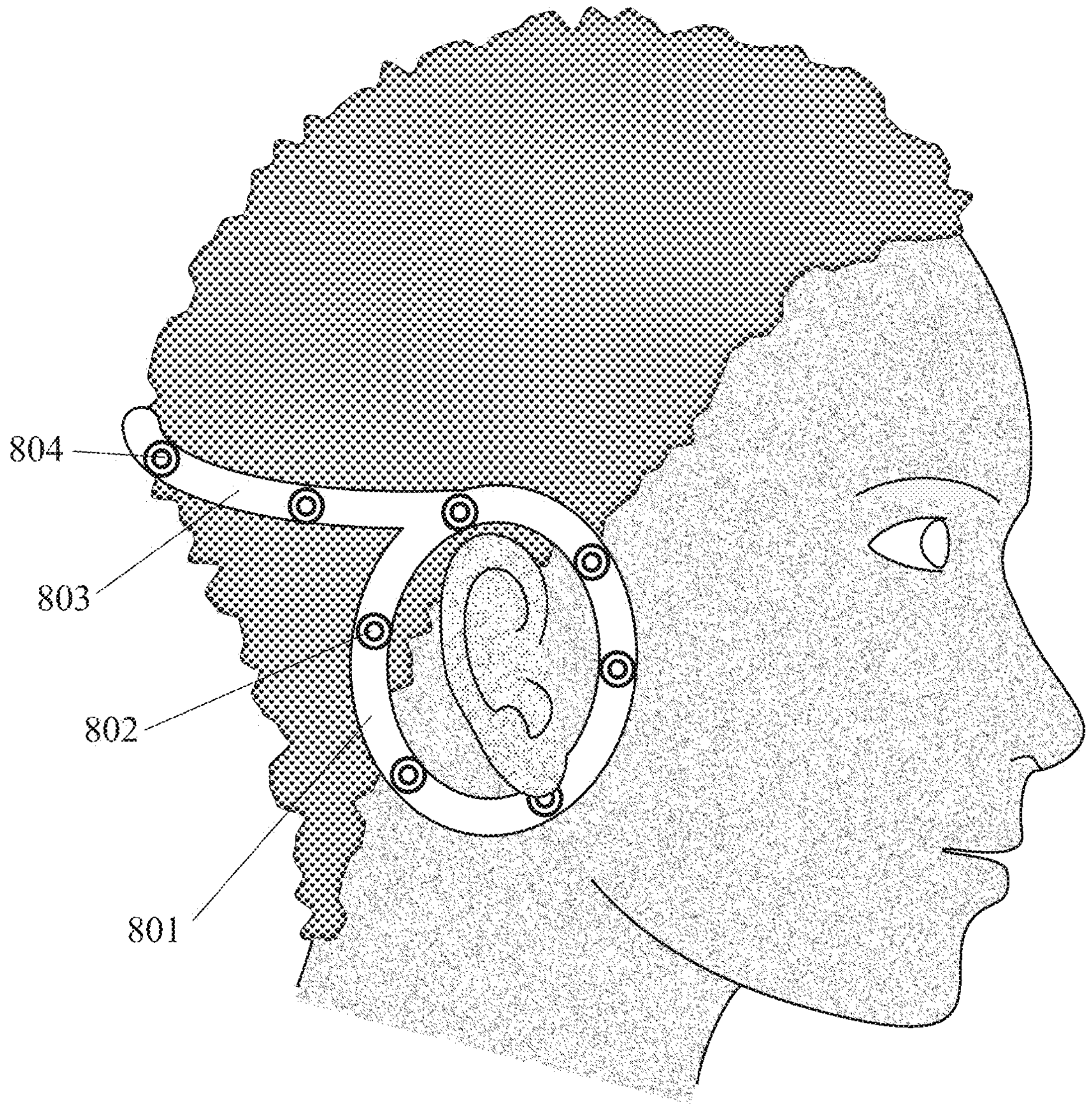
FIG. 8 shows an example of a biauricular headset with a posterior band and electrodes.

FIG. 8 shows a left-side view of an example of an integrated headset-and-posterior-band device with electrodes comprising: a left-side circumaural housing 801 (e.g. annular and/or toroidal band, ear cuff, or ear cushion) which encircles a person's left auricle; a right-side circumaural housing (e.g. annular and/or toroidal band, ear cuff, or ear cushion) which encircles the person's right auricle; a posterior band 803 which loops and/or curves around the posterior half of the person's head from the left-side circumaural housing to the right-side circumaural housing; a first plurality of electrodes, including electrode 802, on the left-side circumaural housing which record biometric signals (e.g. brainwaves) from the person's brain; a second plurality of electrodes on the right-side circumaural housing which record biometric signals from the person's brain; and a third plurality of electrodes, including electrode 804, on the posterior band which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 9:
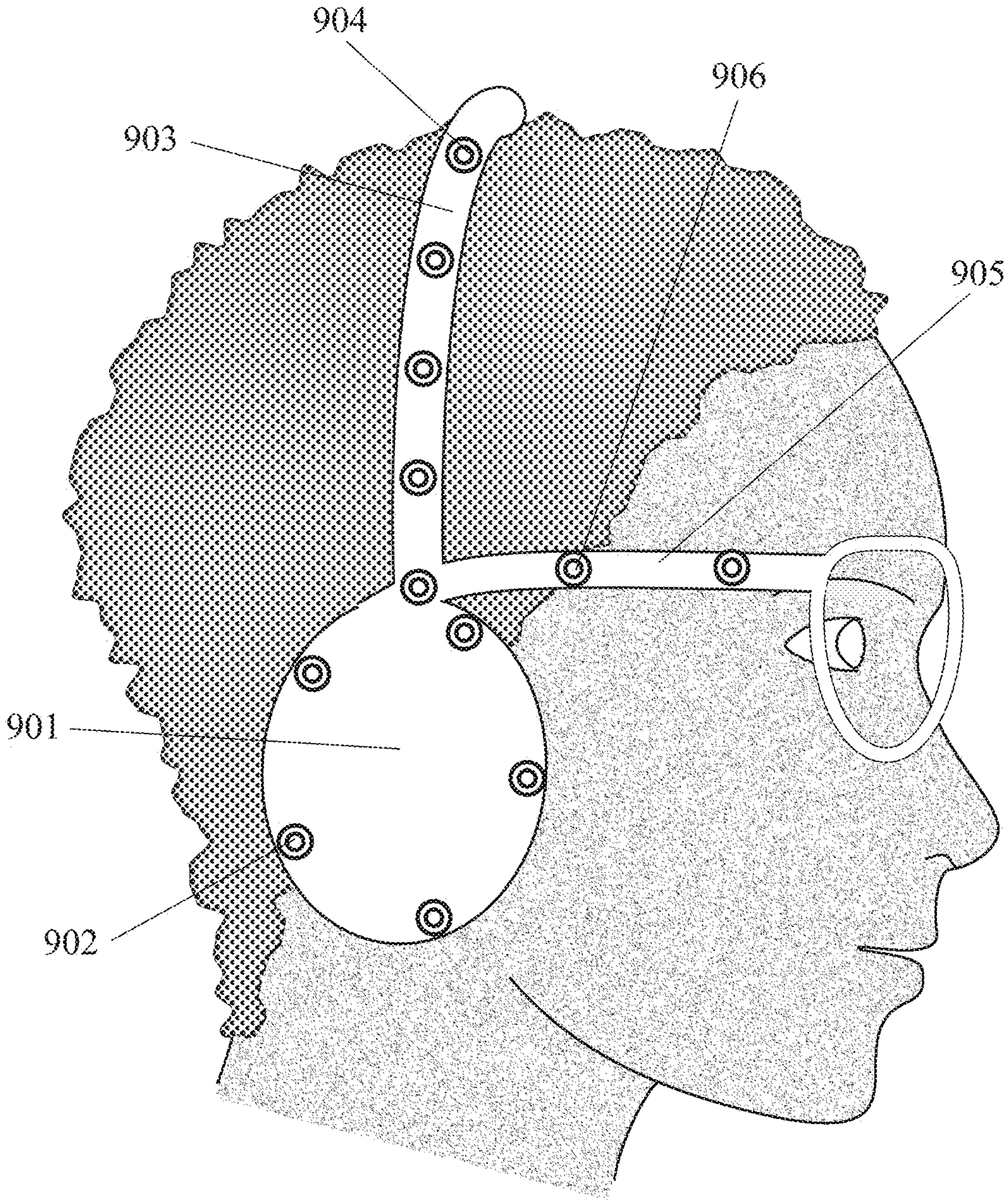
FIG. 9 shows an example of an integrated headphones-and-upper-band-and-eyewear device with electrodes.

FIG. 9 shows a left-side view of an example of an integrated headphones-and-eyewear device with electrodes comprising: a left-side circumaural housing 901 (e.g. speaker housing, ear pad, ear cushion, and/or ear cuff) which encircles and covers a person's left auricle; a right-side circumaural housing (e.g. speaker housing, ear pad, ear cushion, and/or ear cuff) which encircles and covers the person's right auricle; an upper band 903 which loops and/or curves around the upper half of the person's head from the left-side circumaural housing to the right-side circumaural housing; an eyewear frame 905 which spans the person's face from the left-side circumaural housing to the right-side circumaural housing; a first plurality of electrodes, including electrode 902, on the left-side circumaural housing which record biometric signals (e.g. brainwaves) from the person's brain; a second plurality of electrodes on the right-side circumaural housing which record biometric signals from the person's brain; a third plurality of electrodes, including electrode 904, on the upper band which record biometric signals from the person's brain; and a fourth plurality of electrodes, including electrode 906, on the eyewear frame which record biometric signals from the person's brain. The right side of the integrated device is not shown in this figure, but it is assumed that the right side of the integrated device is symmetric to the left side. In an example, a device can integrate both eyewear and headphone components. In an example, a posterior portion of an integrated device can comprise a pair of headphones which covers the person's ears and loops over the top of the person's head and an anterior portion of the integrated device can comprise eyewear. In an example, an eyewear frame and headphones can be integrated into a single device. Relevant variations discussed elsewhere in this disclosure or in priority-linked disclosures can also be applied to this example.

Figure 10:
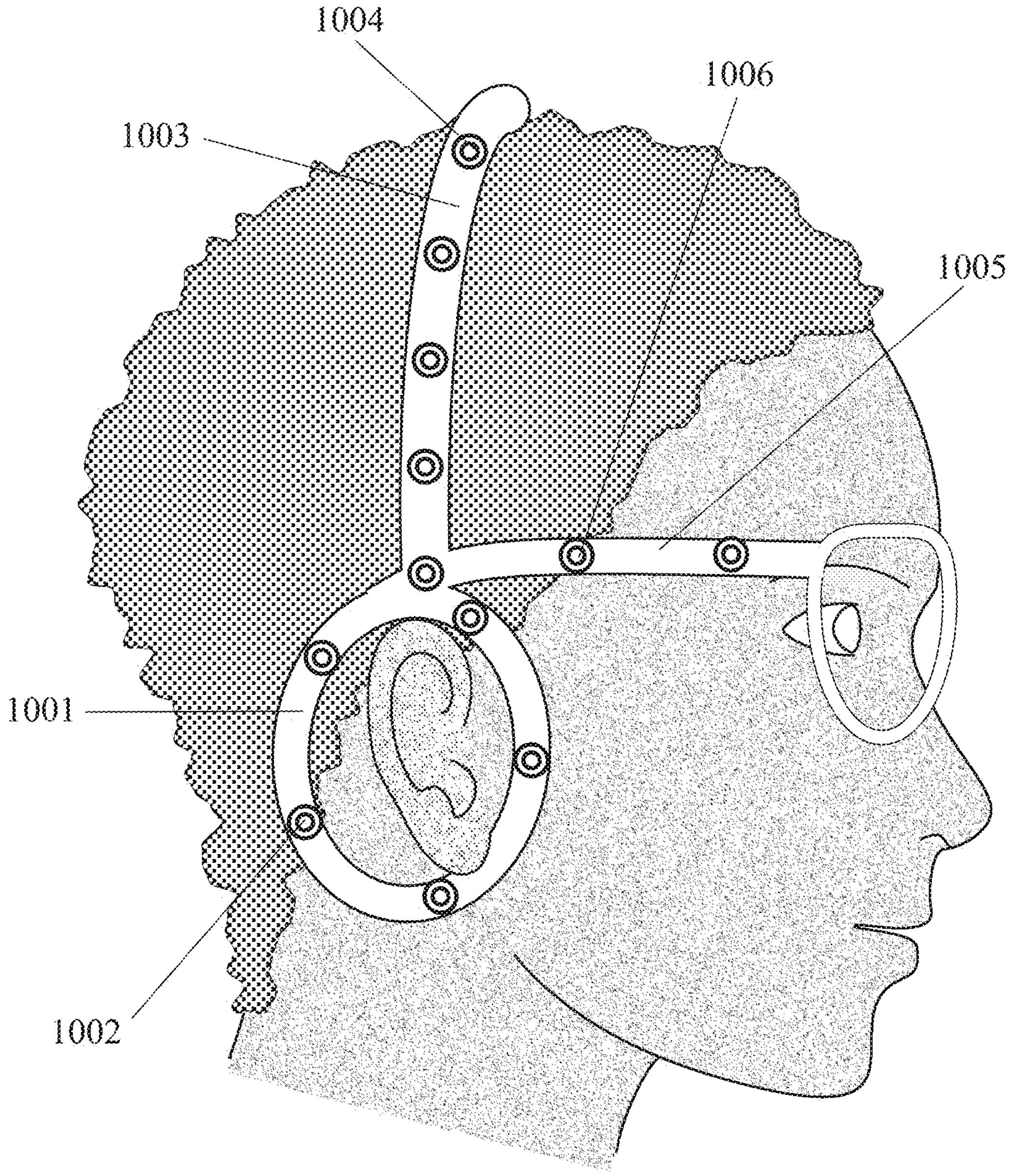
FIG. 10 shows an example of an integrated headset-and-upper-band-and-eyewear device with electrodes.

FIG. 10 shows a left-side view of an example of an integrated headset-and-eyewear device with electrodes comprising: a left-side circumaural housing 1001 (e.g. annular and/or toroidal band, ear cuff, or ear cushion) which encircles a person's left auricle; a right-side circumaural housing (e.g. annular and/or toroidal band, ear cuff, or ear cushion) which encircles the person's right auricle; an upper band 1003 which loops and/or curves around the upper half of the person's head from the left-side circumaural housing to the right-side circumaural housing; an eyewear frame 1005 which spans the person's face from the left-side circumaural housing to the right-side circumaural housing; a first plurality of electrodes, including electrode 1002, on the left-side circumaural housing which record biometric signals (e.g. brainwaves) from the person's brain; a second plurality of electrodes on the right-side circumaural housing which record biometric signals from the person's brain; a third plurality of electrodes, including electrode 1004, on the upper band which record biometric signals from the person's brain; and a fourth plurality of electrodes, including electrode 1006, on the eyewear frame which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 11:
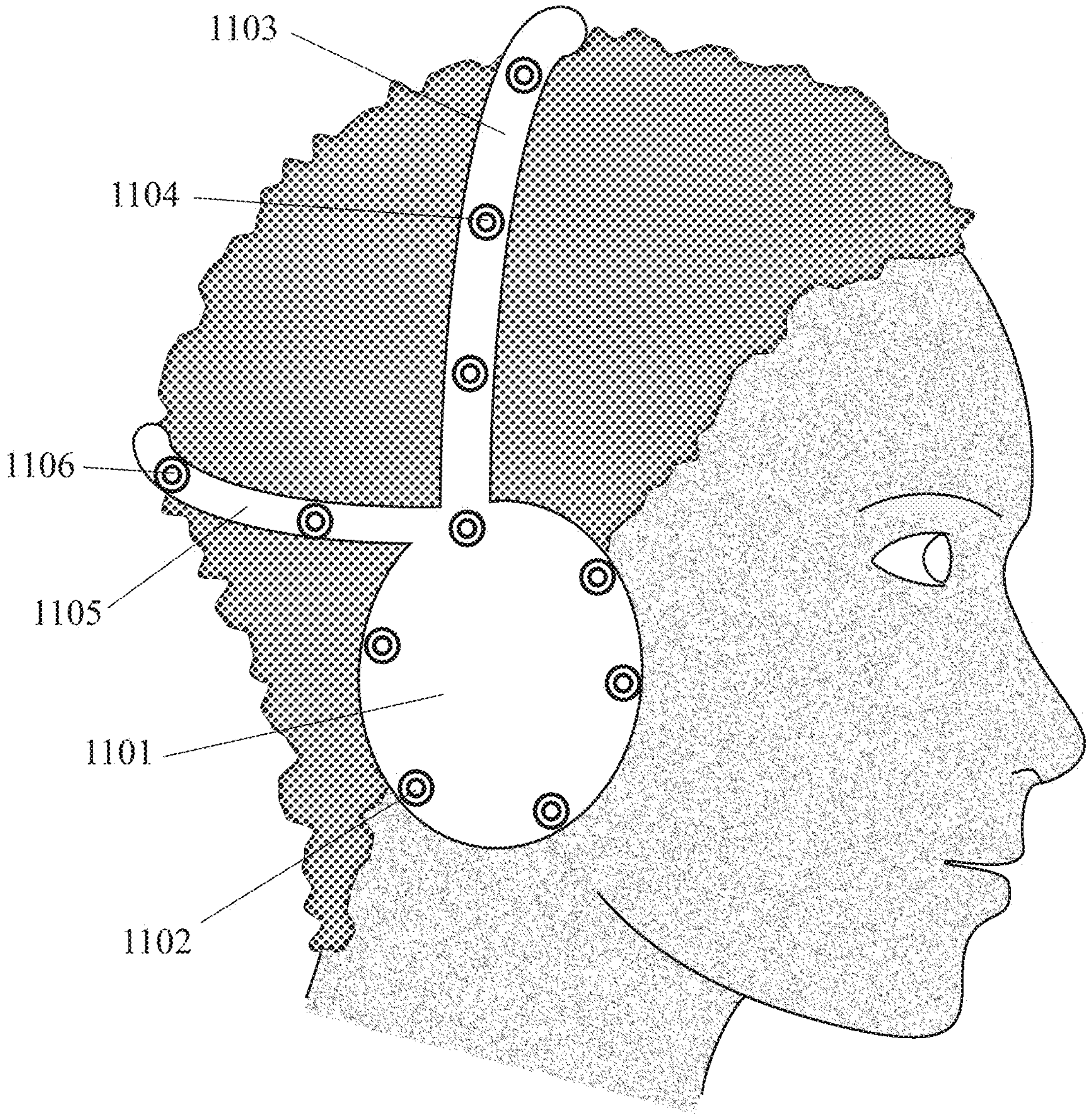
FIG. 11 shows an example of headphones with an upper band, posterior band, and electrodes.

FIG. 11 shows a left-side view of an example of an integrated headphones-and-posterior-band device with electrodes comprising: a left-side circumaural housing 1101 (e.g. speaker housing, ear pad, car cushion, and/or ear cuff) which encircles and covers a person's left auricle; a right-side circumaural housing (e.g. speaker housing, car pad, ear cushion, and/or ear cuff) which encircles and covers the person's right auricle; an upper band 1103 which loops and/or curves around the upper half of the person's head from the left-side circumaural housing to the right-side circumaural housing; a posterior band 1105 which loops and/or curves around the posterior half of the person's head from the left-side circumaural housing to the right-side circumaural housing; a first plurality of electrodes, including electrode 1102, on the left-side circumaural housing which record biometric signals (e.g. brainwaves) from the person's brain; a second plurality of electrodes on the right-side circumaural housing which record biometric signals from the person's brain; a third plurality of electrodes, including electrode 1104, on the upper band which record biometric signals from the person's brain; and a fourth plurality of electrodes, including electrode 1106, on the posterior band which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 12:
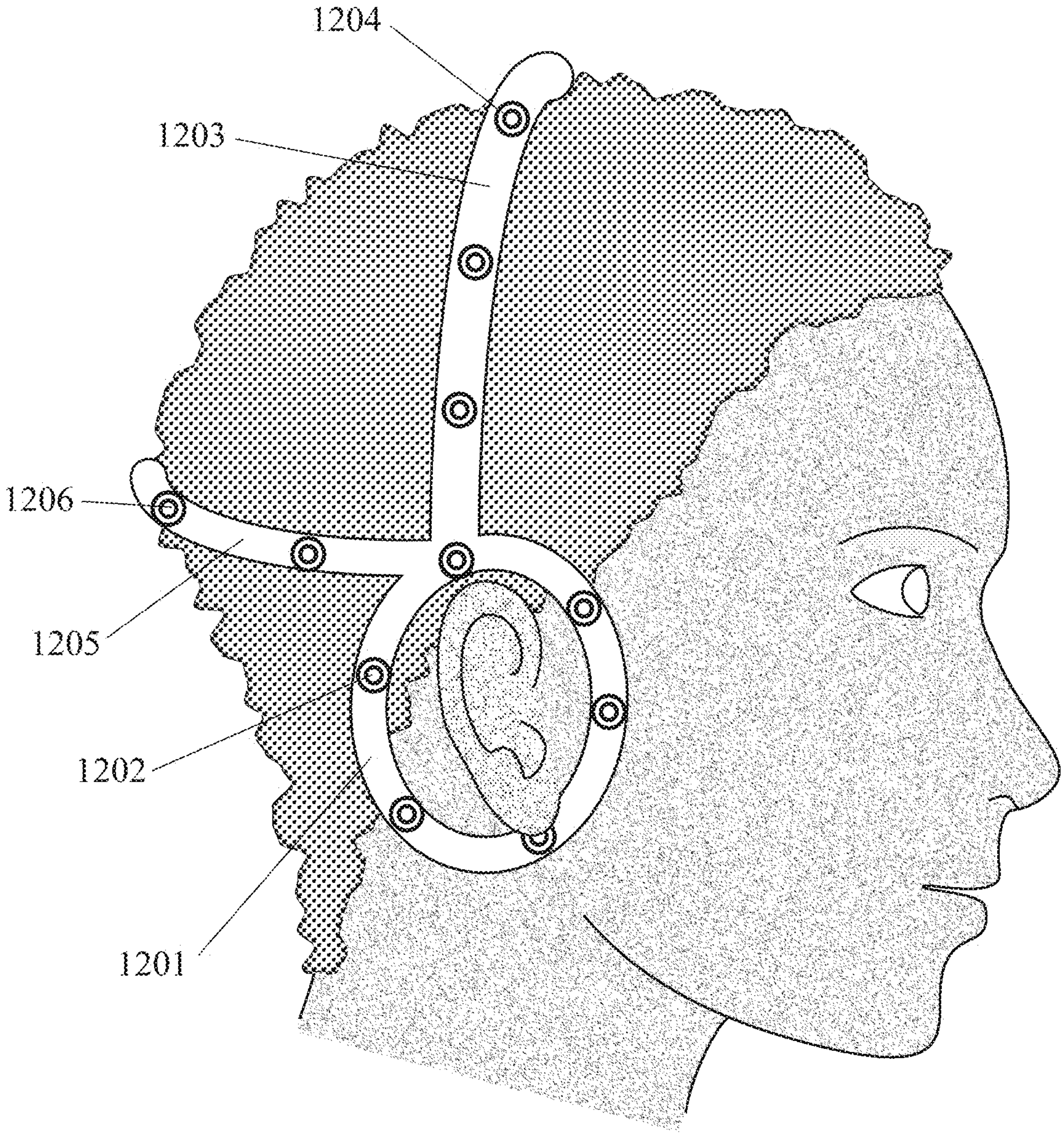
FIG. 12 shows an example of a biauricular headset with an upper band, a posterior band, and electrodes.

FIG. 12 shows a left-side view of an example of an integrated headset-and-posterior-band device with electrodes comprising: a left-side circumaural housing 1201 (e.g. annular and/or toroidal band, car cuff, or ear cushion) which encircles a person's left auricle; a right-side circumaural housing (e.g. annular and/or toroidal band, car cuff, or ear cushion) which encircles the person's right auricle; an upper band 1203 which loops and/or curves around the upper half of the person's head from the left-side circumaural housing to the right-side circumaural housing; a posterior band 1205 which loops and/or curves around the posterior half of the person's head from the left-side circumaural housing to the right-side circumaural housing; a first plurality of electrodes, including electrode 1202, on the left-side circumaural housing which record biometric signals (e.g. brainwaves) from the person's brain; a second plurality of electrodes on the right-side circumaural housing which record biometric signals from the person's brain; a third plurality of electrodes, including electrode 1204, on the upper band which record biometric signals from the person's brain; and a fourth plurality of electrodes, including electrode 1206, on the posterior band which record biometric signals from the person's brain. The right side of the integrated device is not shown in this figure, but it is assumed that the right side of the integrated device is symmetric to the left side. Relevant variations discussed elsewhere in this disclosure or in priority-linked disclosures can also be applied to this example.

Figure 13:
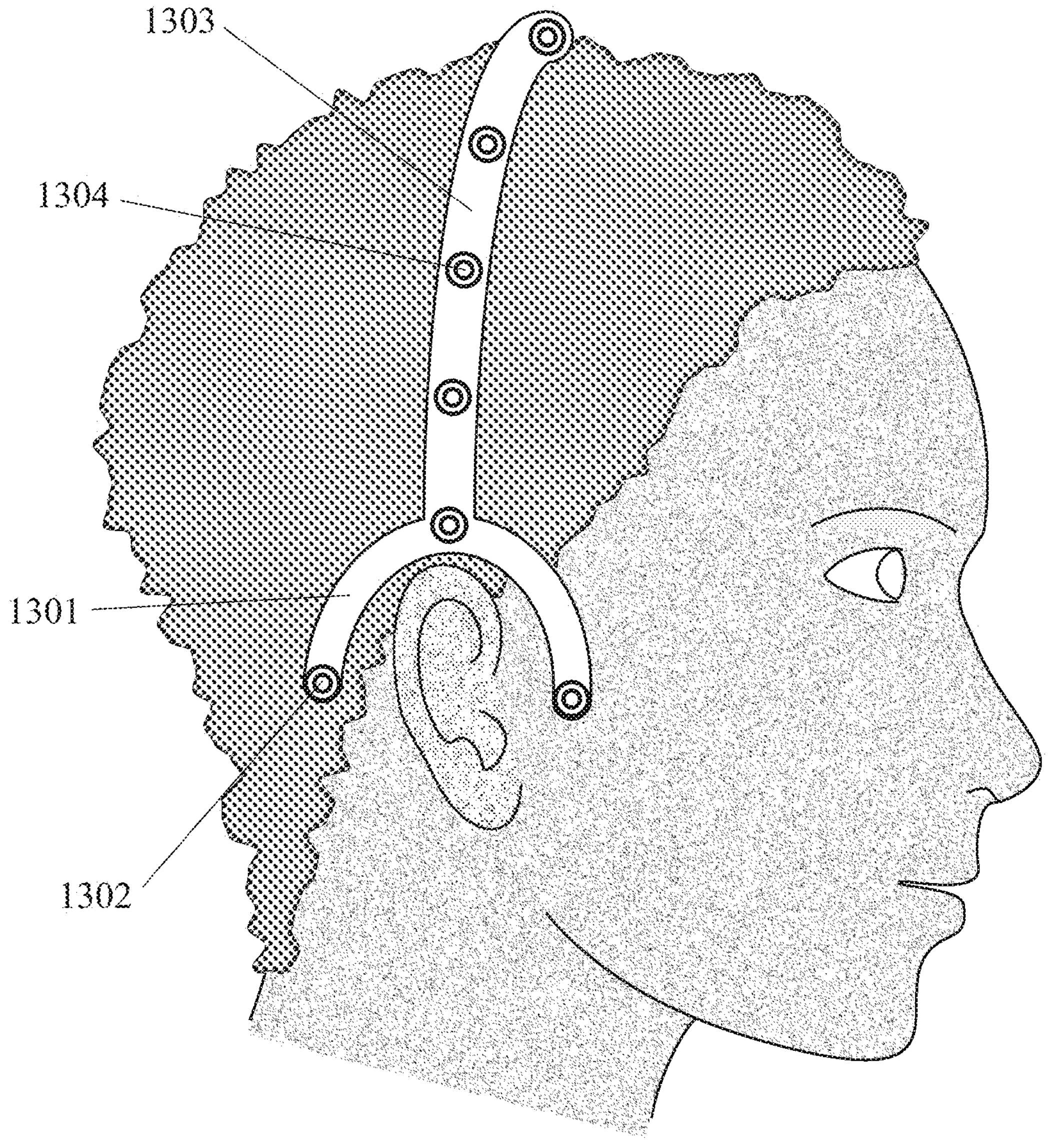
FIG. 13 shows an example of a headset with semi-circumaural housings, an upper band, and electrodes.

FIG. 13 shows a left-side view of an example of an headset device with electrodes comprising: a left-side partially-circumaural housing 1301 (e.g. partial-annular and/or partial-toroidal band, ear cuff, or ear cushion) which encircles between 30% and 60% of a person's left auricle; a right-side partially-circumaural housing (e.g. partial-annular and/or partial-toroidal band, ear cuff, or each cushion) which encircles between 30% and 60% of the person's right auricle; an upper band 1303 which loops and/or curves over the upper half of the person's head from the left-side partially-circumaural housing to the right-side partially-circumaural housing; a first plurality of electrodes, including electrode 1302, on the left-side partially-circumaural housing which record biometric signals (e.g. brainwaves) from the person's brain; a second plurality of electrodes on the right-side partially-circumaural housing which record biometric signals from the person's brain; and a third plurality of electrodes, including electrode 1304, on the upper band which record biometric signals from the person's brain. The right side of the headset device is not shown in this figure, but it is assumed that the right side of the headset device is symmetric to the left side. Relevant variations discussed elsewhere in this disclosure or in priority-linked disclosures can also be applied to this example.

Figure 14:
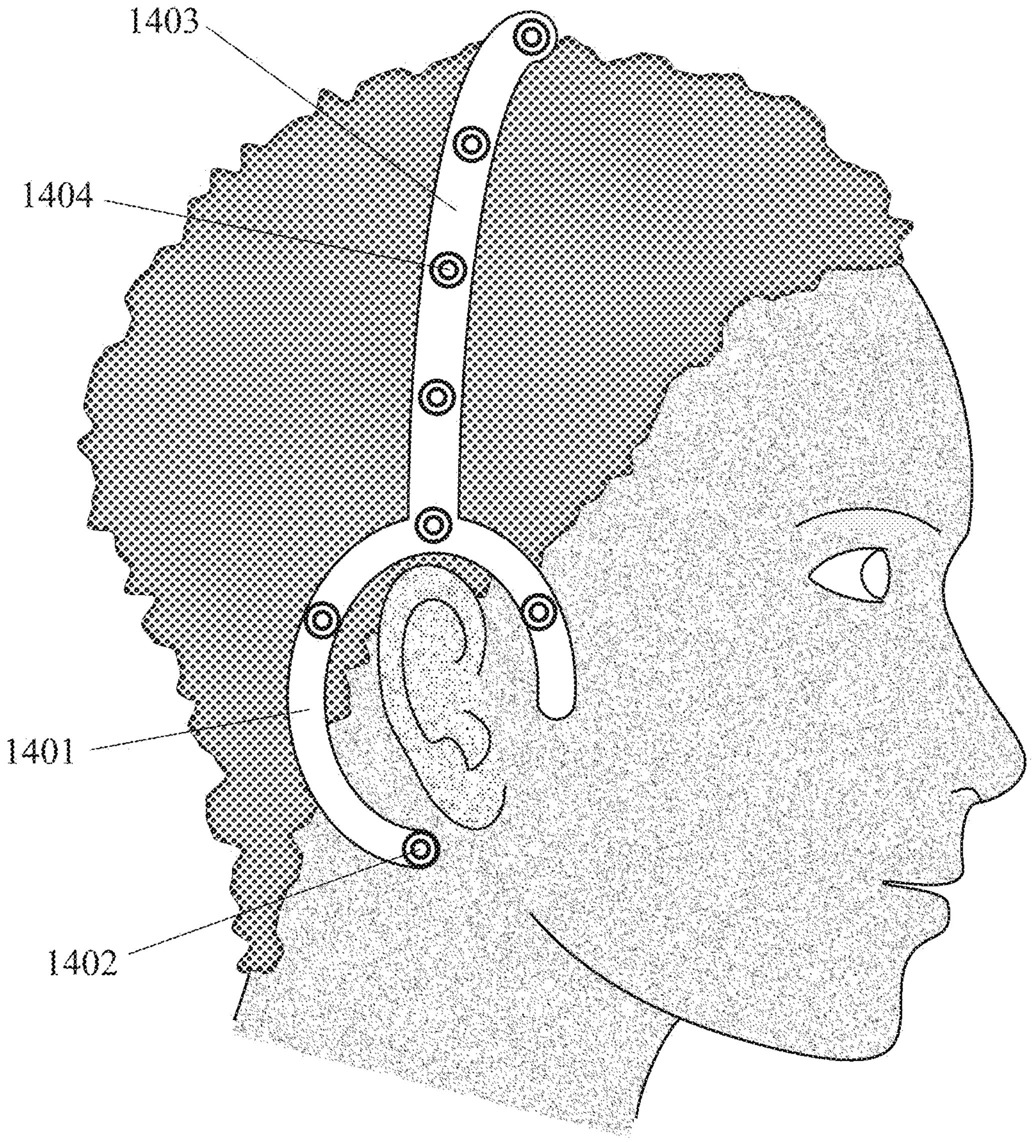
FIG. 14 shows an example of a headset with partially-circumaural housings, an upper band, and electrodes.

FIG. 14 shows a left-side view of an example of an headset device with electrodes comprising: a left-side partially-circumaural housing 1401 (e.g. partial-annular and/or partial-toroidal band, ear cuff, or ear cushion) which encircles between 50% and 90% of a person's left auricle; a right-side partially-circumaural housing (e.g. partial-annular and/or partial-toroidal band, ear cuff, or each cushion) which encircles between 50% and 90% of the person's right auricle; an upper band 1403 which loops and/or curves over the upper half of the person's head from the left-side partially-circumaural housing to the right-side partially-circumaural housing; a first plurality of electrodes, including electrode 1402, on the left-side partially-circumaural housing which record biometric signals (e.g. brainwaves) from the person's brain; a second plurality of electrodes on the right-side partially-circumaural housing which record biometric signals from the person's brain; and a third plurality of electrodes, including electrode 1404, on the upper band which record biometric signals from the person's brain. The right side of the headset device is not shown in this figure, but it is assumed that the right side of the headset device is symmetric to the left side. Relevant variations discussed elsewhere in this disclosure or in priority-linked disclosures can also be applied to this example.

Figure 15:
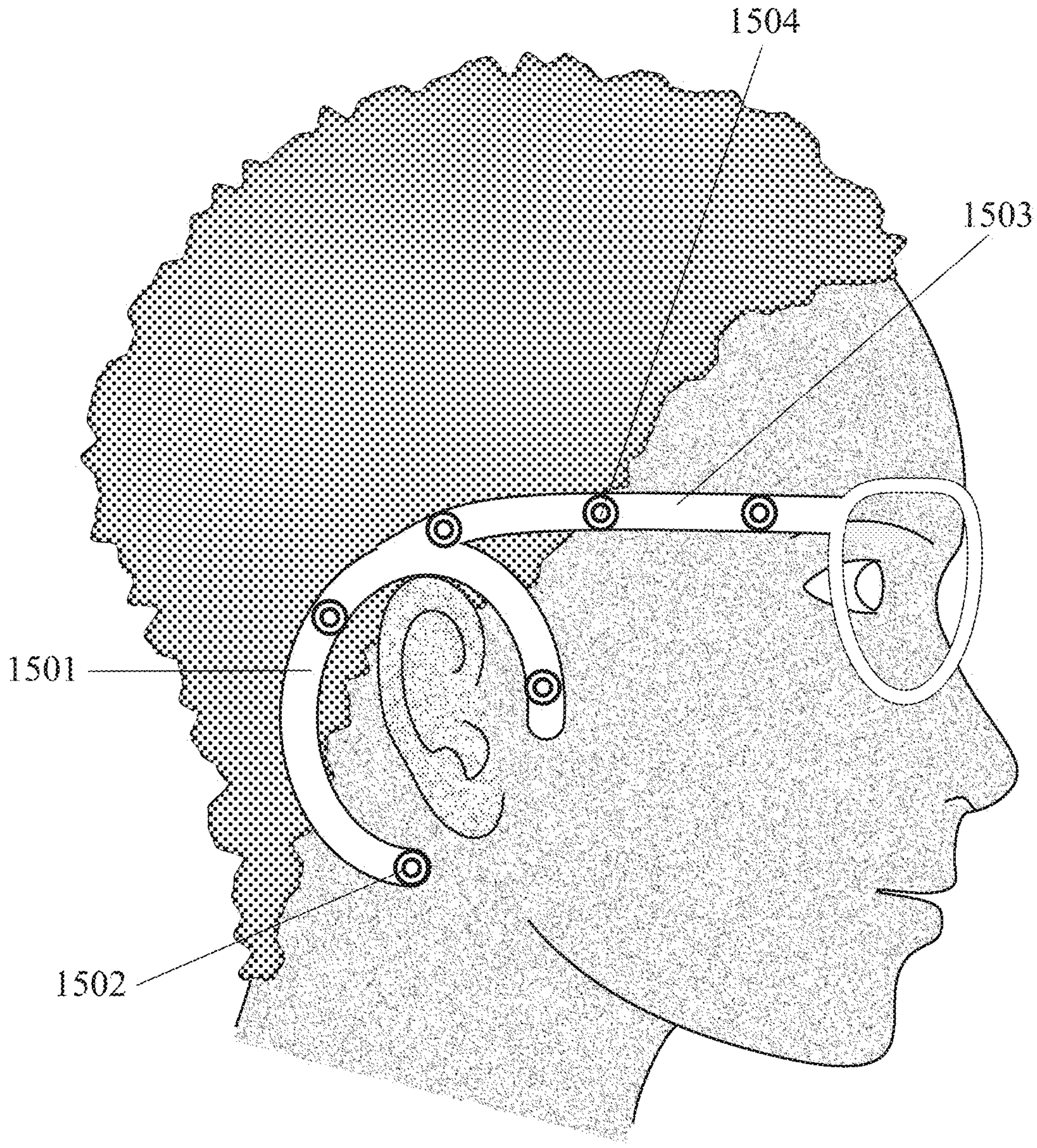
FIG. 15 shows an example of an integrated headset-and-eyewear device with partially-circumaural housings and electrodes.

FIG. 15 shows a left-side view of an example of an integrated headset-and-eyewear device with electrodes comprising: a left-side partially-circumaural housing 1501 (e.g. partial-annular and/or partial-toroidal band, ear cuff, or ear cushion) which encircles between 50% and 90% of a person's left auricle; a right-side partially-circumaural housing (e.g. partial-annular and/or partial-toroidal band, ear cuff, or each cushion) which encircles between 50% and 90% of the person's right auricle; an eyewear frame 1503 which spans the person's face from the left-side partially-circumaural housing to the right-side partially-circumaural housing; a first plurality of electrodes, including electrode 1502, on the left-side partially-circumaural housing which record biometric signals (e.g. brainwaves) from the person's brain; a second plurality of electrodes on the right-side partially-circumaural housing which record biometric signals from the person's brain; and a third plurality of electrodes, including electrode 1504, on the eyewear frame which record biometric signals from the person's brain. The right side of the integrated device is not shown in this figure, but it is assumed that the right side of the integrated device is symmetric to the left side.

In an example, an integrated headset-and-eyewear device can comprise: an eyewear frame (e.g. eyewear sidepiece) which holds at least one electrode (at a position selected from the group consisting of Nz, FP1, AF7, F7, FT7 and T7); a rear ear arm/portion which curves around the rear of a person's ear and holds at least one electrode (at a position selected from the group consisting of P9, TP9, TP7); and a front ear arm/portion which curves around the front of the person's ear and holds at least one third electrode (at an electrode position selected from the group consisting of TP7, T9, and T7). In an example, the rear ear arm/portion and the front ear arm/portion can together span between 50% and 90% of the circumference of a person's ear. In an example, the device can rest on the (tops of the) person's ears. Relevant variations discussed elsewhere in this disclosure or in priority-linked disclosures can also be applied to this example.

Figure 16:
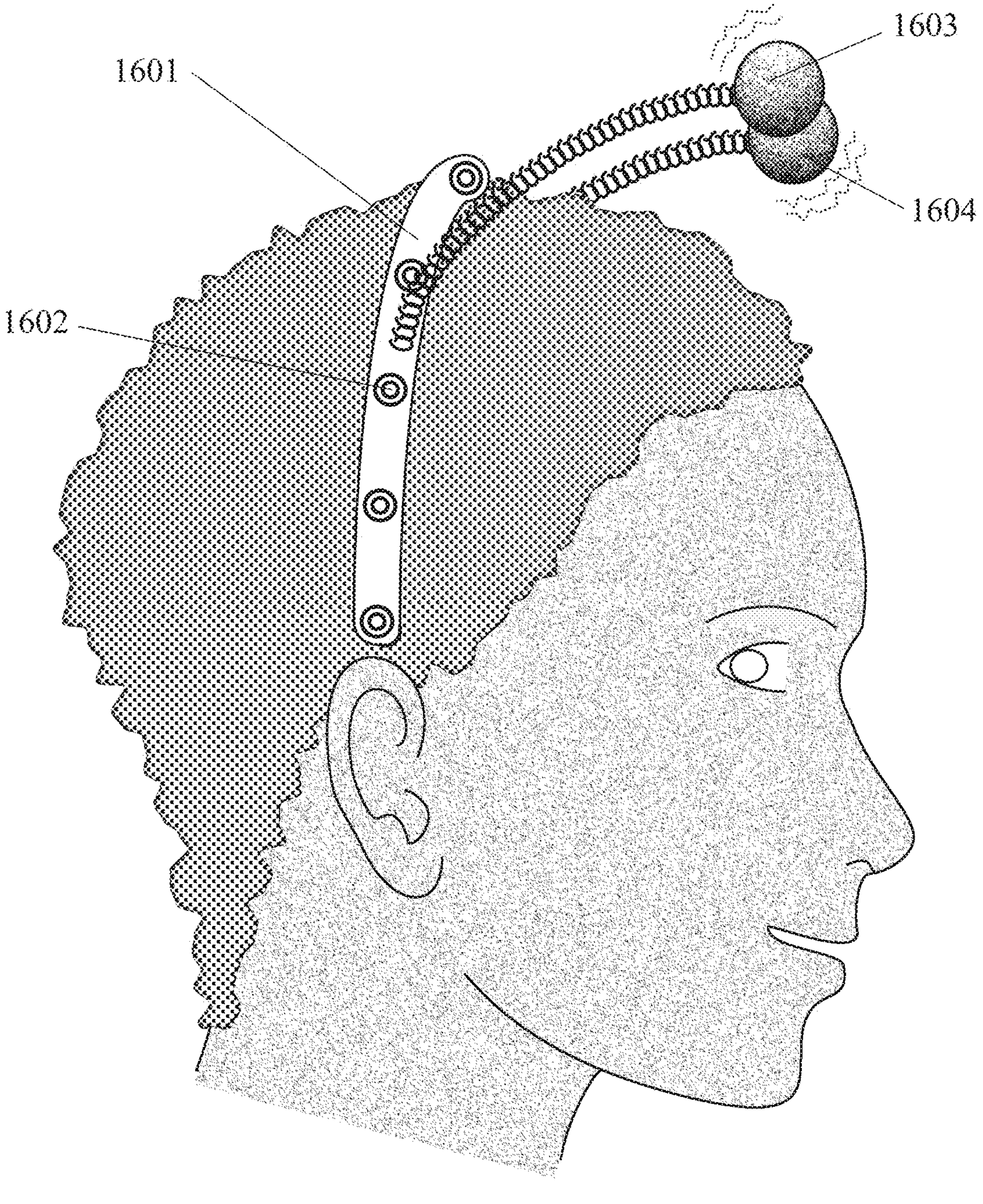
FIG. 16 shows an example of deely bobbers with electrodes.

FIG. 16 shows a left-side view of an example of deely-bobbers with electrodes comprising: an upper band 1601 which loops and/or curves over the upper half of the person's head; a left-side springy-thingy antenna (e.g. deely-bobber) 1603; a right-side springy-thingy antenna (e.g. deely-bobber) 1604; and a first plurality of electrodes, including electrode 1602, on the upper band. If you saw someone wearing this, you would probably mutter—"What was this guy thinking?" Well, that's the whole point. Relevant variations discussed in the Journey to Babel can also be applied to this example.

In an example, headphones can comprise: a left-side circumaural housing which encircles and covers a person's left auricle; a right-side circumaural housing which encircles and covers the person's right auricle; an upper band which loops and/or curves over the upper half of the person's head from the left-side circumaural housing to the right-side circumaural housing; a first plurality of electrodes on the left-side circumaural housing which records biometric signals from the person's brain; a second plurality of electrodes on the right-side circumaural housing which records biometric signals from the person's brain; and a third plurality of electrodes on the upper band which records biometric signals from the person's brain.

In an example, a circumaural housing can further comprise a speaker or other sound-emitting component. In an example, headphones can further comprise a data processor. In an example, headphones can further comprise a wireless data transmitter. In an example, headphones can further comprise a battery or other power source. In an example, a circumferential housing can be concave. In an example, most of a person's auricle can be within a concavity of the circumferential housing. In an example, a plurality of electrodes can be located at a subset of the following placement sites: CP1, CP2, CP3, CP4, CP5, CP6, CPz, FC1, FC2, FC3, FC4, FC5, FC6, FCz, O1, O2, Oz, P7, P8, PO7, PO8, TP7 and TP8. In an example, an upper band can bifurcate into two branches as it loops and/or curves over the upper half of the person's head. In an example, the two branches of the bifurcated upper band can diverge from each other at an angle between 20 to 80 degrees.

In an example, headphones with electrodes can comprise: a set of headphones; one or more electrodes which are configured by the set of headphones to be less than one inch from the surface of a person's head; a power source or power transducer; a data processor; and a data transmitter. In an example, the headphones can cover the person's ears and loop over the top of the person's head. In an example, electrodes can be located at a subset of the following MCN electrode placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8.

In an example, a headset with electrodes can comprise: a left-side partially-circumaural housing which encircles between 50% and 90% of a person's left auricle; a right-side partially-circumaural housing which encircles between 50% and 90% of the person's right auricle; an upper band which loops and/or curves over the upper half of the person's head from the left-side partially-circumaural housing to the right-side partially-circumaural housing; a first plurality of electrodes on the left-side circumaural housing which records biometric signals from the person's brain; a second plurality of electrodes on the right-side circumaural housing which records biometric signals from the person's brain; and a third plurality of electrodes on the upper band which records biometric signals from the person's brain.

In an example, a headset can further comprise a data processor, a wireless data transmitter, and a battery or other power source. In an example, a circumaural housing can partially-encircle, but not cover, a person's auricle. In an example, a partially-circumaural housing can comprise a partial-annular and/or partial-toroidal band. In an example, a partially-circumaural housing can comprise a partial-annular and/or partial-toroidal ear cuff or ear cushion. In an example, a circumferential gap in a partially-circumaural housing can be within an anterior half of a circumference around an auricle. In an example, a circumferential gap in a partially-circumaural housing can be within a lower half of a circumference around an auricle.

I claim:

1. Headphones with electrodes comprising:
- a set of headphones;
- one or more electrodes which are configured by the set of headphones to be less than one inch from the surface of a person's head;
- a power source or power transducer;
- a data processor; and
- a data transmitter.

2. The headphones in claim 1 wherein the headphones cover a person's ears and loop over the top of the person's head.

3. The headphones in claim 1 wherein the headphones further comprise an array of electrodes which are located at a subset of the following MCN electrode placement sites—CP1, CP2, CP3, CP4, CP5, CP6, CPz, FC1, FC2, FC3, FC4, FC5, FC6, FCz, O1, O2, Oz, P7, P8, PO7, PO8, TP7 and TP8.

4. A wearable brain activity monitor comprising:
- a head-worn sensor-positioning device which is configured to position a plurality of electrodes or other brain activity sensors at selected locations on a wearer's head, wherein the sensor-positioning device snuggly loops around a portion of the lateral perimeter of the wearer's ear.

5. The sensor-positioning device in claim 4 wherein the sensor-positioning device positions electrodes or other brain activity sensors at two or more locations selected from placement sites T7, T8, TP7 and TP8.

6. The sensor-positioning device in claim 4 wherein the sensor-positioning device loops around a percentage of the lateral perimeter of the wearer's ear in the range of 25% to 70%.

7. The sensor-positioning device in claim 4 wherein the sensor-positioning device loops around the wearer's ear between 9 o'clock to 5 o'clock locations, when locations are expressed in clock-hour positions.

8. The sensor-positioning device in claim 4 wherein a first end of the sensor-positioning device is between 270 degree and 350 degree locations and a second end of the device is between 10 degree and 90 degree locations, when locations are expressed in polar coordinates.

* * * * *